(12) United States Patent
Ogawa et al.

(10) Patent No.: US 11,189,802 B2
(45) Date of Patent: Nov. 30, 2021

(54) ORGANIC ELECTROLUMINESCENT ELEMENT

(71) Applicant: NIPPON STEEL CHEMICAL & MATERIAL CO., LTD., Tokyo (JP)

(72) Inventors: Junya Ogawa, Tokyo (JP); Masashi Tada, Tokyo (JP)

(73) Assignee: NIPPON STEEL CHEMICAL & MATERIAL CO., LTD., Tokyo (JP)

(*) Notice: Subject to any disclaimer, the term of this patent is extended or adjusted under 35 U.S.C. 154(b) by 239 days.

(21) Appl. No.: 16/606,100

(22) PCT Filed: Apr. 16, 2018

(86) PCT No.: PCT/JP2018/015633
§ 371 (c)(1),
(2) Date: Oct. 17, 2019

(87) PCT Pub. No.: WO2018/198844
PCT Pub. Date: Nov. 1, 2018

(65) Prior Publication Data
US 2021/0143340 A1 May 13, 2021

(30) Foreign Application Priority Data
Apr. 27, 2017 (JP) .............................. JP2017-088456

(51) Int. Cl.
*H01L 51/00* (2006.01)
*H01L 51/50* (2006.01)

(52) U.S. Cl.
CPC ...... *H01L 51/0072* (2013.01); *H01L 51/0067* (2013.01); *H01L 51/0085* (2013.01);
(Continued)

(58) Field of Classification Search
CPC ............. H01L 51/0072; H01L 51/0085; H01L 51/0067; H01L 51/5056
See application file for complete search history.

(56) References Cited

U.S. PATENT DOCUMENTS 9,142,710 B2 * 9/2015 Seo ..................... H01L 51/5221
2010/0187977 A1 7/2010 Kai et al.
(Continued)

FOREIGN PATENT DOCUMENTS

JP 2003-133075 A 5/2003
JP 2016-185914 A 10/2016
(Continued)

OTHER PUBLICATIONS

International Preliminary Report on Patentability and Written Opinion dated Nov. 7, 2019, in PCT/JP2018/015633 (Forms PCT/IB/338, PCT/IB/373, and PCT/ISA/237).

*Primary Examiner* — Dung A. Le
(74) *Attorney, Agent, or Firm* — Birch, Stewart, Kolasch & Birch, LLP

(57) ABSTRACT

There is provided an organic EL element having high efficiency and high driving stability despite having a low driving voltage. An organic electroluminescent element has a light-emitting layer between an anode and a cathode which face each other, and the light-emitting layer contains a first host selected from among indolocarbazole compounds represented by formula (1), a second host selected from among biscarbazole compounds represented by formula (2), and a light-emitting dopant material:

(Continued)

(52) U.S. Cl.
CPC ...... *H01L 51/5016* (2013.01); *H01L 51/5056* (2013.01); *H01L 51/5072* (2013.01); *H01L 2251/5384* (2013.01)

(56) References Cited

U.S. PATENT DOCUMENTS

| | | |
|---|---|---|
| 2010/0295444 A1 | 11/2010 | Kuma et al. |
| 2012/0241732 A1 | 9/2012 | Endo et al. |
| 2014/0197386 A1 | 7/2014 | Kim et al. |
| 2014/0306207 A1 | 10/2014 | Nishimura et al. |
| 2014/0374728 A1 | 12/2014 | Adamovich et al. |
| 2015/0001488 A1 | 1/2015 | Min et al. |
| 2015/0207079 A1* | 7/2015 | Cho .................. H01L 51/0073 257/40 |
| 2015/0236262 A1 | 8/2015 | Cho et al. |
| 2016/0111664 A1 | 4/2016 | Ito et al. |
| 2016/0163995 A1 | 6/2016 | Kang et al. |
| 2016/0190475 A1 | 6/2016 | Kim et al. |
| 2016/0308138 A1* | 10/2016 | Kim .................. H01L 51/5012 |
| 2017/0069848 A1 | 3/2017 | Zeng et al. |
| 2018/0138420 A1 | 5/2018 | Tada et al. |

FOREIGN PATENT DOCUMENTS

| | | |
|---|---|---|
| WO | WO 2011/136755 A1 | 11/2011 |
| WO | WO 2015/156587 A1 | 10/2015 |
| WO | WO 2016/013867 A1 | 1/2016 |

\* cited by examiner

[C1]

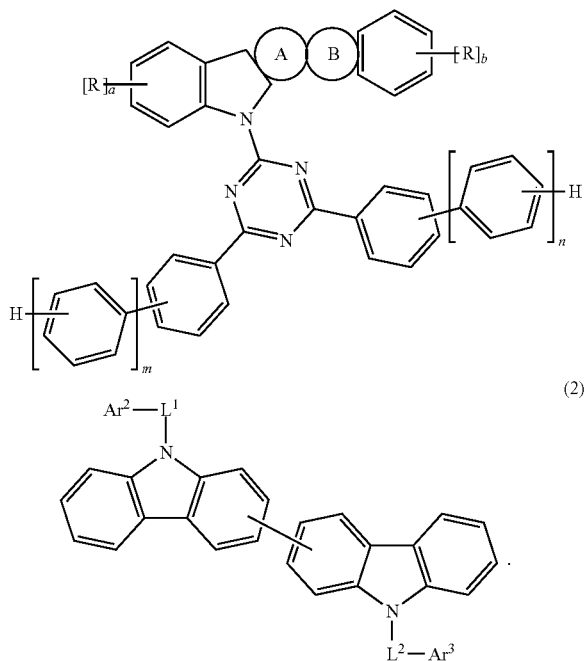

12 Claims, 1 Drawing Sheet

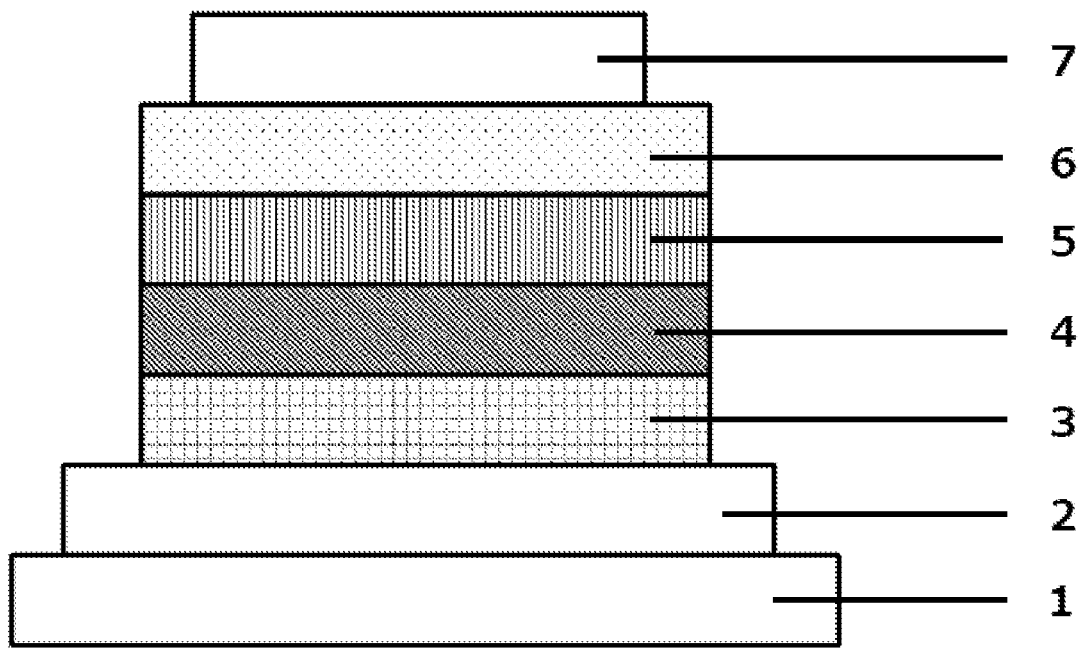

ORGANIC ELECTROLUMINESCENT ELEMENT

TECHNICAL FIELD

The present invention relates to an organic electroluminescent element (referred to as an organic EL element), and specifically, to an organic EL element comprising a light-emitting layer containing a first host, a second host, and a light-emitting dopant material.

BACKGROUND ART

When a voltage is applied to an organic EL element, holes are injected from an anode and electrons are injected from a cathode to a light-emitting layer. Thus, in the light-emitting layer, injected holes and electrons recombine to generate excitons. In this case, according to statistical rules of electron spins, singlet excitons and triplet excitons are generated at a ratio of 1:3. It is said that the internal quantum efficiency of a fluorescence-emitting organic EL element using light emission from singlet excitons is limited to 25%. Meanwhile, it has been known that, in a phosphorescent organic EL element using light emission from triplet excitons, when intersystem crossing is efficiently performed from singlet excitons, the internal quantum efficiency is raised to 100%.

However, for phosphorescent organic EL elements, prolonging the lifespan is a technical issue.

In addition, recently, organic EL elements using delayed fluorescence and having high efficiency have been developed. For example, PTL 1 discloses an organic EL element using a triplet-triplet fusion (TTF) mechanism which is one of delayed fluorescence mechanisms. The TTF mechanism utilizes a phenomenon in which singlet excitons are generated due to collision of two triplet excitons, and it is thought that the internal quantum efficiency can theoretically be raised to 40%. However, since the efficiency is lower compared to phosphorescent organic EL elements, further improvement in efficiency is required.

PTL 2 discloses an organic EL element using a thermally activated delayed fluorescence (TADF) mechanism. The TADF mechanism utilizes a phenomenon in which reverse intersystem crossing from triplet excitons to singlet excitons is generated in a material having a small energy difference between a singlet level and a triplet level, and it is thought that the internal quantum efficiency can theoretically be raised to 100%. However, further improvement in lifespan characteristics is required as in the case of phosphorescent elements.

CITATION LIST

Patent Literature

[PTL 1] WO 2010/134350 A
[PTL 2] WO 2011/070963 A
[PTL 3] WO 2008/056746 A
[PTL 4] JP 2003-133075 A
[PTL 5] WO 2013/062075 A
[PTL 6] US 2014/0374728 A
[PTL 7] US 2014/0197386 A
[PTL 8] US 2015/0001488 A
[PTL 9] US 2015/0236262 A
[PTL 10] WO 2016/194604 A
[PTL 11] WO 2011/136755 A

PTL 3 discloses use of an indolocarbazole compound as a host material. PTL 4 discloses use of a biscarbazole compound as a host material.

PTL 5 and 6 disclose use of a biscarbazole compound as a mixed host. PTL 7, 8, 9, and 10 disclose use of an indolocarbazole compound and a biscarbazole compound as a mixed host.

PTL 11 discloses use of a host material in which a plurality of hosts containing an indolocarbazole compound are premixed.

However, none of these can be said to be sufficient, and further improvement is desired.

SUMMARY OF INVENTION

In order to apply an organic EL element to a display element such as a flat panel display or a light source, it is necessary to improve the luminous efficiency of the element and to sufficiently secure stability during driving at the same time. An object of the present invention is to provide an organic EL element having high efficiency and high driving stability despite having a low driving voltage.

The present invention relates to an organic EL element comprising one or more light-emitting layer between an anode and a cathode which face each other, wherein at least one light-emitting layer contains a first host selected from among compounds represented by the following formula (1), a second host selected from among compounds represented by the following formula (2), and a light-emitting dopant material.

[C1]

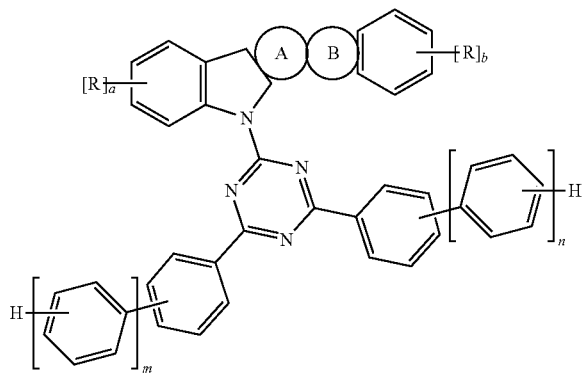

(1)

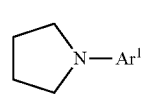

(1a)

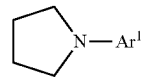

(1b)

(here, the ring A is an aromatic hydrocarbon ring represented by formula (1a), the ring B is a heterocycle represented by formula (1b), and the ring A and the ring B are each fused to an adjacent ring at any position, $Ar^1$ represents a phenyl group, a biphenyl group or a terphenyl group, R each independently represents an aliphatic hydrocarbon group having 1 to 10 carbon atoms, an aromatic hydrocarbon group having 6 to 10 carbon atoms, or an aromatic heterocyclic group having 3 to 12 carbon atoms, a, b, and c represent the number of substitutions and each independently represents an integer of 0 to 3, and m and n represent the number of repetitions, and each independently represents an integer of 0 to 2, and preferably, when $Ar^1$ is a phenyl group, m+n is an integer of 1 to 4).

[C2]

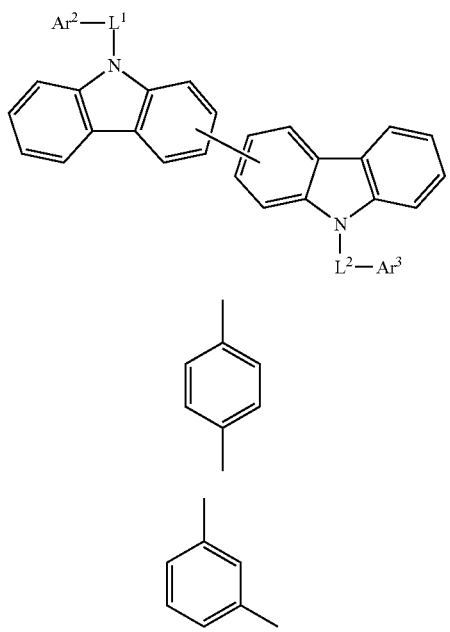

(2)

(2a)

(2b)

(here, $Ar^2$ and $Ar^3$ independently represent a hydrogen atom, an aromatic hydrocarbon group having 6 to 14 carbon atoms, or a group in which two of the aromatic hydrocarbon groups are linked to each other, and the aromatic hydrocarbon groups to be linked to each other may be the same as or different from each other, with the proviso that $Ar^2$ and $Ar^3$ are not both a hydrogen atom, and $L^1$ and $L^2$ represent a phenylene group represented by formula (2a) or formula (2b), and preferably, $L^1$ and $L^2$ are not the same (except for a case in which $Ar^2$ or $Ar^3$ is a hydrogen atom)).

Preferable embodiments of formula (2) include formulae (3) to (5), and formula (4) or (5) is more preferable.

[C3]

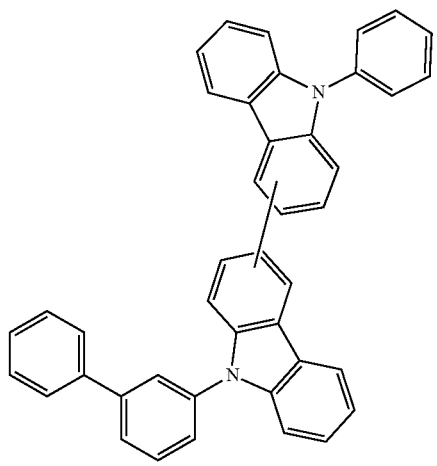

(3)

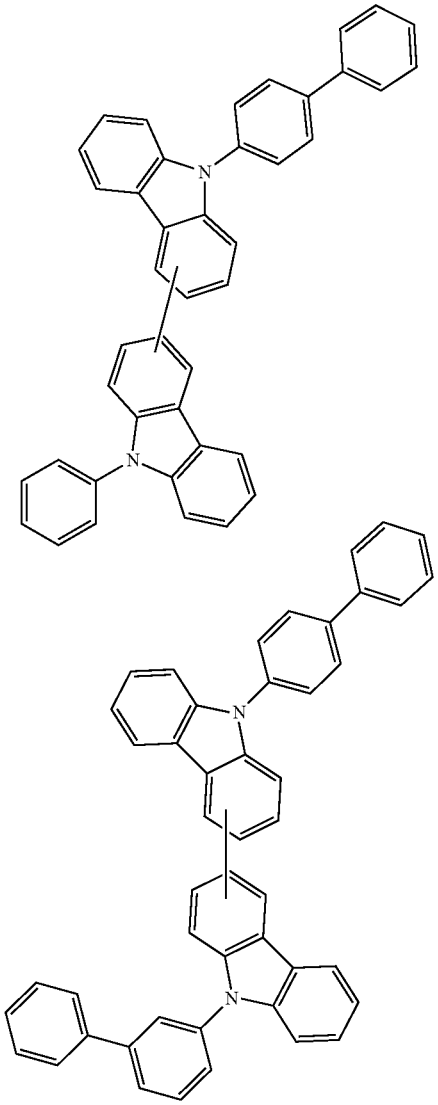

(4)

(5)

Preferable embodiments of formula (1) include formulae (6) to (11), and formula (6), (7), (8), or (9) is preferable, and formula (6) is more preferable.

[C4]

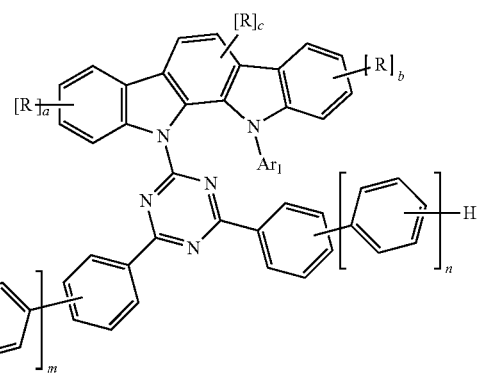

(6)

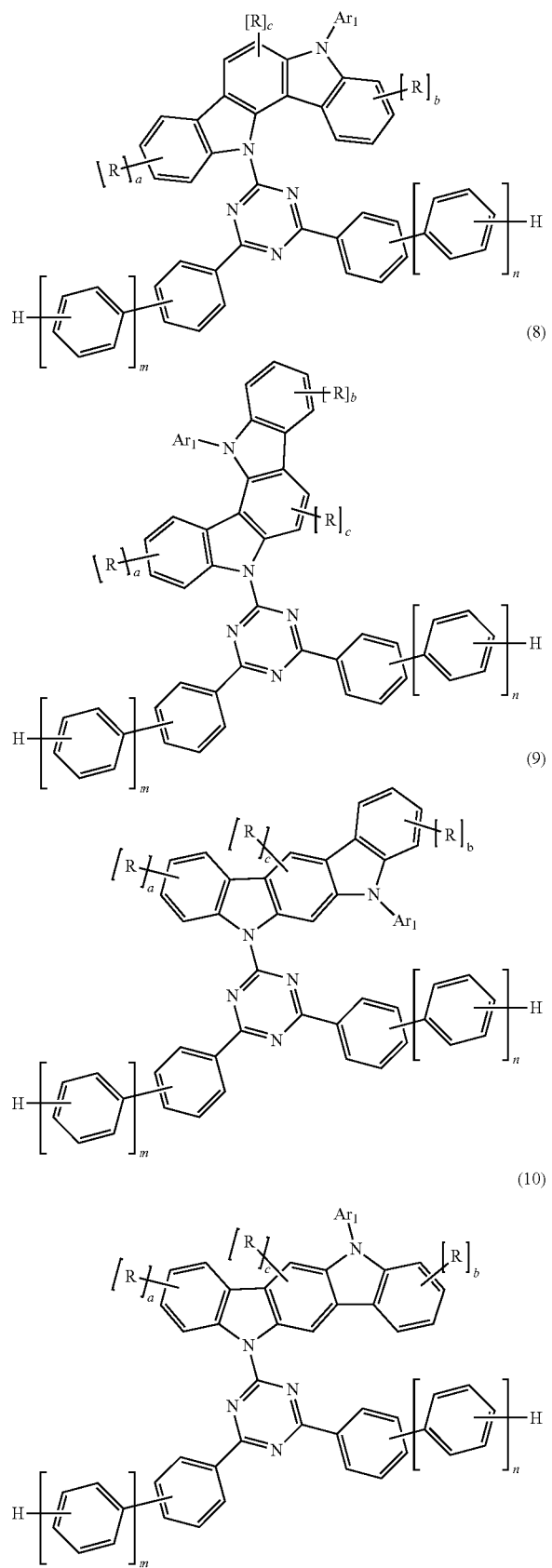

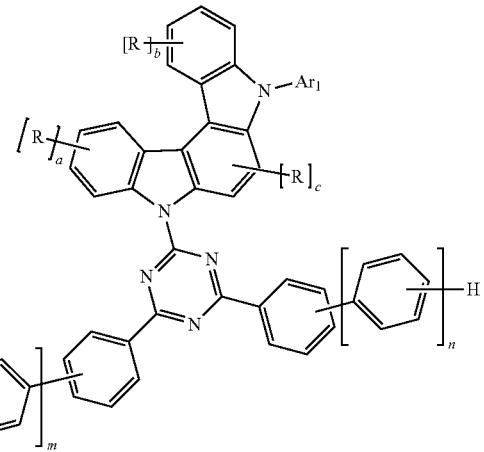

Preferably, the light-emitting layer is a vapor deposition layer formed according to vacuum vapor deposition, and the first host and the second host are used by being mixed in advance before vapor deposition. In addition, preferably, a difference between 50% weight reduction temperatures of the first host and the second host is within 20° C., or a proportion of the first host is larger than 20 wt % and less than 55 wt % with respect to a total amount of the first host and the second host.

The light-emitting dopant material can be a phosphorescent dopant material, a fluorescence-emitting dopant material or a thermally activated delayed fluorescence-emitting dopant material. Examples of the phosphorescent dopant material include an organic metal complex containing at least one metal selected from among ruthenium, rhodium, palladium, silver, rhenium, osmium, iridium, platinum and gold.

In addition, preferably, in the organic EL element, a hole blocking layer adjacent to the light-emitting layer is provided, and the hole blocking layer contains a compound represented by formula (1).

In addition, the present invention relates to a method of producing an organic electroluminescent element including a step of, when the above organic electroluminescent element is produced, mixing a first host and a second host to prepare a pre-mixture, and then vapor-depositing a host material containing the pre-mixture to form a light-emitting layer.

In order to improve element characteristics, it is necessary to increase durability of a material used for an organic layer against charges, and particularly, in the light-emitting layer, it is important to reduce leakage of excitons and charges to surrounding layers. In order to reduce leakage of charges/excitons, alleviating deviation of a light emission area in the light-emitting layer is effective. For this, it is necessary to control both amounts of charges (electrons/holes) injected into the light-emitting layer and both amounts of charges transported in the light-emitting layer such that they are within a preferable range.

Here, the indolocarbazole compound of formula (1) has high framework stability and can control injection and transport properties of both charges to some extent according to isomers or substituents. However, it is difficult to independently control both amounts of charges injected and transported so that they are within a preferable range as described above. On the other hand, the biscarbazole compound of formula (2) can control charge injection and transport properties at a high level when types and the number of substituents thereof are changed. In addition, the biscarbazole compound has a higher lowest excited triplet energy than a biscarbazole compound in which a fused aromatic group is incorporated because a substituent other than a fused ring is incorporated on a nitrogen atom, and also has high amorphous stability, and has high framework stability like the indolocarbazole compound. Therefore, when a mixture of the indolocarbazole compound and the biscarbazole compound is used, an amount of charges injected into the organic layer can be adjusted to a preferable range, and more favorable element characteristics can be expected. In particular, in the case of a delayed fluorescence-emitting EL element or a phosphorescent EL element, when a mixture of an indolocarbazole compound having at least one biphenyl group or terphenyl group on N or a triazine ring substituted on N and a biscarbazole compound having a phenylene group in which an aromatic hydrocarbon group is substituted on at least one N is used, the balance between charge injection and transport properties of holes and electrons is suitable, and also a lowest excited triplet energy sufficiently high to confine the excitation energy generated in the light-emitting layer is provided so that there is no outflow of energy from the inside of the light-emitting layer, and high efficiency and a prolonged lifespan can be obtained at a low voltage.

BRIEF DESCRIPTION OF DRAWINGS

FIG. 1 is a cross-sectional view schematically showing an example of an organic EL element.

DESCRIPTION OF EMBODIMENTS

An organic EL element of the present invention has at least one light-emitting layer between an anode and a cathode which face each other and at least one of light-emitting layers includes a vapor deposition layer containing a first host, a second host, and a light-emitting dopant material. The vapor deposition layer can be produced according to vacuum vapor deposition. The first host is a compound represented by formula (1), and the second host is a compound represented by formula (2). The organic EL element has a plurality of organic layers between an anode and a cathode which face each other, but at least one of the plurality of layers is a light-emitting layer, and a plurality of light-emitting layers may be provided.

Formula (1) will be described.

The ring A is an aromatic hydrocarbon ring represented by formula (1a), the ring B is a heterocycle represented by formula (1b), and the ring A and the ring B are each fused to an adjacent ring at any position.

$Ar^1$ represents a phenyl group, a biphenyl group, or a terphenyl group. Preferable examples thereof include a phenyl group or a biphenyl group, and more preferable examples thereof include a phenyl group. Here, the biphenyl group is a group represented by -Ph-Ph, the terphenyl group is a group represented by -Ph-Ph-Ph or Ph(-Ph)-Ph, and Ph is linked at any position (o-position, m-position, p-position). Here, Ph is a phenyl group or a phenylene group.

R each independently represents an aliphatic hydrocarbon group having 1 to 10 carbon atoms, an aromatic hydrocarbon group having 6 to 10 carbon atoms, or an aromatic heterocyclic group having 3 to 12 carbon atoms. Preferable examples thereof include an aliphatic hydrocarbon group having 1 to 8 carbon atoms, a phenyl group, and an aromatic heterocyclic group having 3 to 9 carbon atoms. More preferable examples thereof include an aliphatic hydrocarbon group having 1 to 6 carbon atoms, a phenyl group, and an aromatic heterocyclic group having 3 to 6 carbon atoms.

Specific examples of the aliphatic hydrocarbon group having 1 to 10 carbon atoms include methyl, ethyl, propyl, butyl, pentyl, hexyl, heptyl, octyl, nonyl, and decyl. An alkyl group having 1 to 4 carbon atoms is preferable.

Specific examples of the aromatic hydrocarbon group having 6 to 10 carbon atoms or the aromatic heterocyclic group having 3 to 12 carbon atoms include aromatic groups formed by taking one H from benzene, naphthalene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, benzothiadiazole, dibenzofuran, dibenzothiophene, dibenzoselenophene, or carbazole. Preferable examples thereof include aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, or benzothiadiazole. More preferable examples thereof include aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, or oxadiazole.

a, b, and c represent the number of substitutions, and each independently represents an integer of 0 to 3, and are preferably an integer of 0 or 1. m and n represent the number of repetitions, and each independently represents an integer of 0 to 2, and is preferably an integer of 0 or 1. Here, m+n is preferably an integer of 0 or 1 or more, and more preferably an integer of 1, 2 or 3. Here, when $Ar^1$ is a phenyl group, m+n is preferably an integer of 1 to 4, and more preferably an integer of 1, 2 or 3.

Preferable embodiments of formula (1) include formulae (6) to (11). In formulae (6) to (11), symbols the same as those in formula (1) have the same meanings as in formula (1).

Specific examples of compounds represented by formula (1) are shown below, but the present invention is not limited to such exemplary compounds.

[C5]
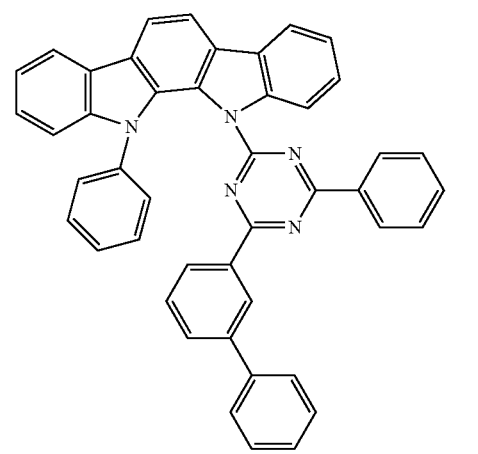
1-1
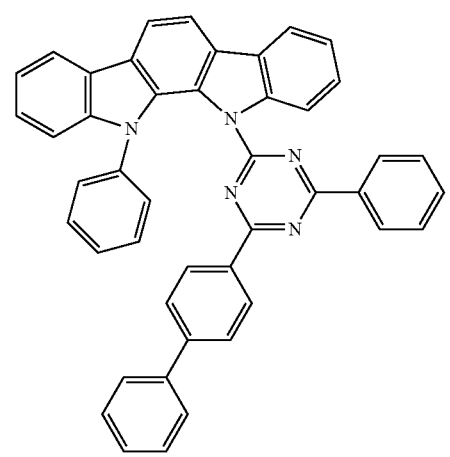
1-2
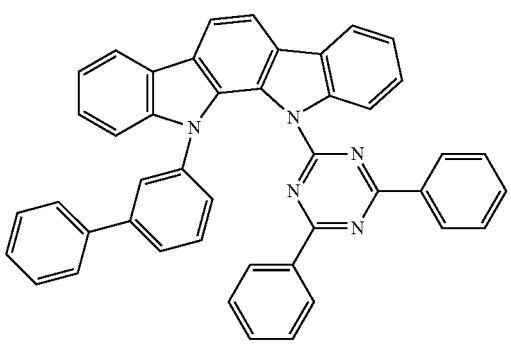
1-3
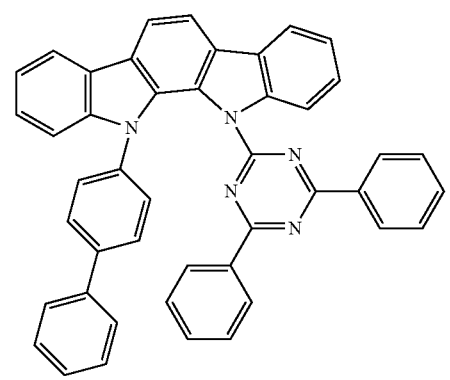
1-4
-continued
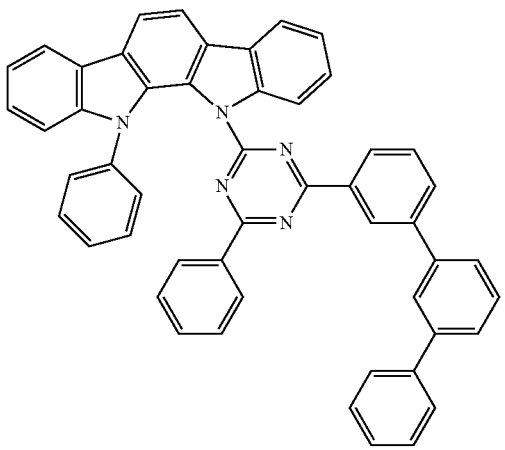
1-5
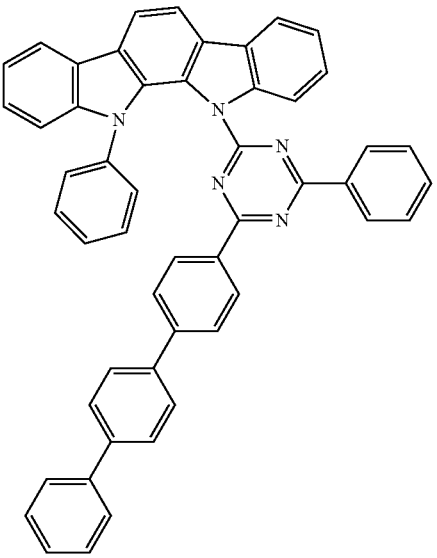
1-6
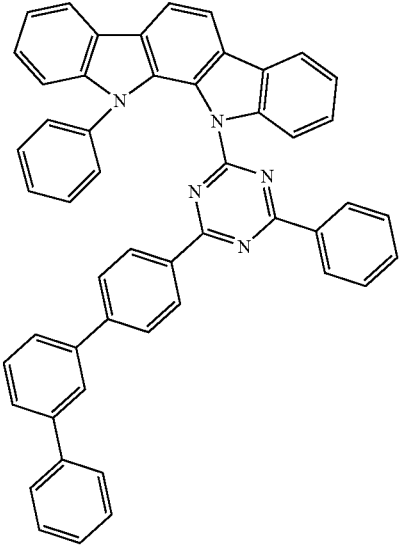
1-7

1-8
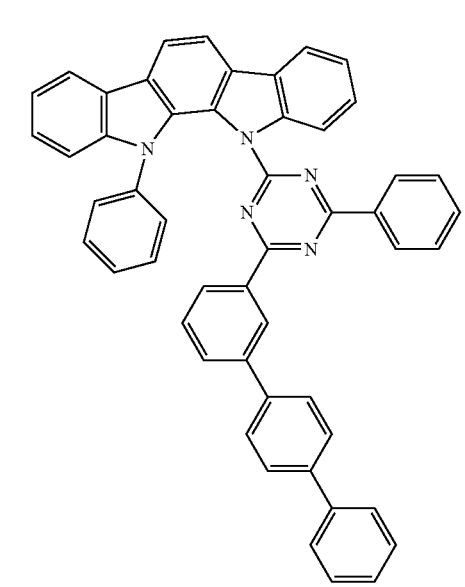
1-9
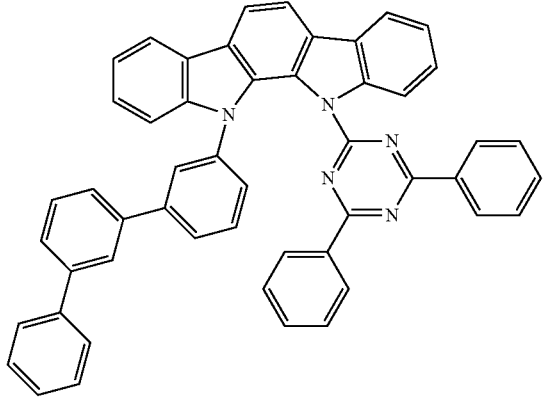
1-10
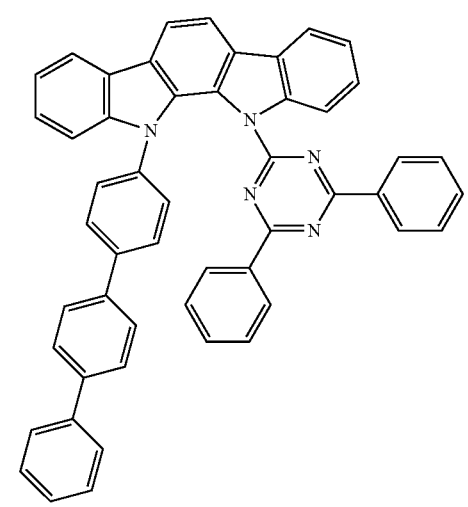
1-11
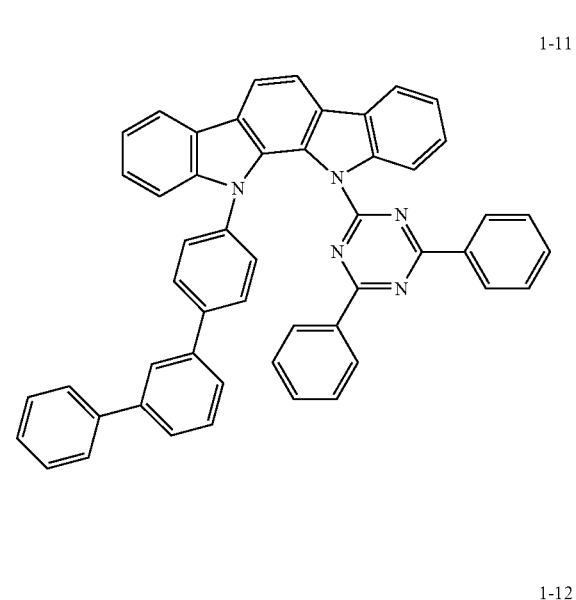
1-12
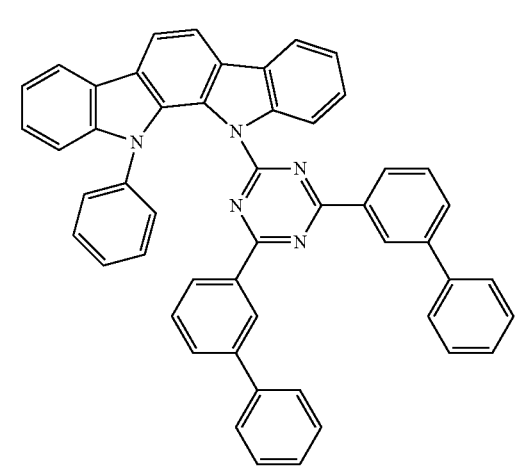
[C6]
1-13

1-14
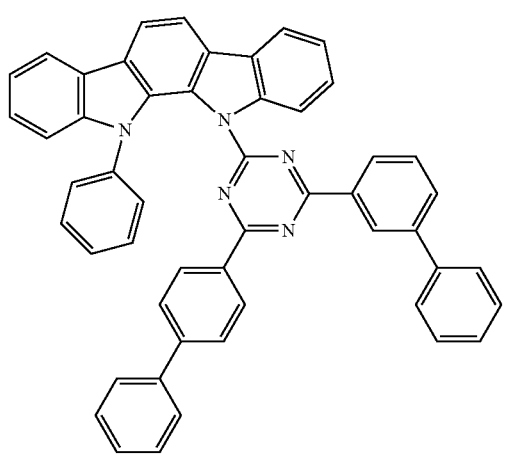
1-15
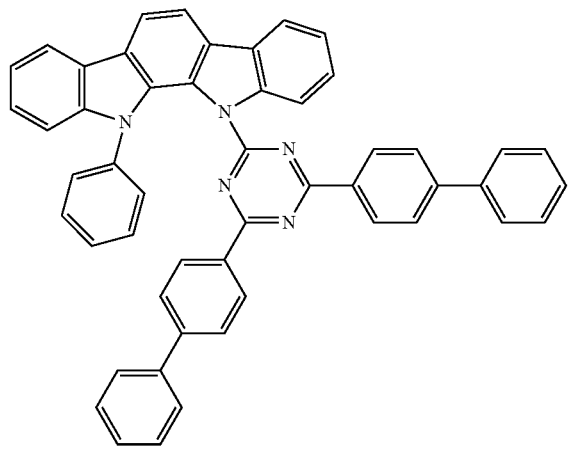
1-16
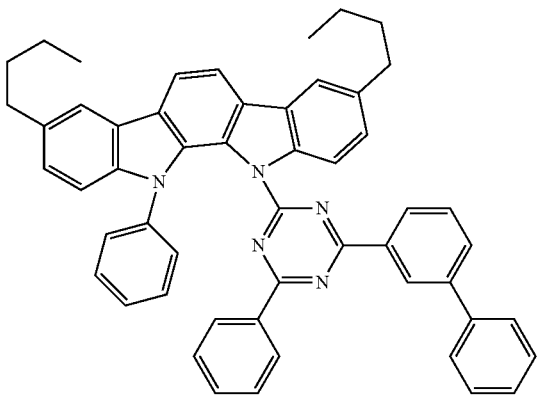
1-17
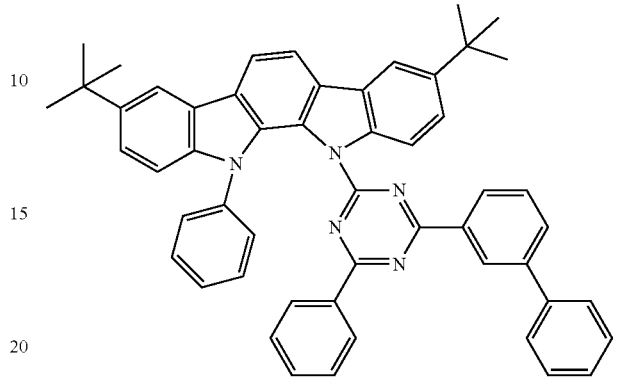
1-18
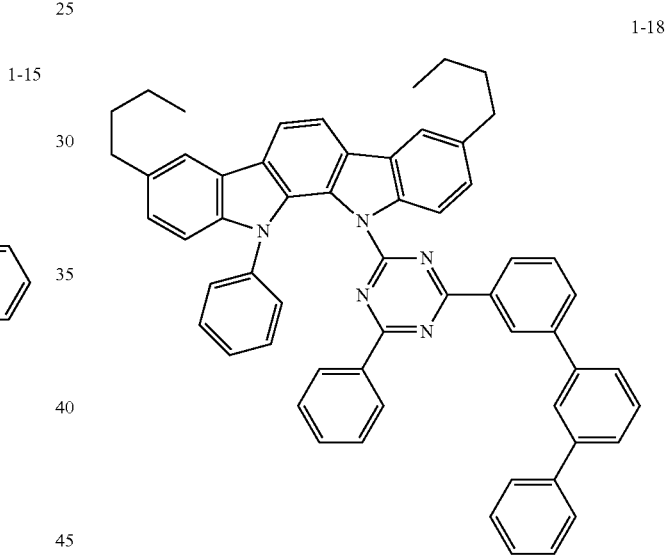
1-19
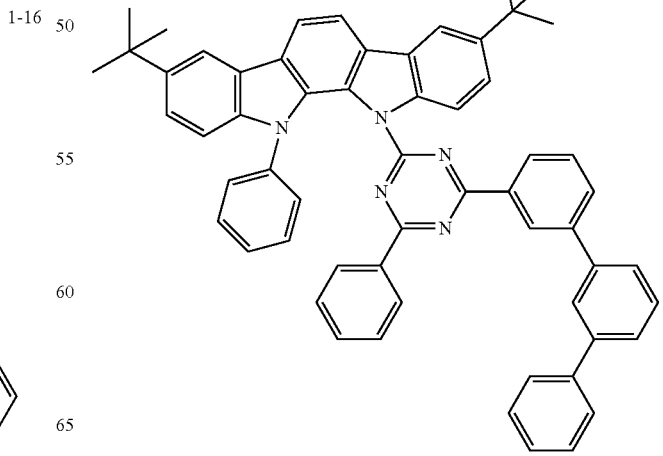

1-20
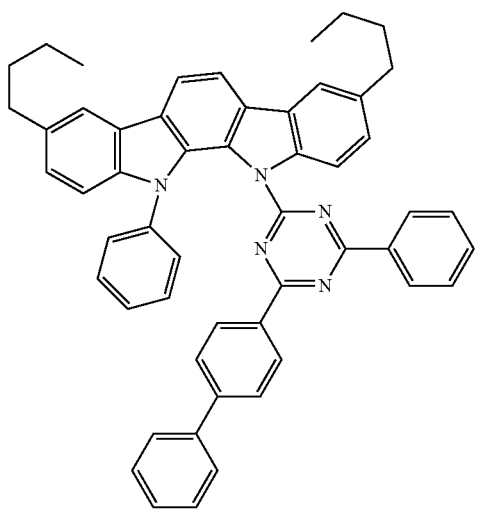
1-21
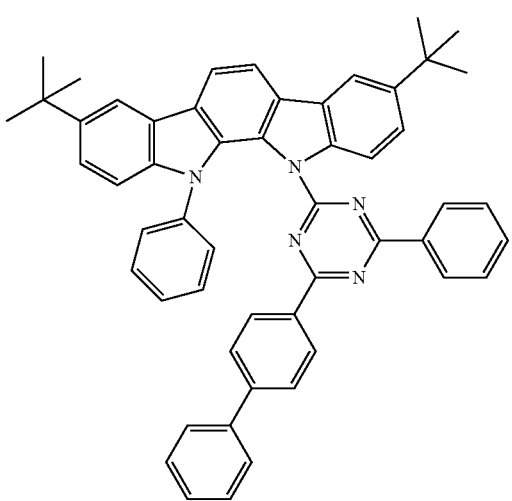
1-22
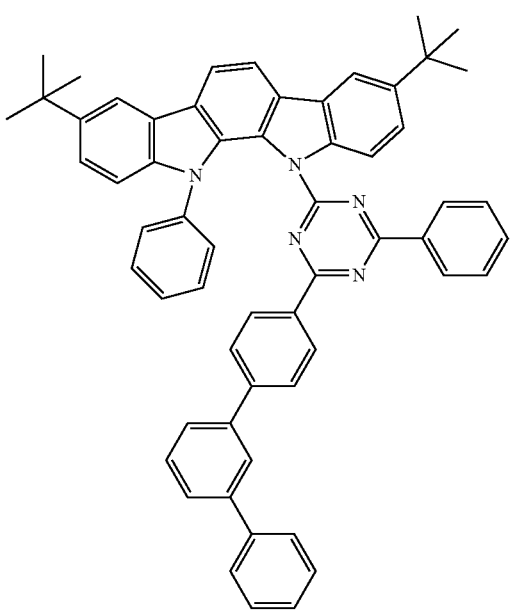
1-23
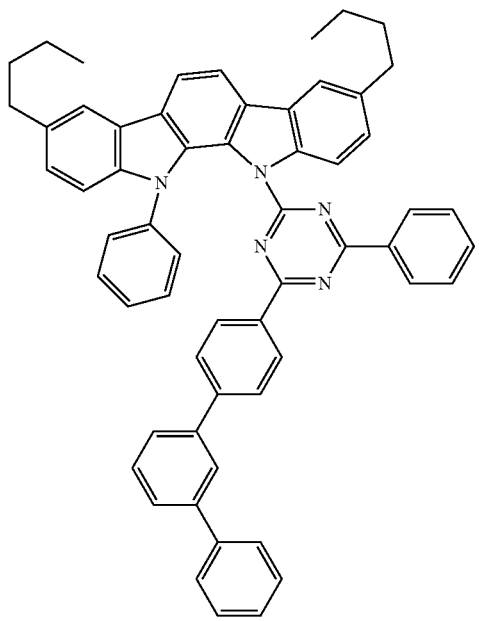
1-24
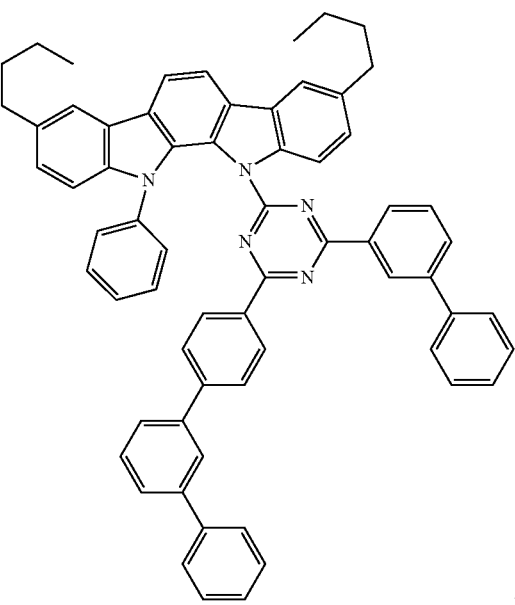
1-25
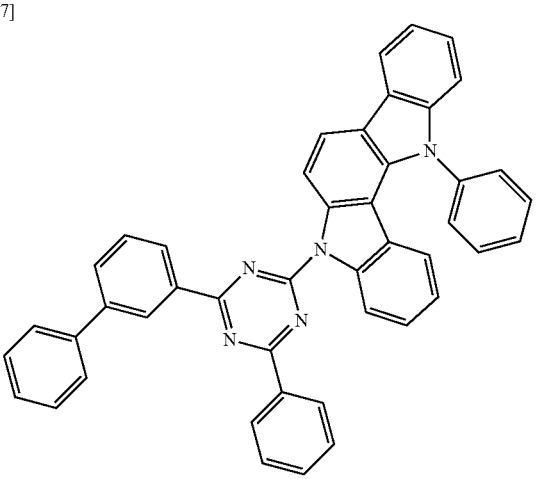

1-26
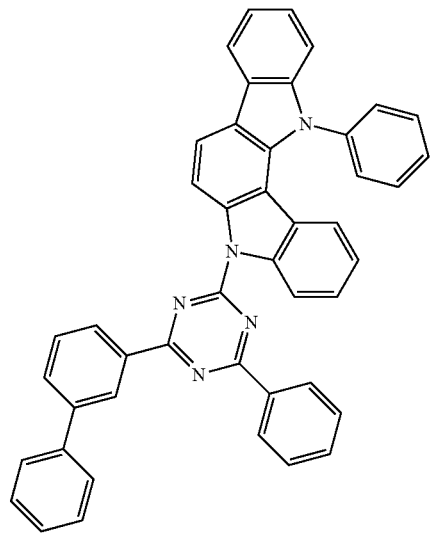
1-27
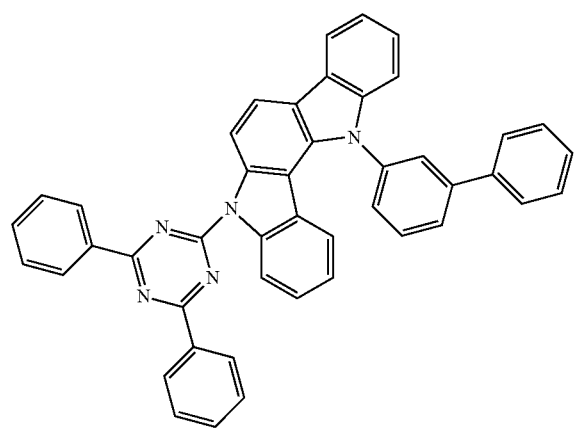
1-28
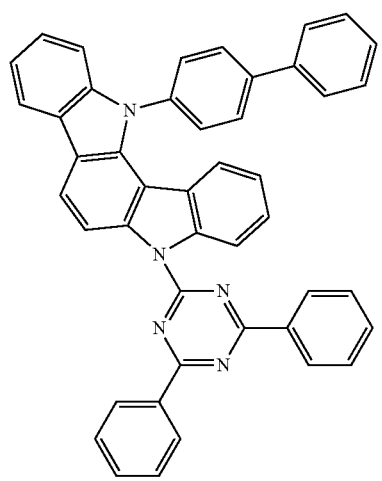
1-29
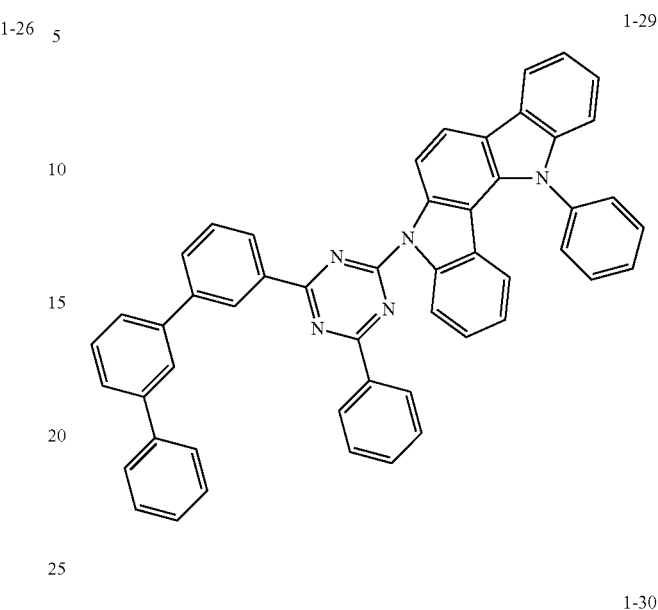
1-30
1-31
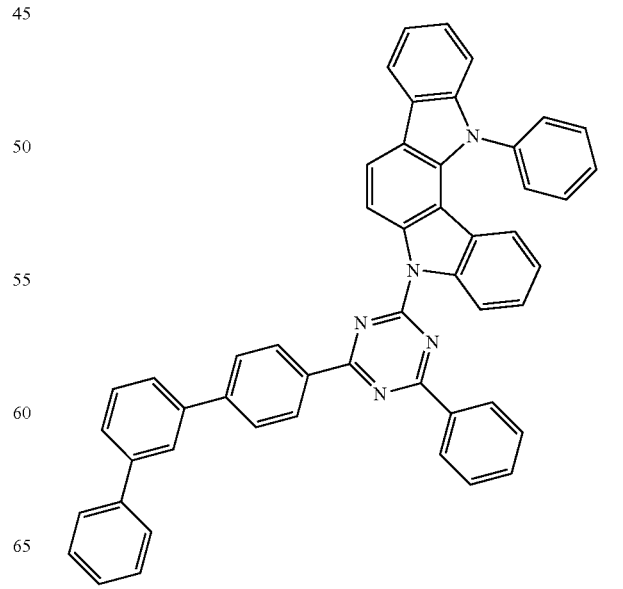

1-32
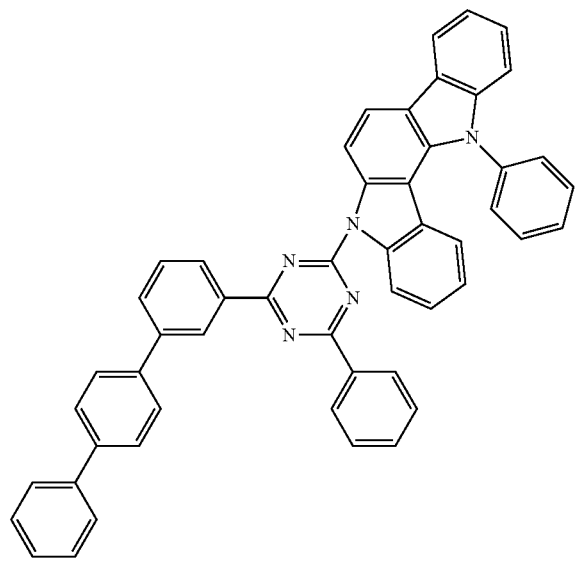
1-33
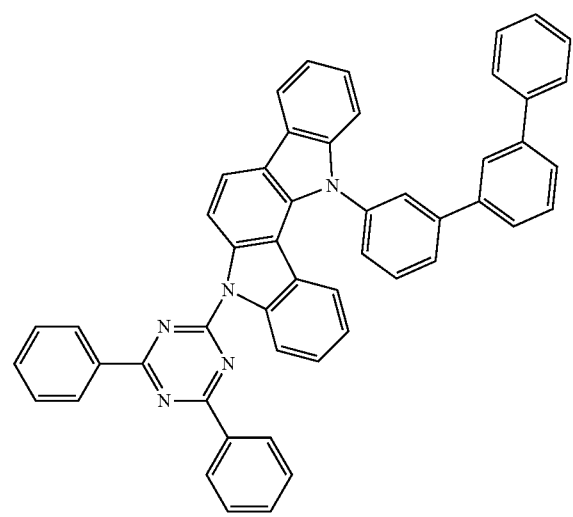
1-34
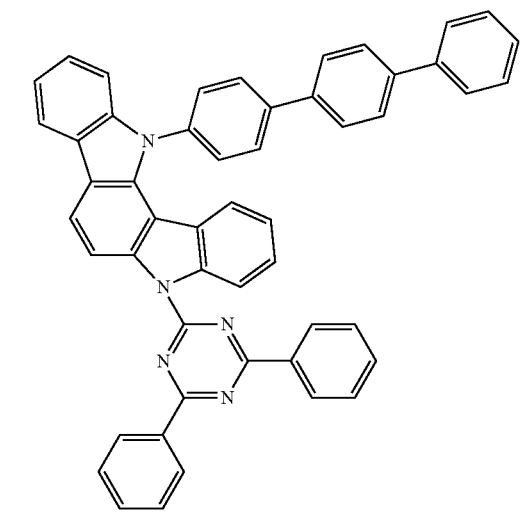
1-35
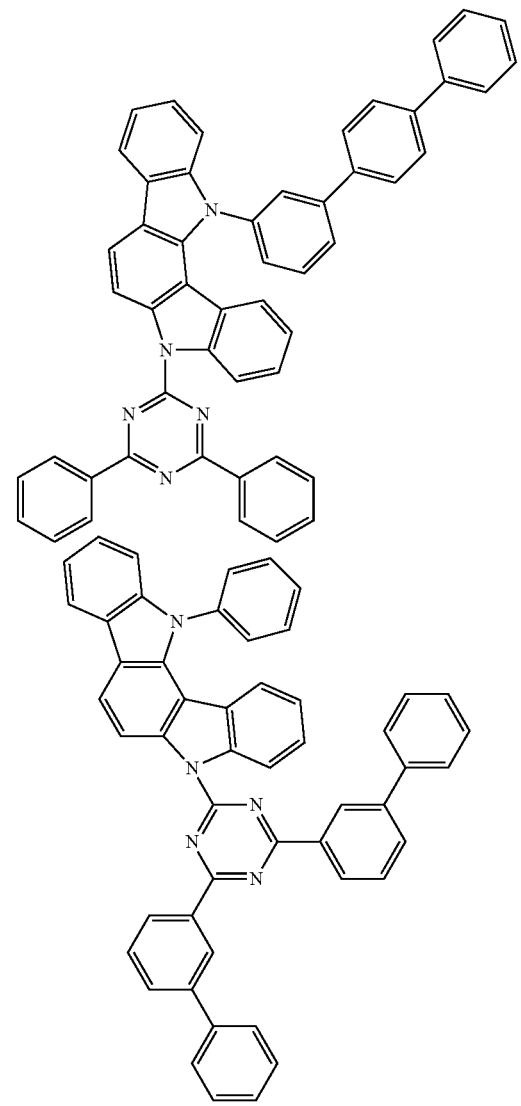
1-36
1-37
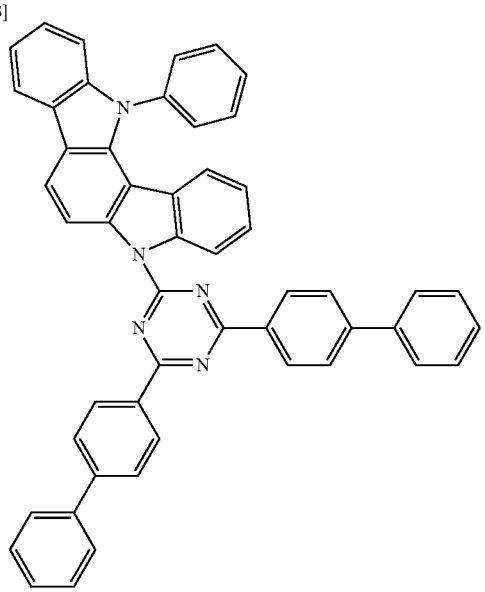

1-38
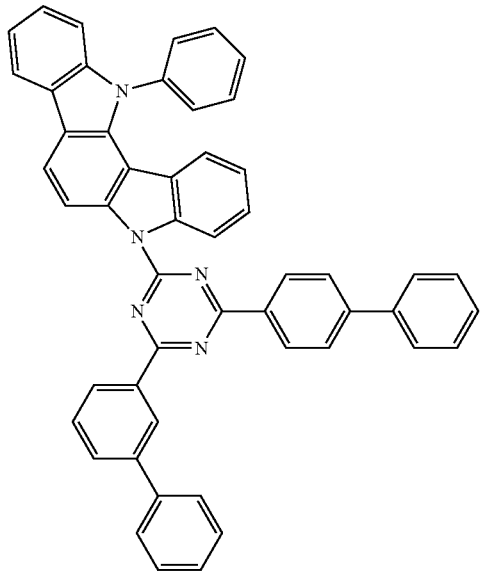
1-39
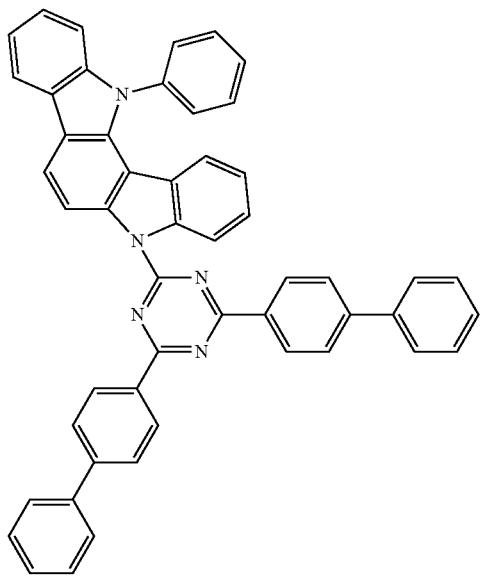
1-40
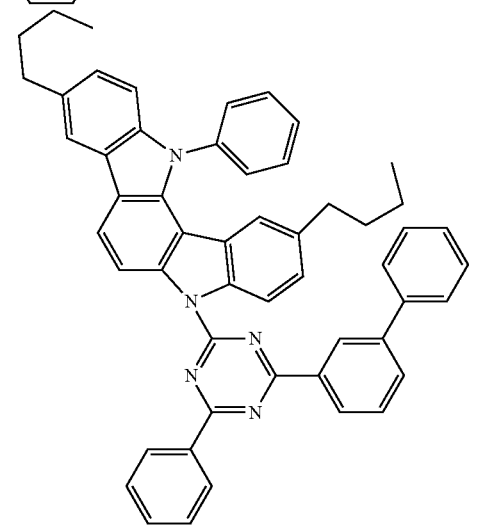
1-41
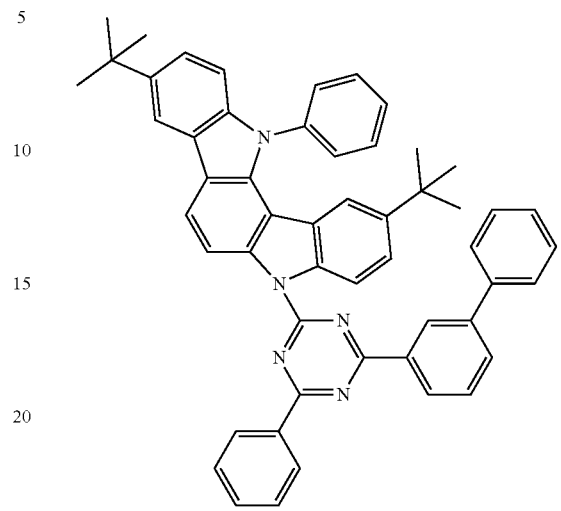
1-42
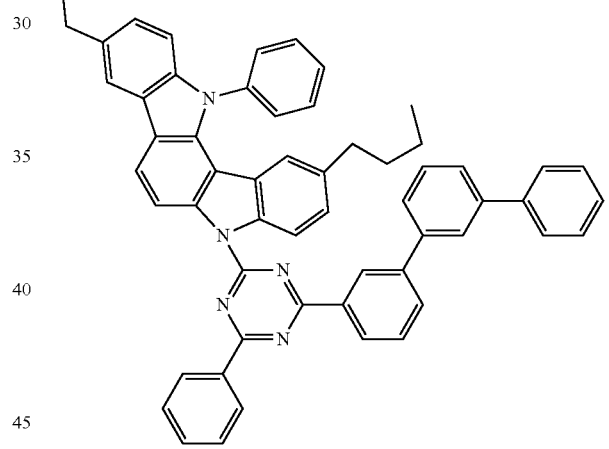
1-43
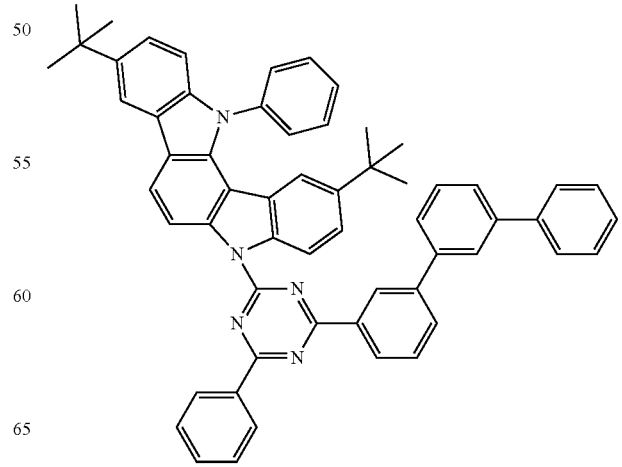

1-44
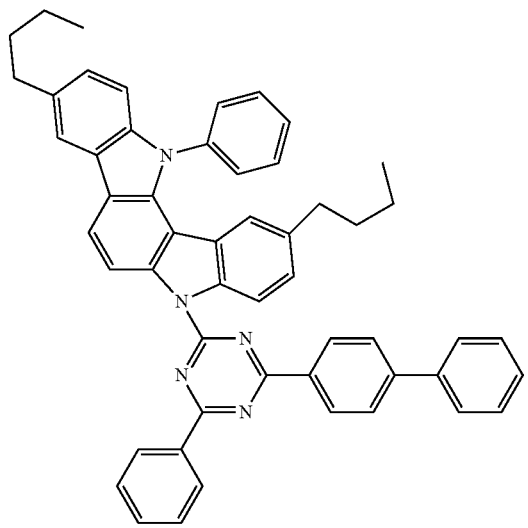
1-45
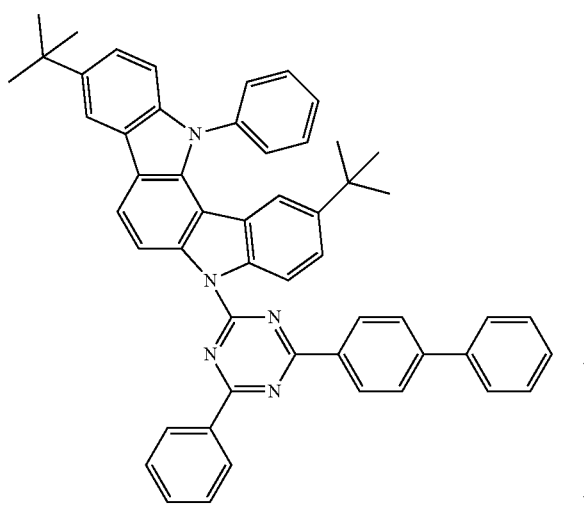
[C9]
1-46
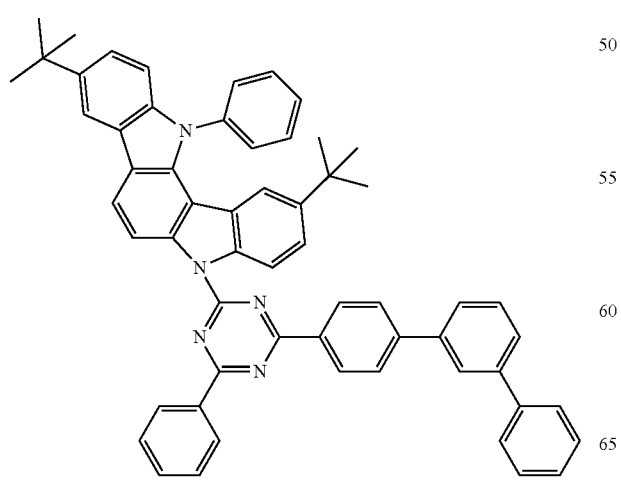
1-47
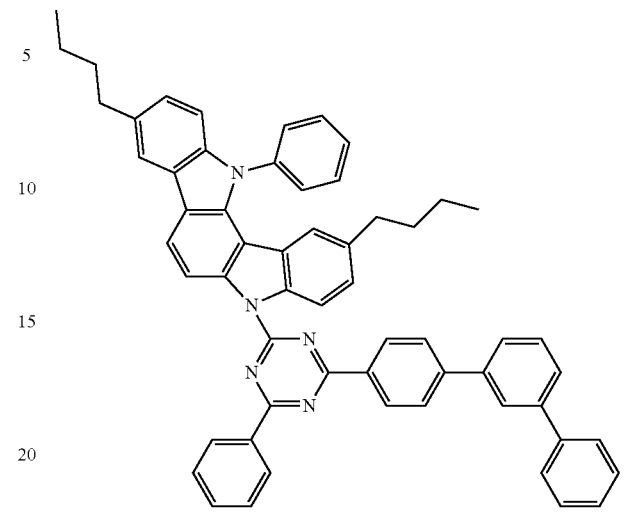
1-48
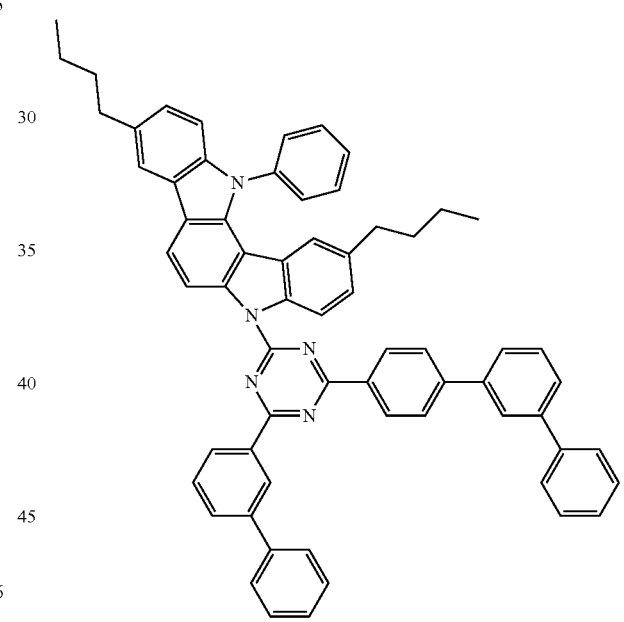
1-49
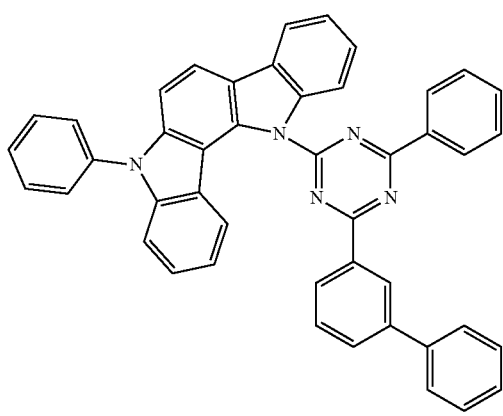

1-50
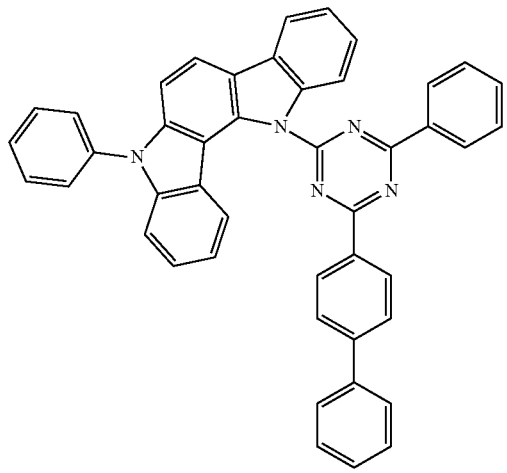
1-51
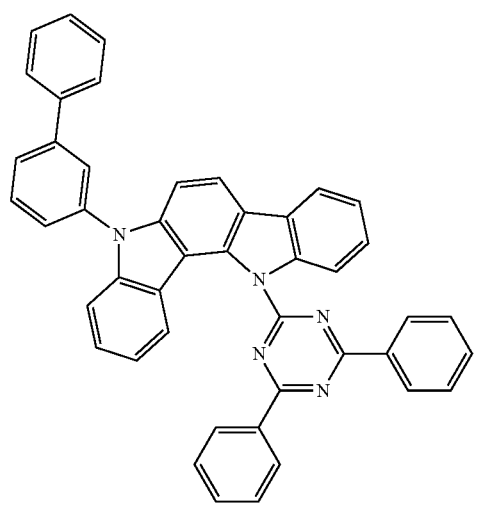
1-52
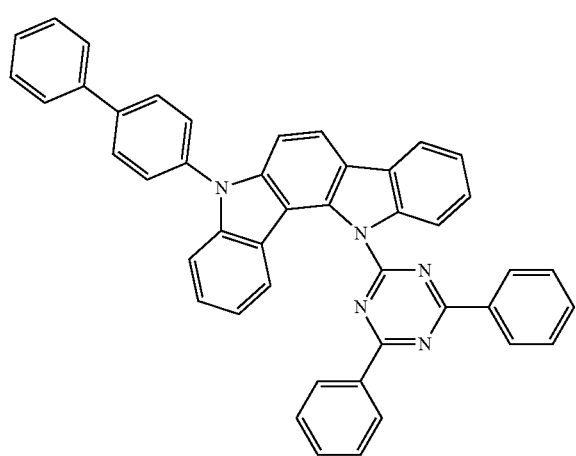
1-53
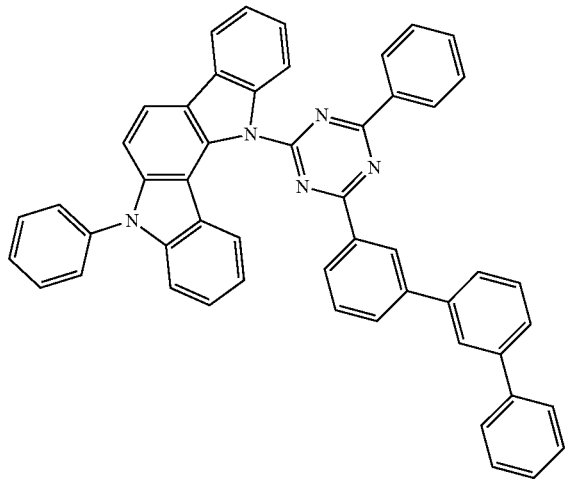
1-54
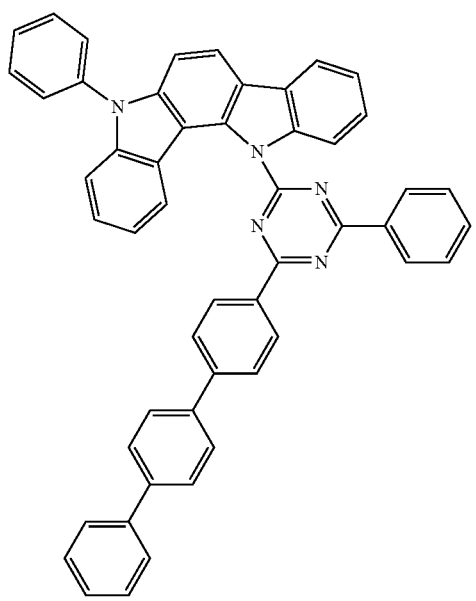
1-55
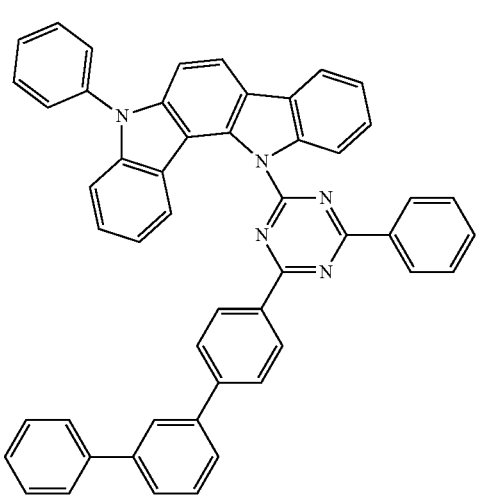

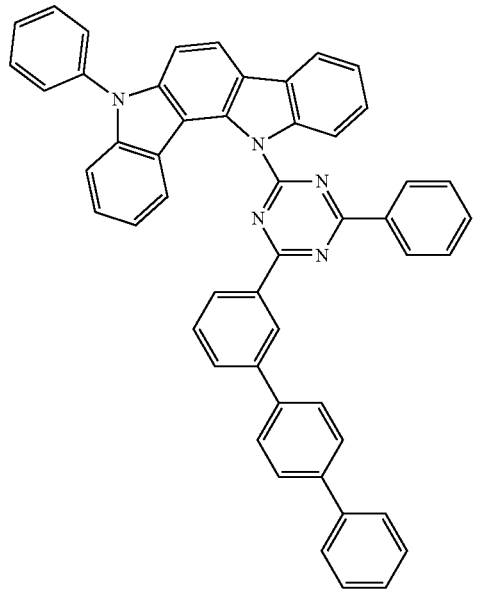
1-56
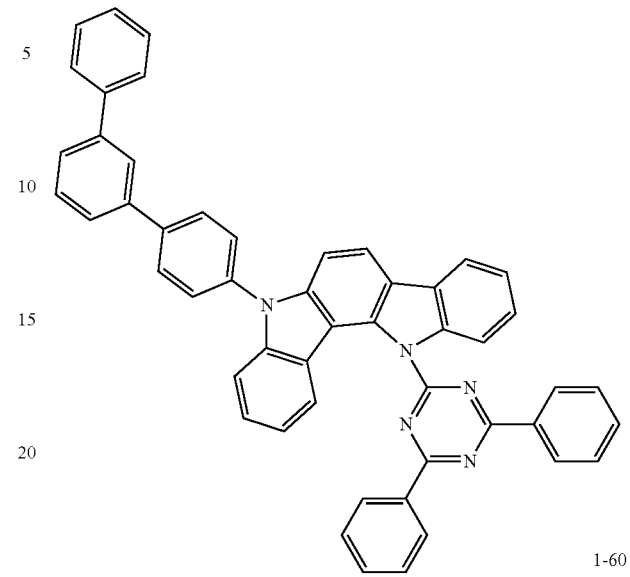
1-59
1-57
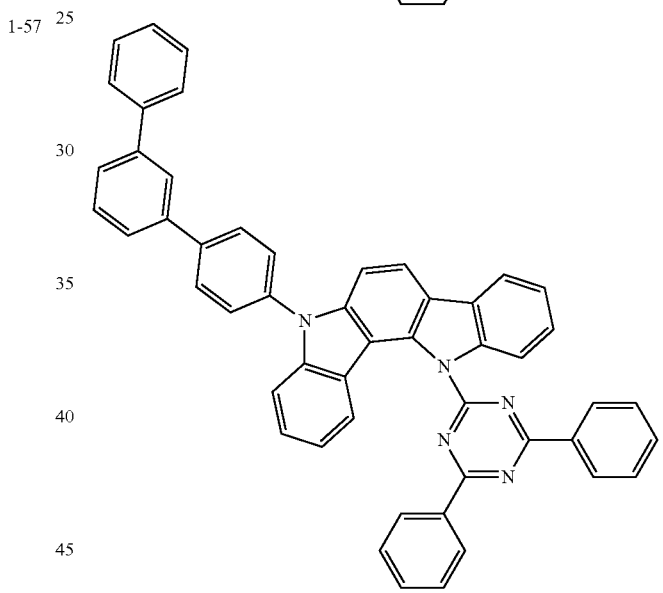
1-60
[C10]
1-58
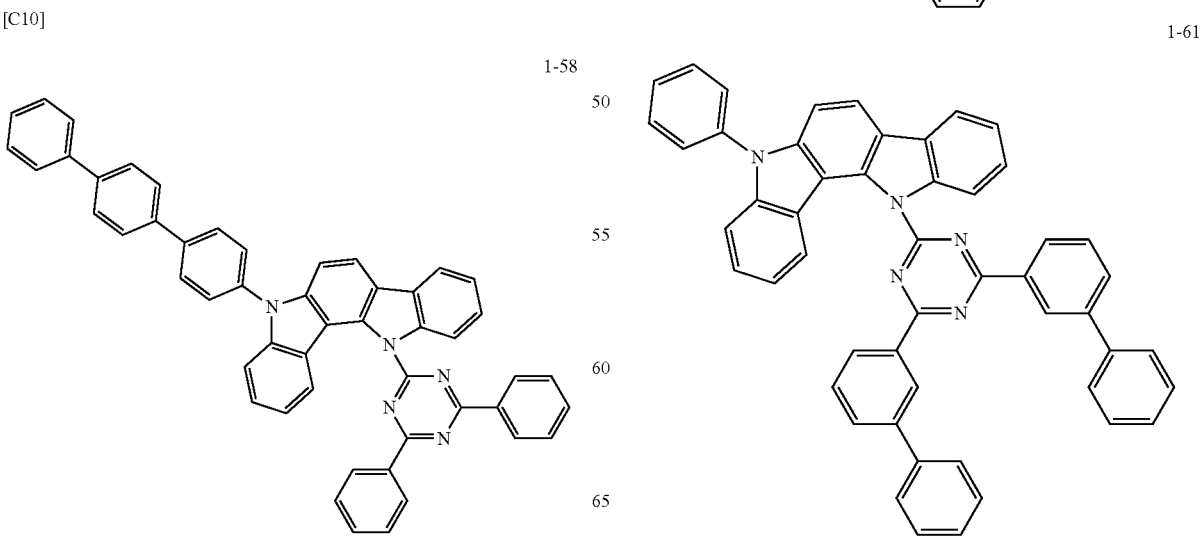
1-61

1-62
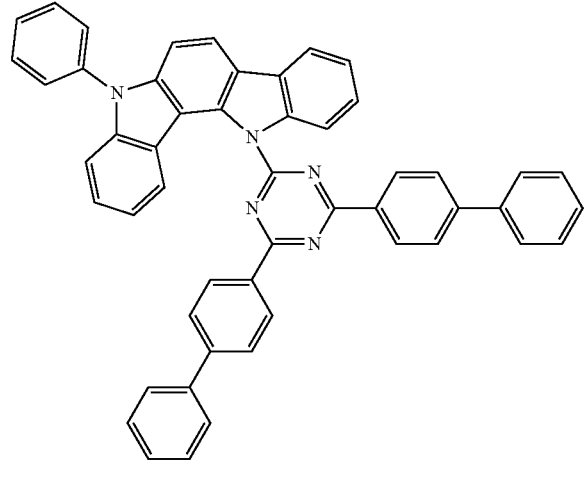
1-65
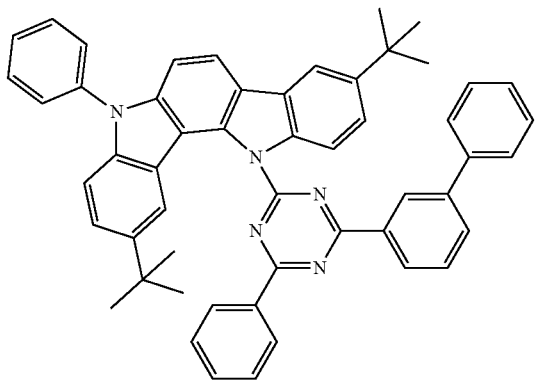
1-66
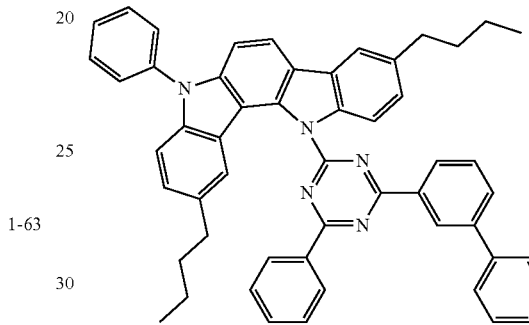
1-63
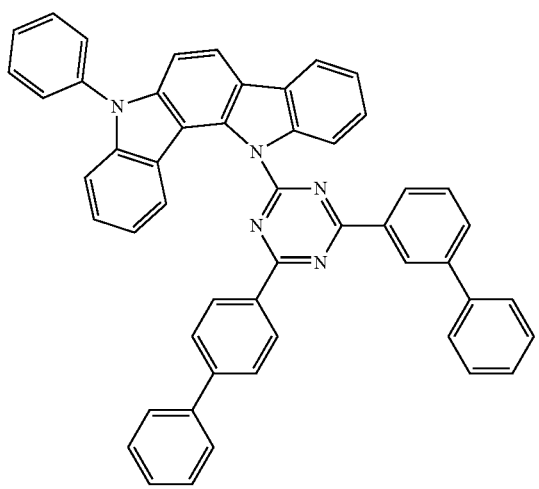
1-67
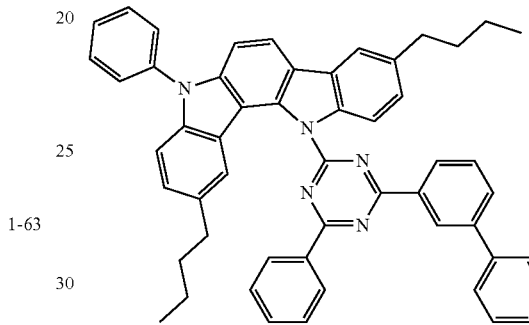
1-64
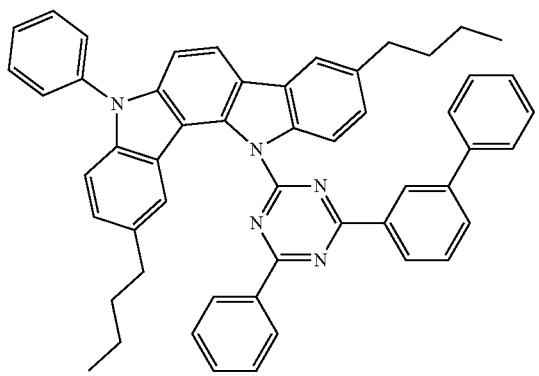
1-68
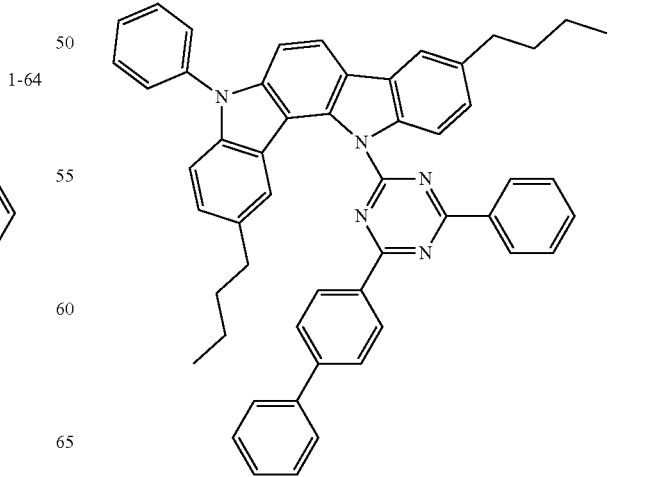

1-69
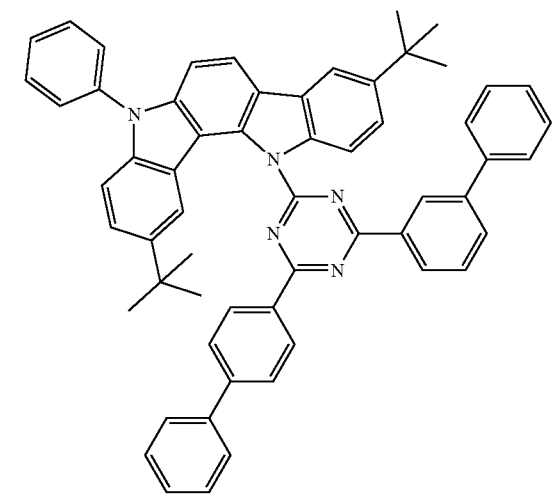
[C11]
1-70
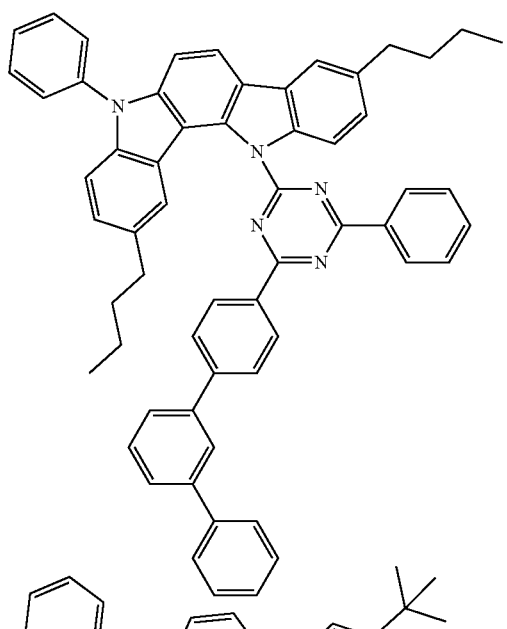
1-71
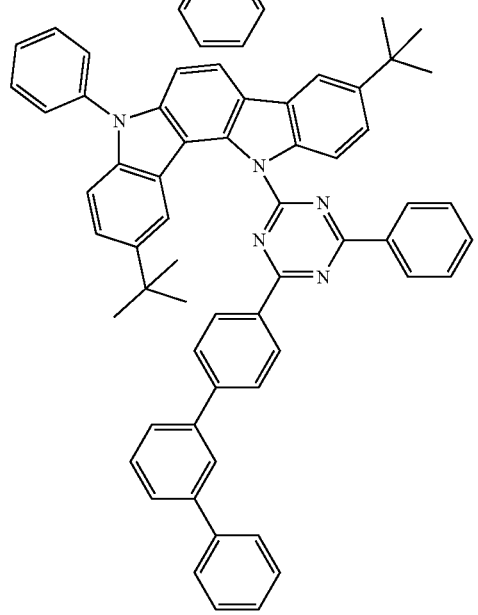
1-72
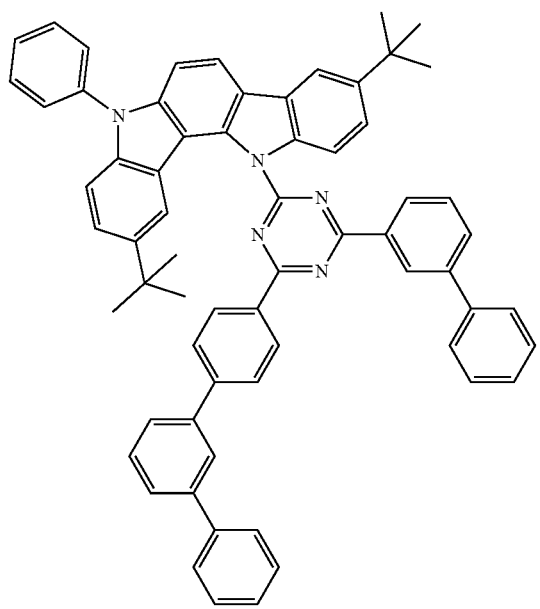
1-73
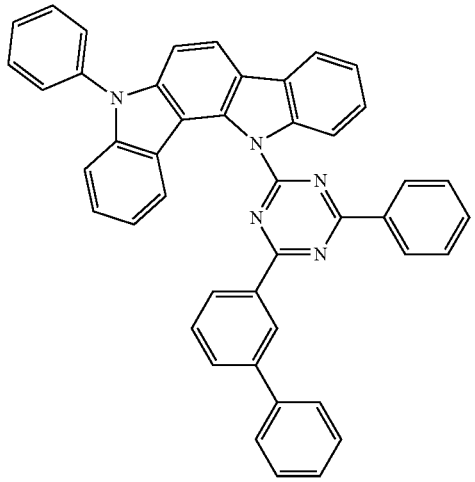
1-74
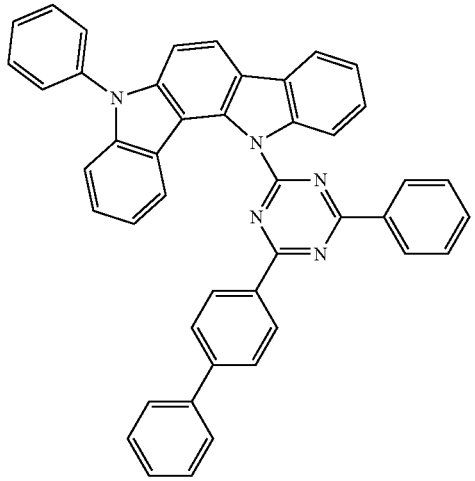

1-75
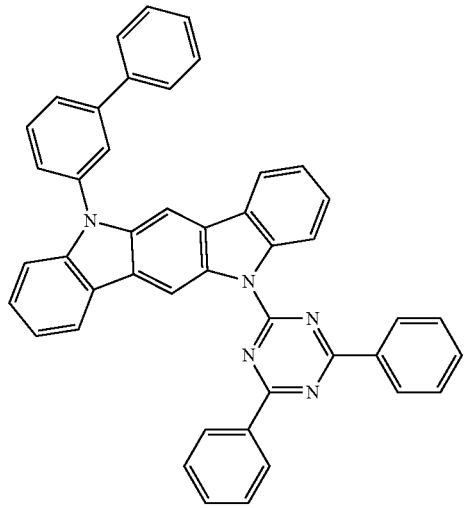
1-78
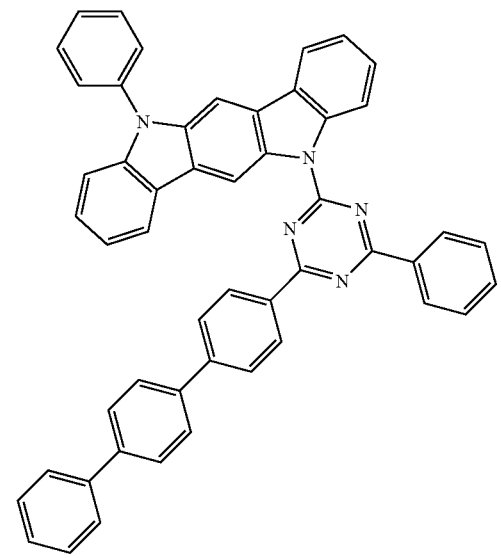
1-76
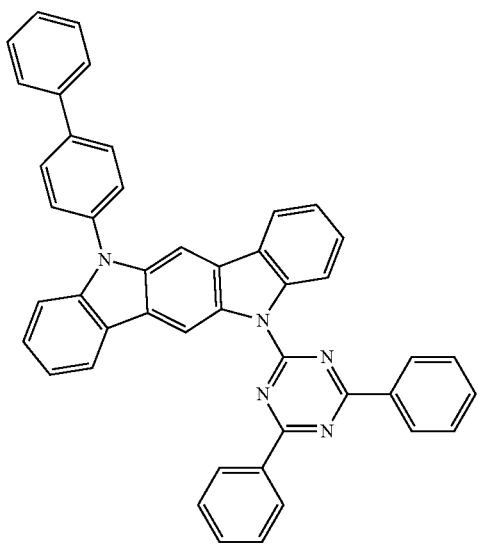
1-79
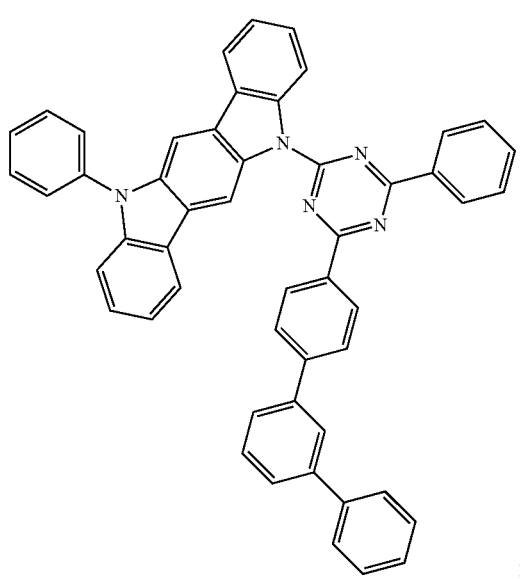
1-77
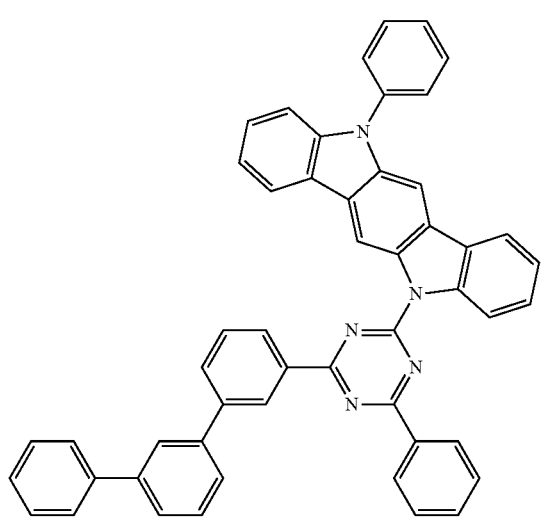
1-80
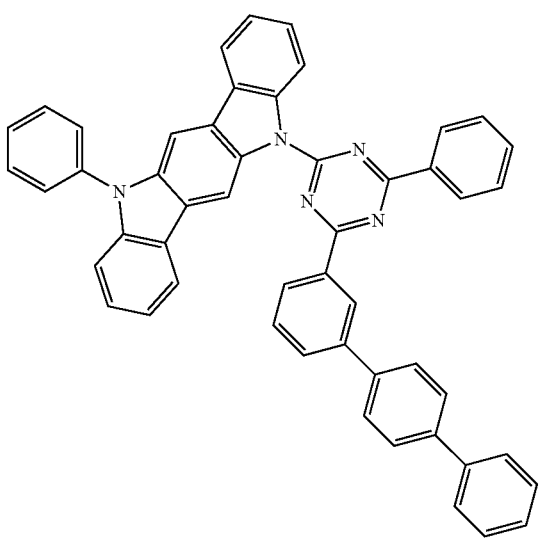

1-81
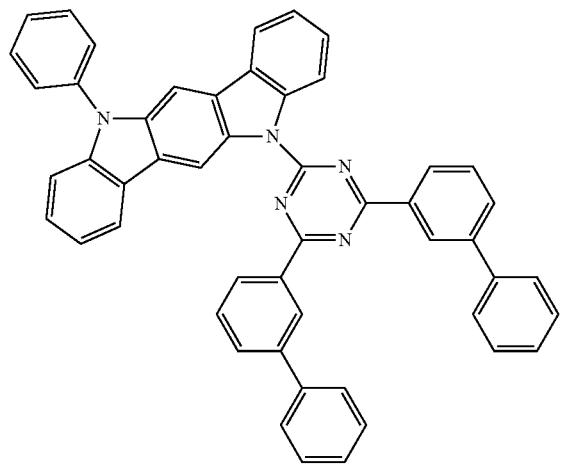
[C12]
1-82
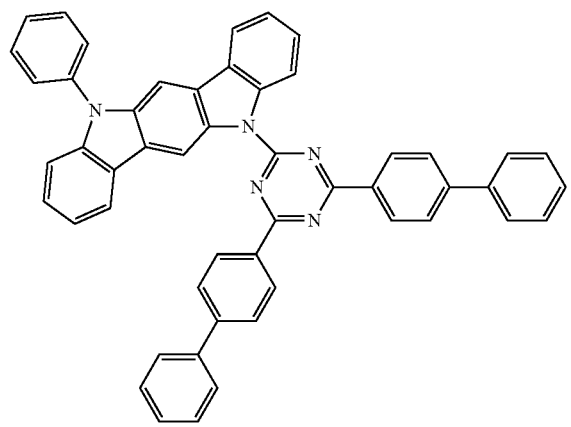
1-83
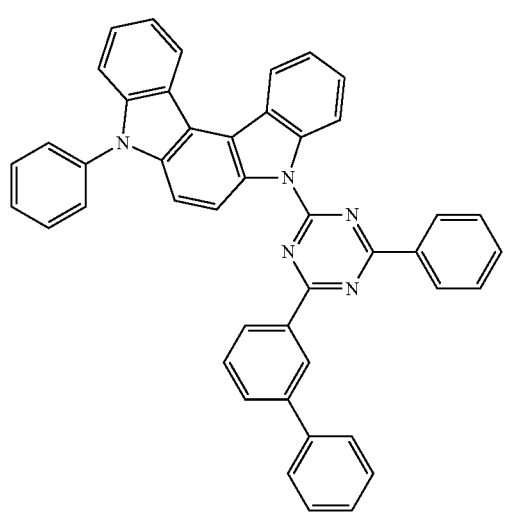
1-84
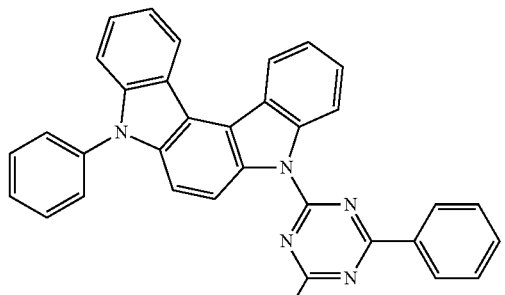
1-85
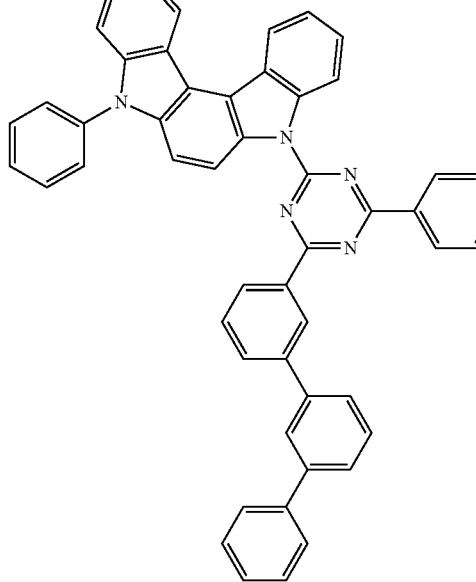
1-86

1-87
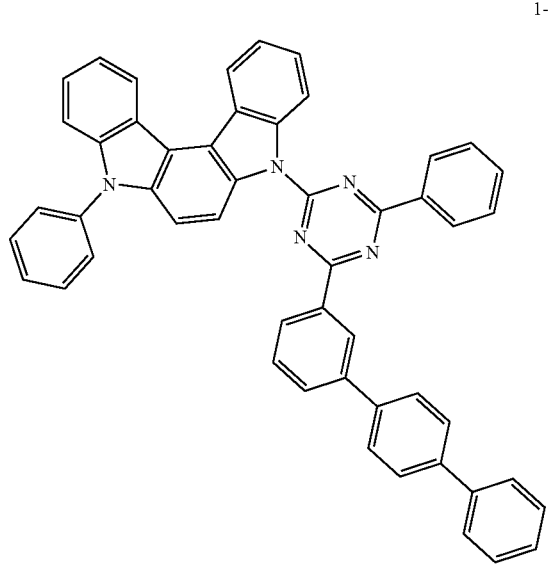
1-90
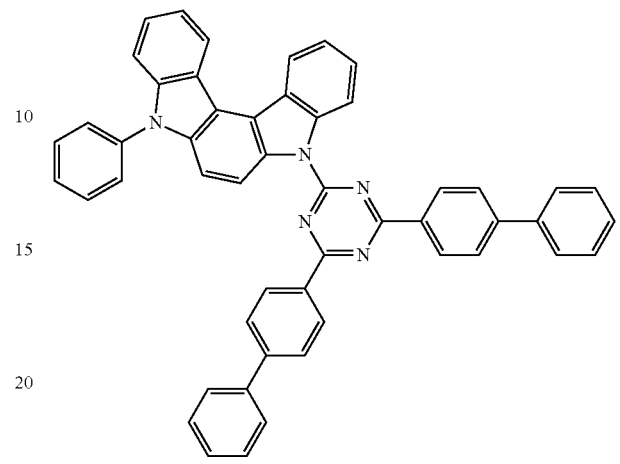
1-88
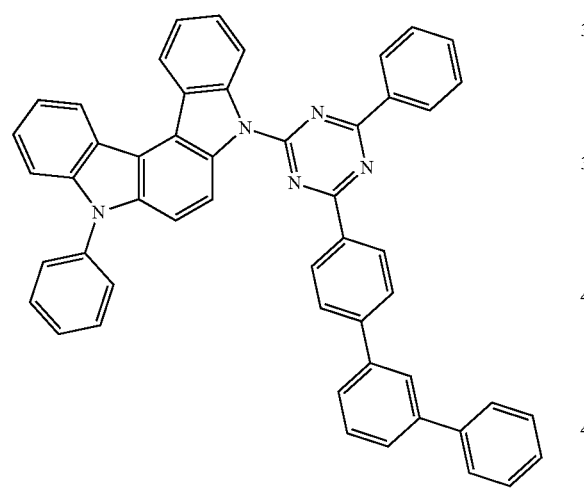
1-91
1-89
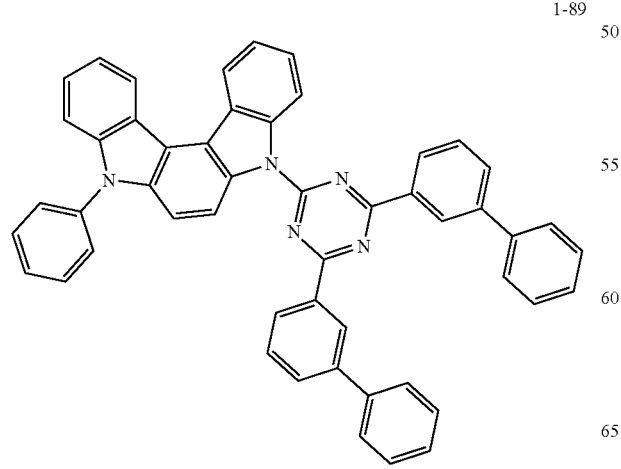
1-92
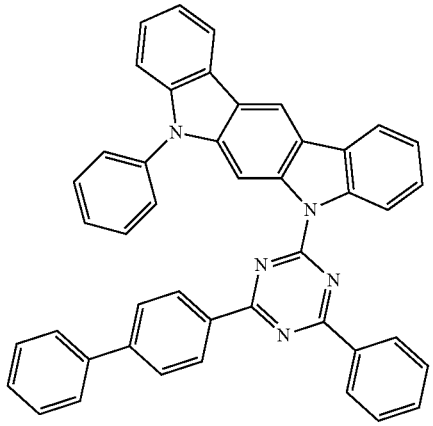

-continued
1-93
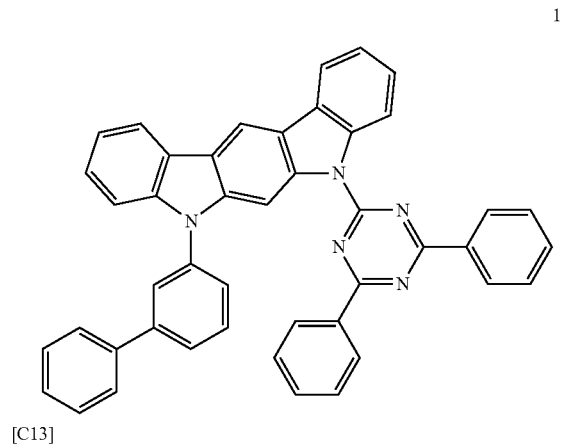
[C13]
1-94
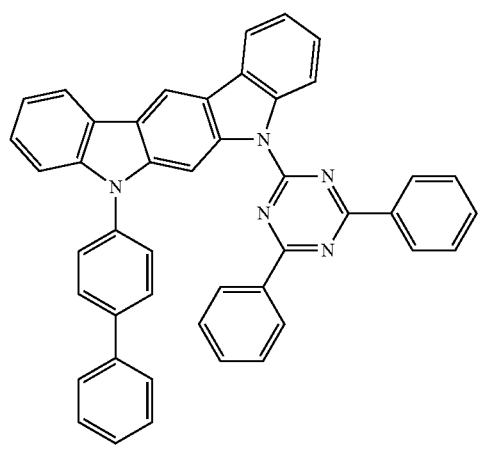
1-95
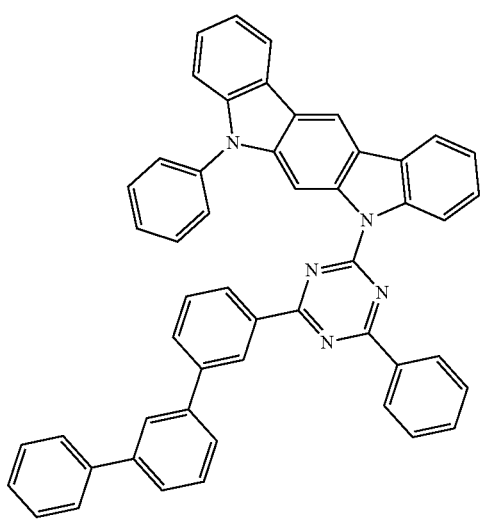
-continued
1-96
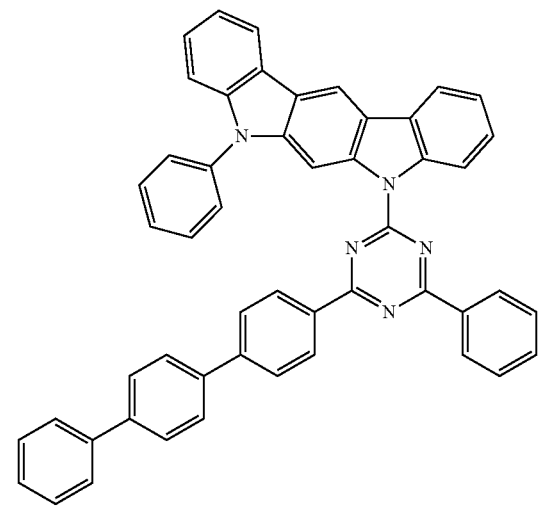
1-97
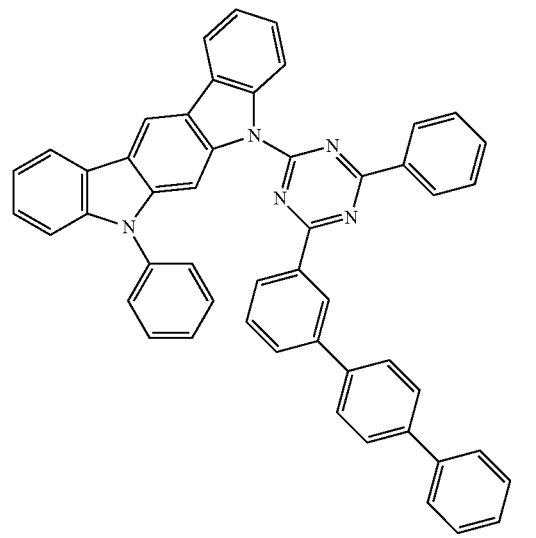
1-98
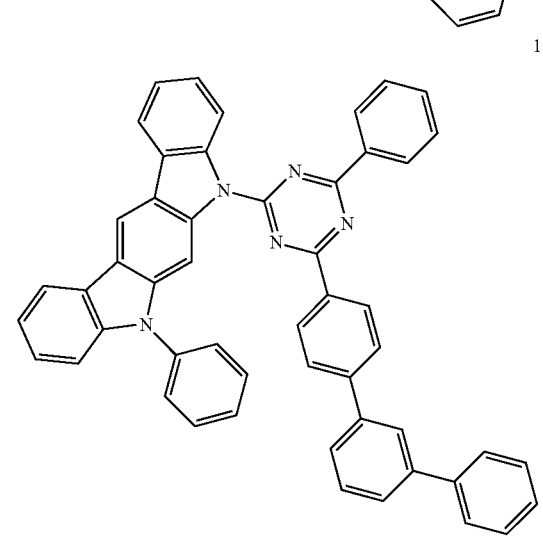

1-99
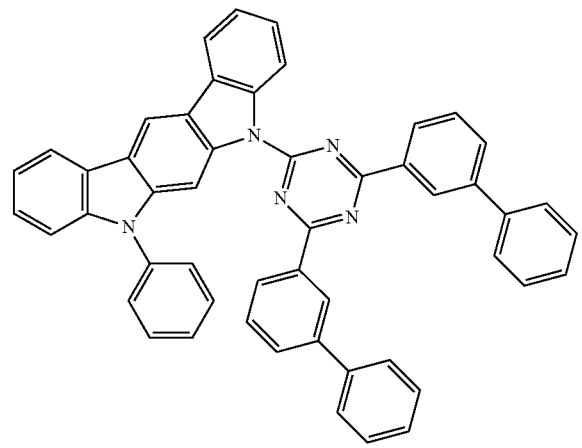
1-100
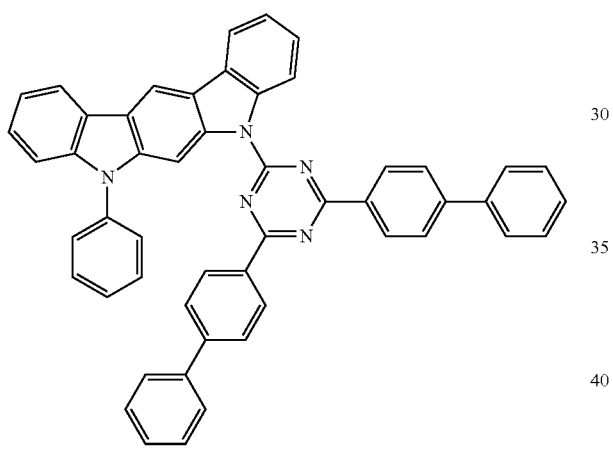
1-101
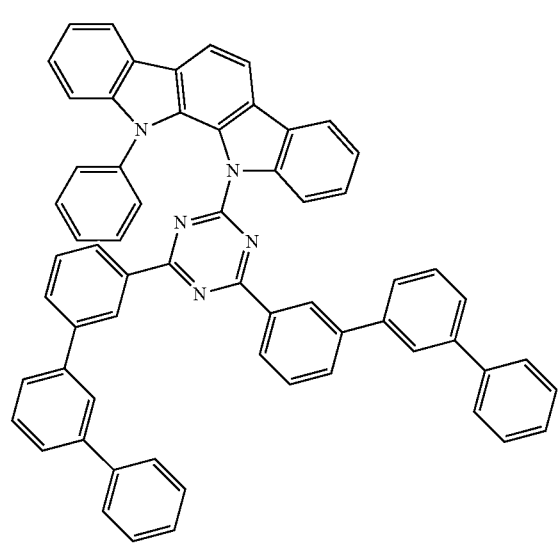
1-102
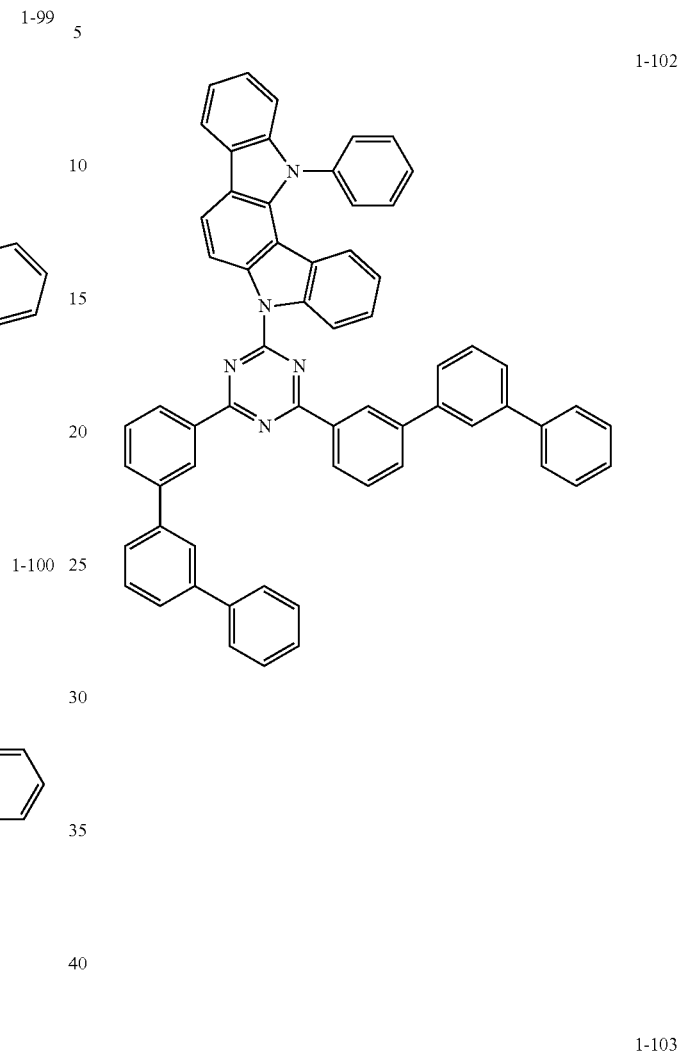
1-103
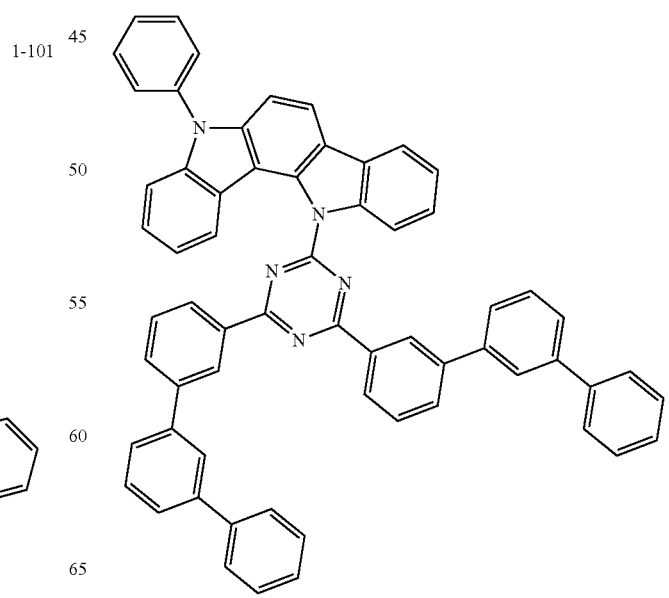

1-104
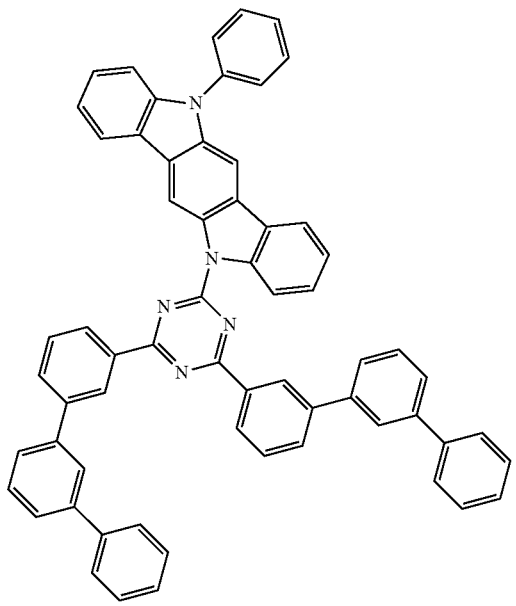
1-105
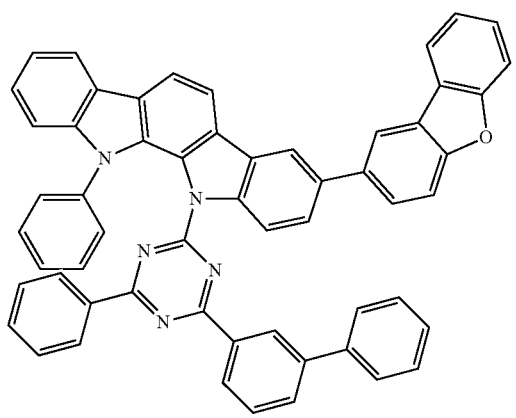
[C14]
1-106
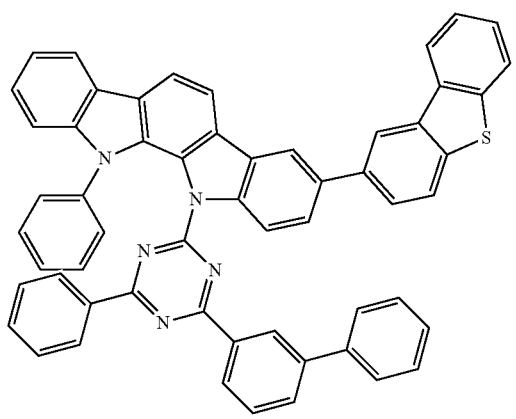
1-107
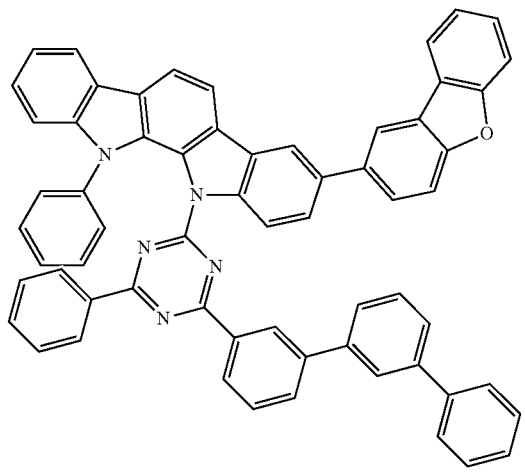
1-108
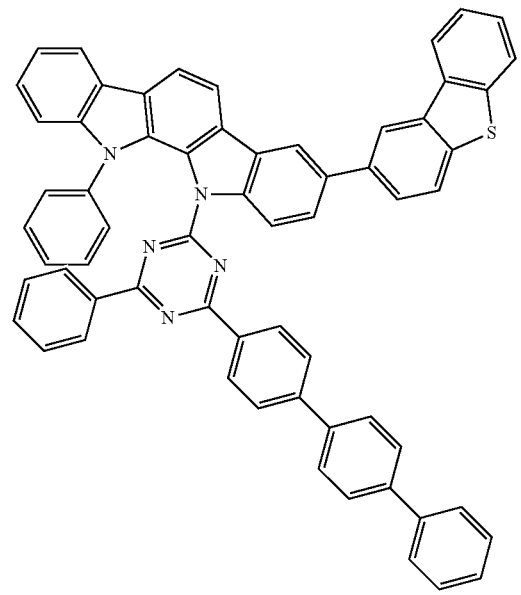
1-109
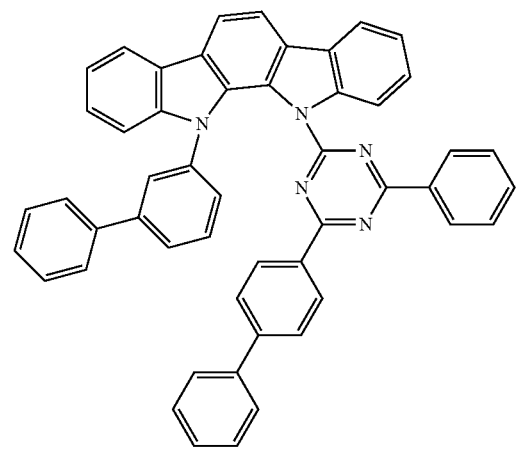

1-110
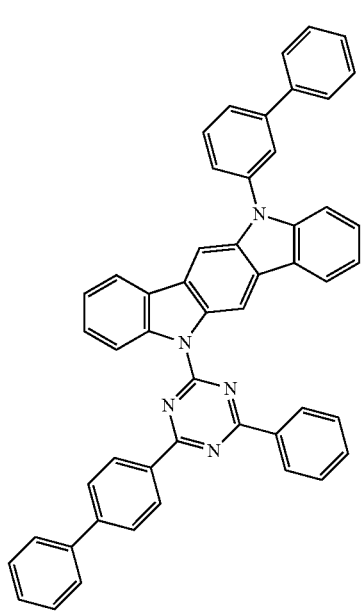
1-111
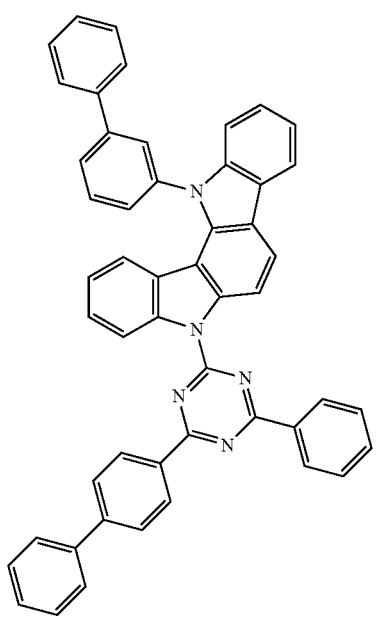
1-112
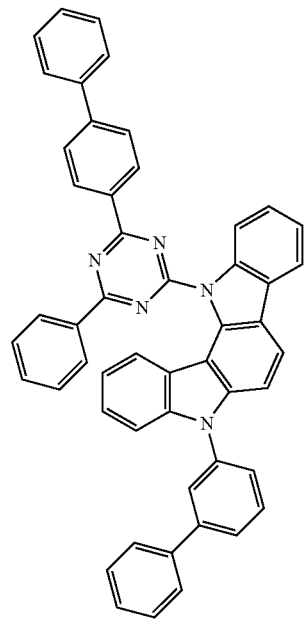
1-113
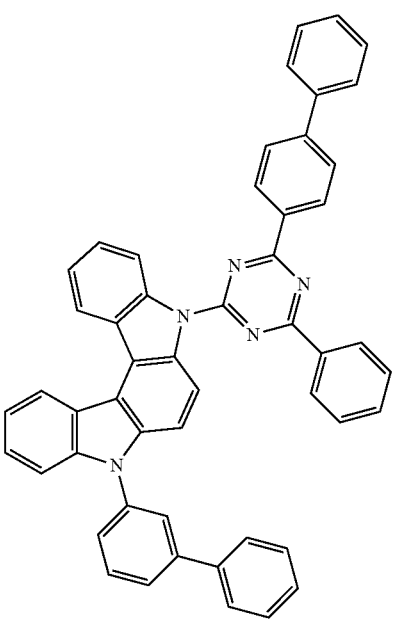

1-114

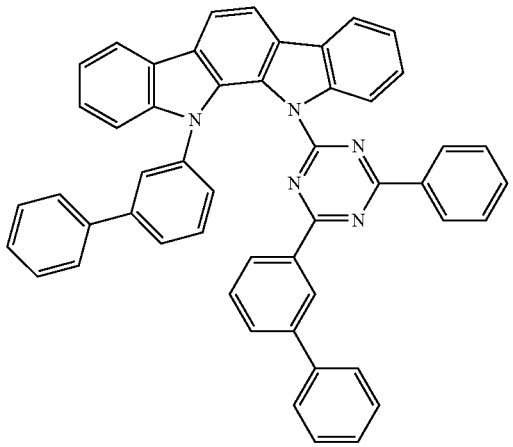

[C15]

1-115

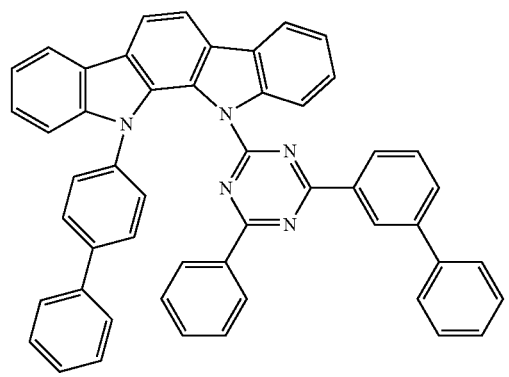

1-116

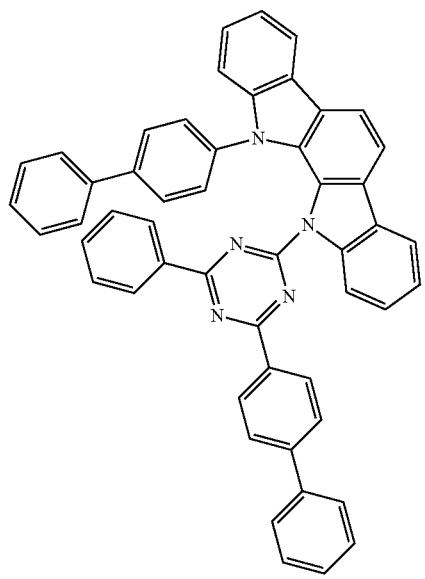

1-117

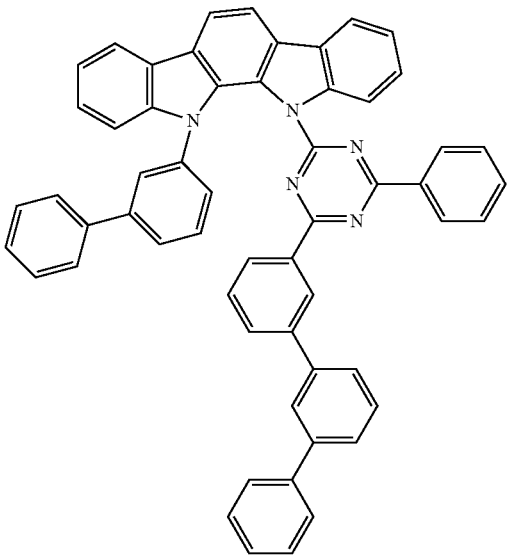

Next, formula (2) representing the second host and formulae (3) to (5) which represent preferable embodiments thereof will be described. In formulae (2) to (5), the same symbols have the same meanings.

$Ar^2$ and $Ar^3$ independently represent a hydrogen atom, an aromatic hydrocarbon group having 6 to 14 carbon atoms, or a group in which two of the aromatic hydrocarbon groups are linked (referred to as a linked aromatic group). Preferable examples thereof include a hydrogen atom and an aromatic hydrocarbon group having 6 to 12 carbon atoms, and more preferable examples thereof include an aromatic hydrocarbon group having 6 to 10 carbon atoms. In a preferable embodiment, $Ar^2$ is a hydrogen atom or $Ar^2$ is a hydrogen atom, and $Ar^3$ is the above aromatic hydrocarbon group or linked aromatic group. However, $Ar^2$ and $Ar^3$ are not both a hydrogen atom.

Specific examples of $Ar^2$ and $Ar^3$ include a hydrogen atom, an aromatic hydrocarbon such as benzene, naphthalene, anthracene, phenanthrene, and fluorene, an aromatic group formed by taking one H from a compound in which two aromatic rings of such aromatic hydrocarbons are linked and a linked aromatic group. Preferable examples thereof include an aromatic group generated from benzene, naphthalene, anthracene, or phenanthrene, and a linked aromatic group in which two of these aromatic groups are linked, and more preferable examples thereof include an aromatic group generated from benzene, naphthalene, or phenanthrene. $Ar^3$ is more preferably a phenyl group. One of $Ar^2$ and $Ar^3$ may be a hydrogen atom, and in this case, the other is the above aromatic group or linked aromatic group. More preferably, $Ar^2$ is a hydrogen atom and $Ar^3$ is a phenyl group. In addition, the above aromatic group or linked aromatic group may have a substituent, and a preferable substituent is an alkyl group having 1 to 12 carbon atoms or an alkoxy group having 1 to 12 carbon atoms.

Here, the linked aromatic group is represented by, for example, a formula of —$Ar^4$—$Ar^5$. Here, $Ar^4$ and $Ar^5$ independently represent an aromatic hydrocarbon group having 6 to 14 carbon atoms. $Ar^4$ is a divalent or trivalent group, and $Ar^5$ is a monovalent group. Aromatic groups constituting the linked aromatic group may be the same as or different from each other.

$L^1$ and $L^2$ are a phenylene group, and the phenylene group is a p-phenylene group or an m-phenylene group. The p-phenylene group and the m-phenylene group are represented by formula (2a) and formula (2b), respectively. Thus, when one $Ar^2$ or $Ar^3$ is a hydrogen atom, the other -$L^1$-$Ar^2$ or -$L^2$-$Ar^3$ may be an m-phenylene group or a p-phenylene group in which an aromatic hydrocarbon group is substituted.

Preferably, $L^1$ is a phenylene group represented by formula (2a), $L^2$ is a phenylene group represented by formula (2b), $Ar^2$ is a hydrogen atom, -$L^1$-$Ar^2$ is a phenyl group, and $L^2$ is an m-phenylene group or a p-phenylene group. In another aspect, it is preferable that $L^1$=$L^2$ not be satisfied except for a case in which $Ar^2$ or $Ar^3$ is a hydrogen atom. That is, $L^1$ and $L^2$ are not both p-phenylene groups, and not both m-phenylene groups. For example, when one is a p-phenylene group, the other is an m-phenylene group. When one $Ar^2$ or $Ar^3$ is a hydrogen atom, a case in which $L^1$=$L^2$ is satisfied is excluded because a substitution position for $L^1$ or $L^2$ is an arbitrary phenylene group.

Specific examples of compounds represented by formulae (2) to (5) are shown below, but the present invention is not limited to such exemplary compounds.

[C16]

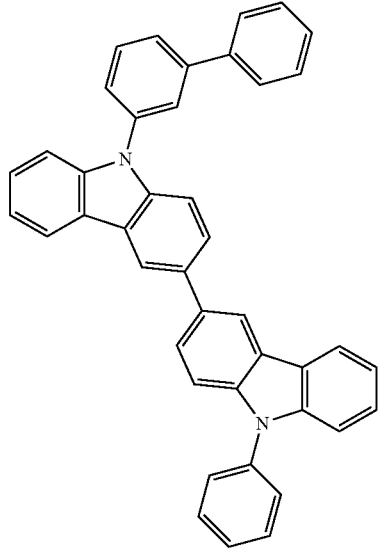

2-1

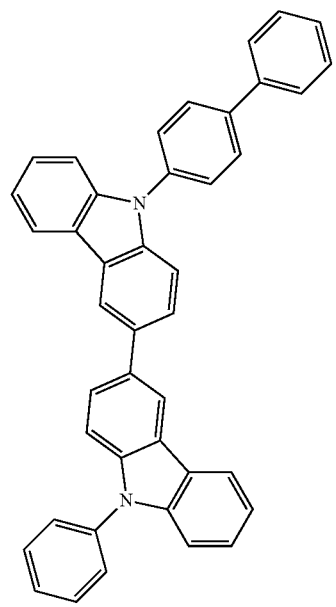

2-2

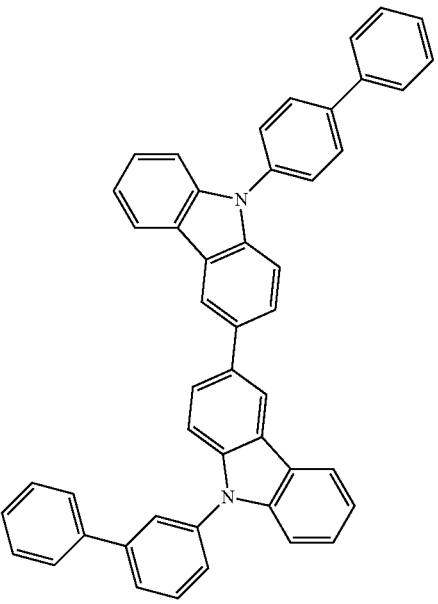

2-3

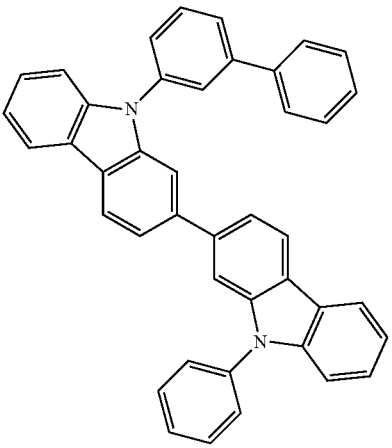

2-4

2-5
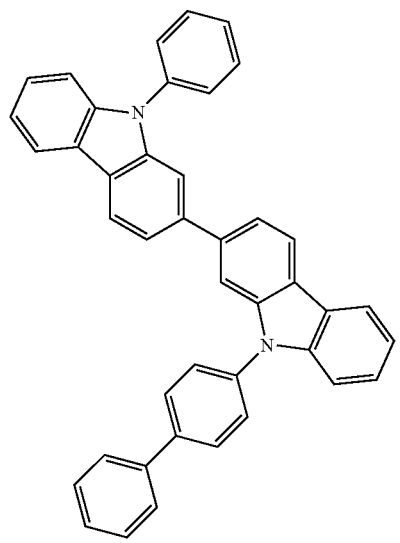
2-6
2-7
2-8
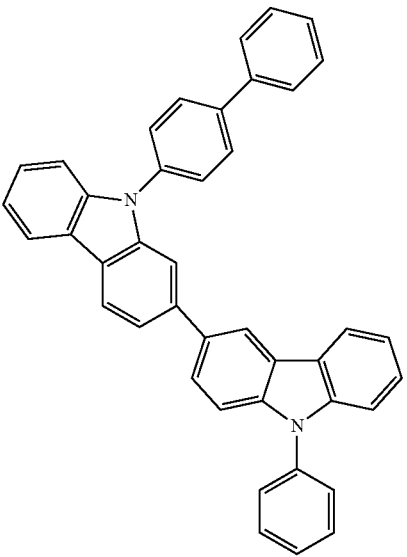
2-9
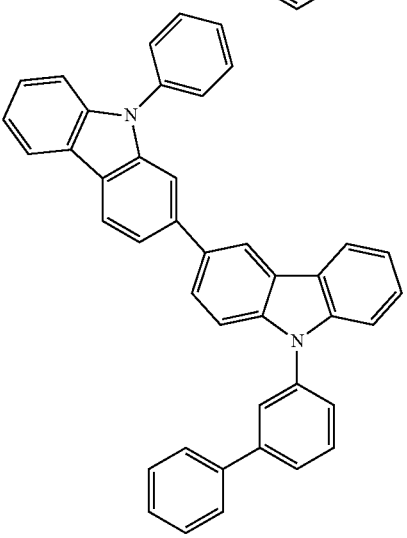
2-10
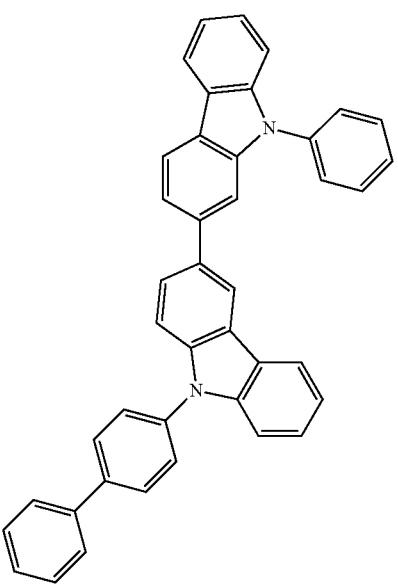

2-11
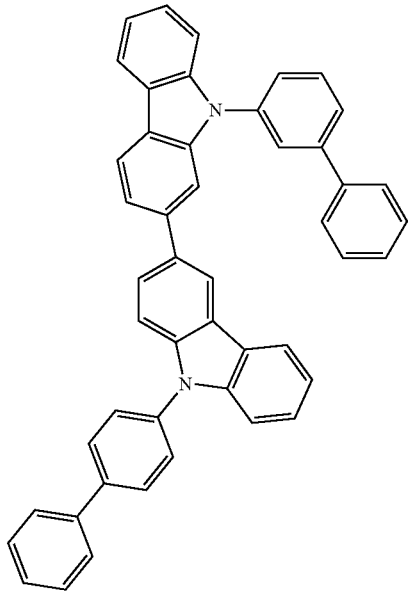
2-12
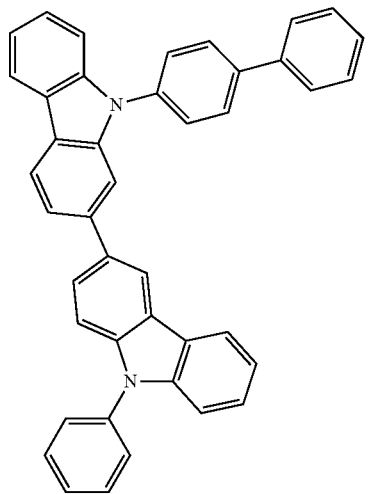
2-13
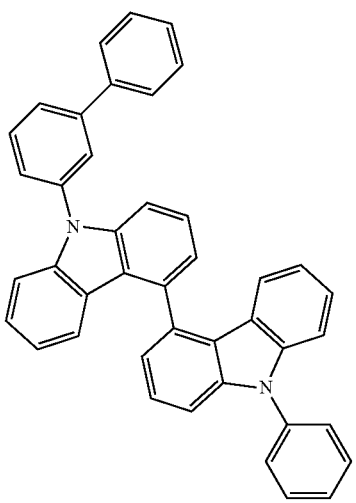
2-14
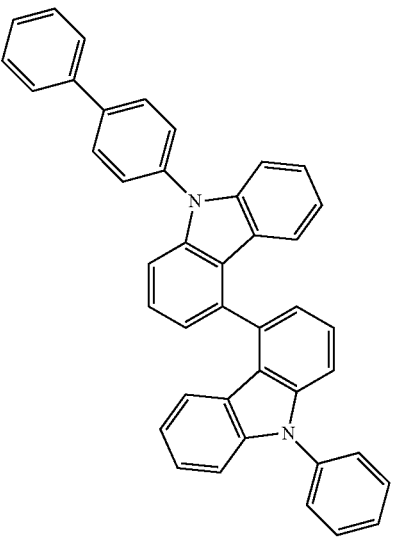
2-15
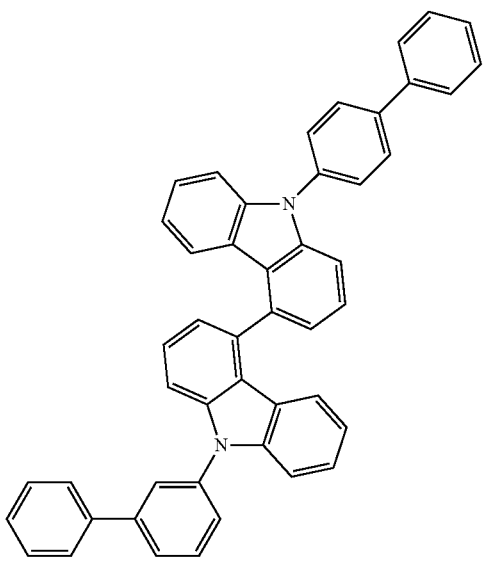
2-16
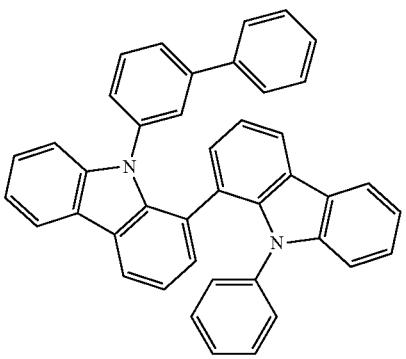

2-17
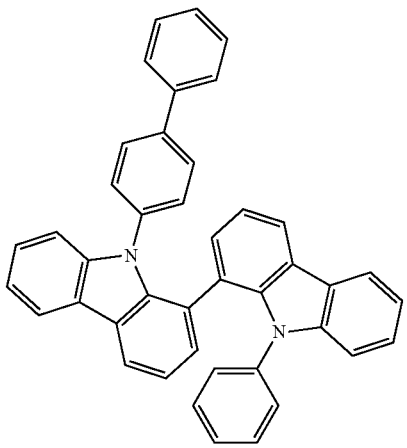
2-18
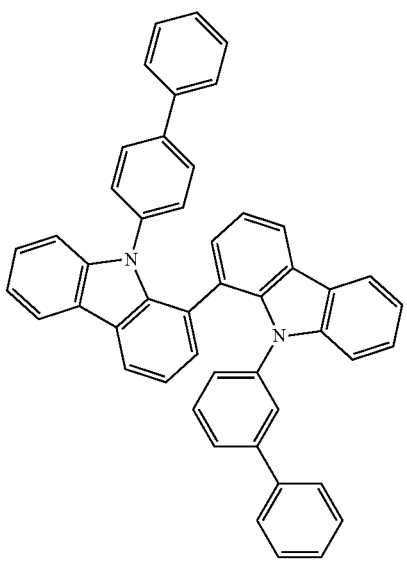
[C18]
2-19
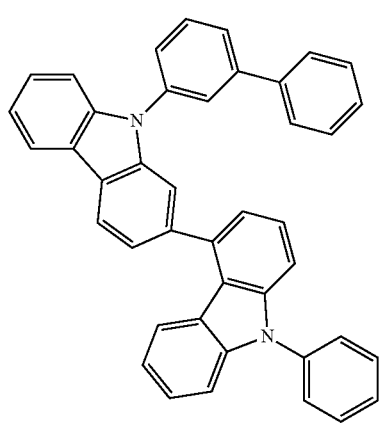
2-20
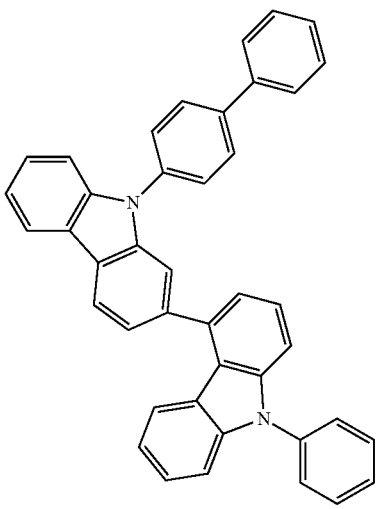
2-21
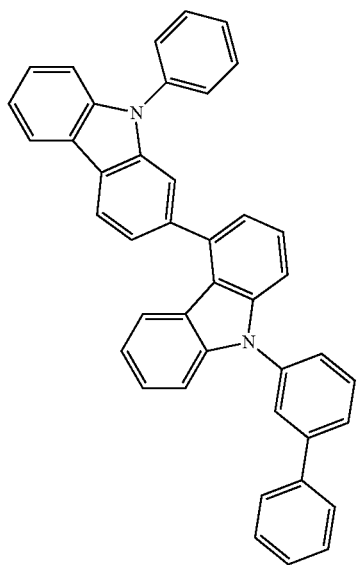
2-22
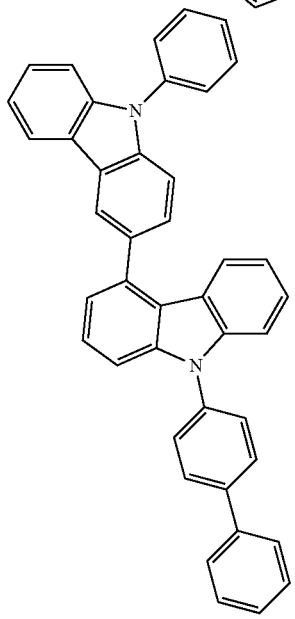

2-23
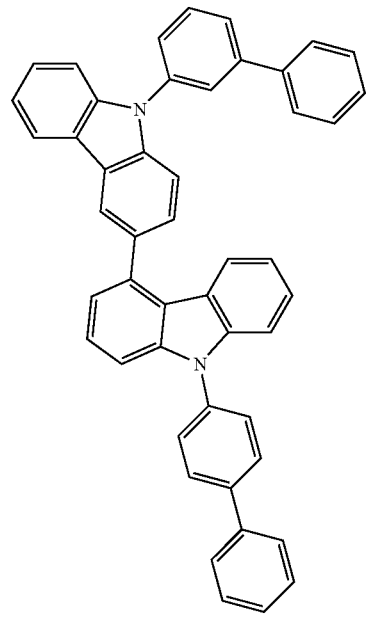
2-24
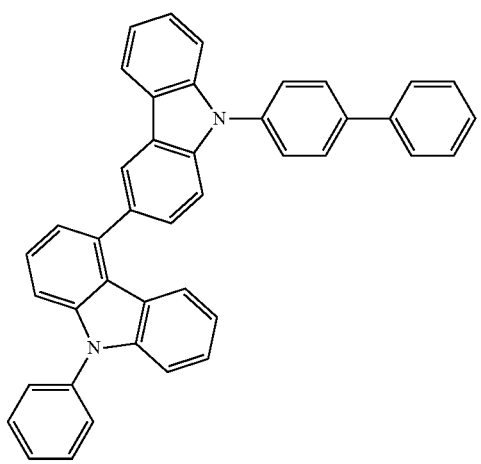
2-25
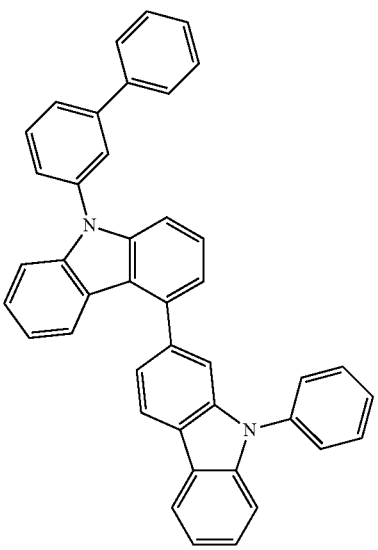
2-26
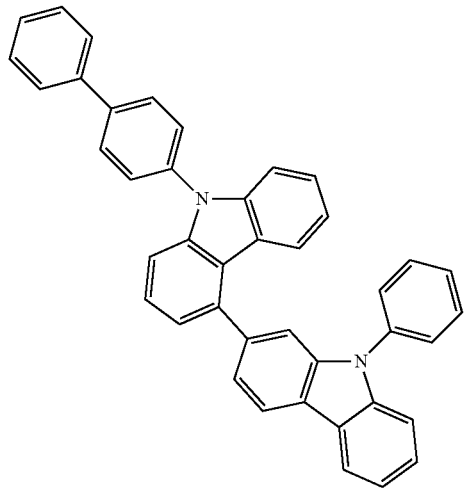
2-27
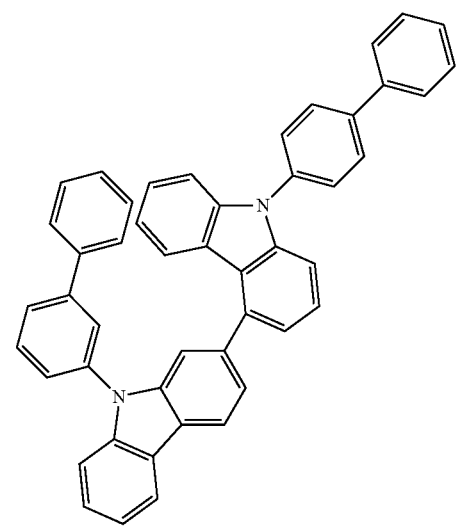
[C19]
2-28
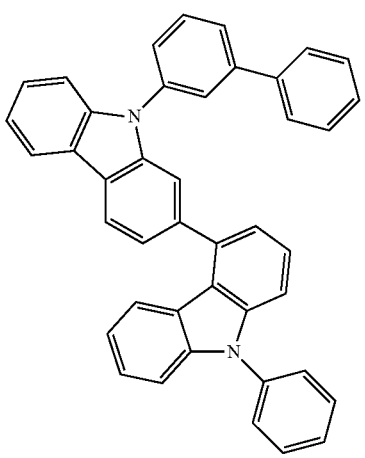

2-29
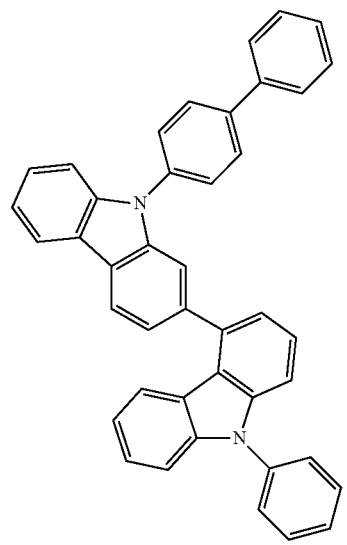
2-30
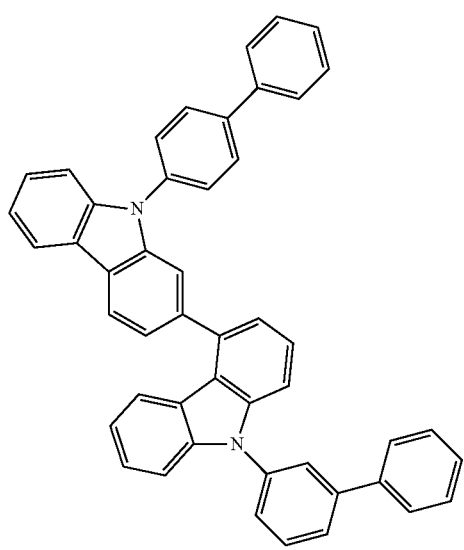
2-31
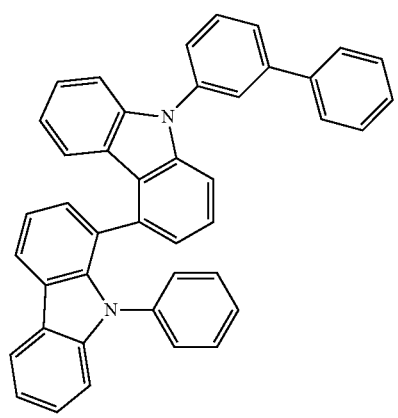
2-32
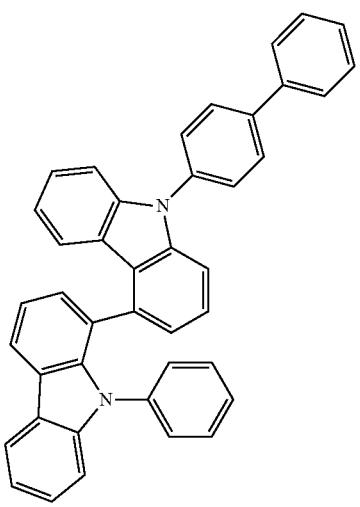
2-33
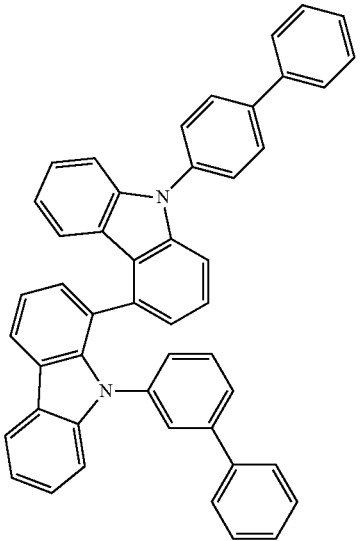
2-34
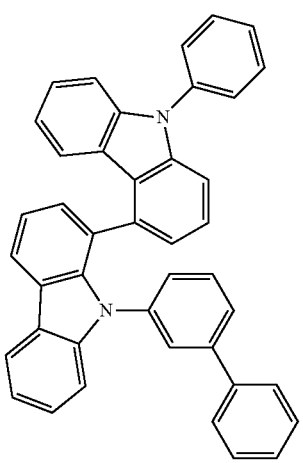

2-35
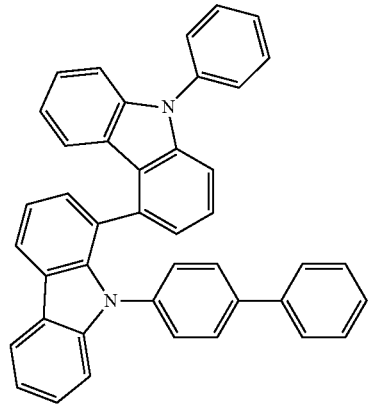
2-36
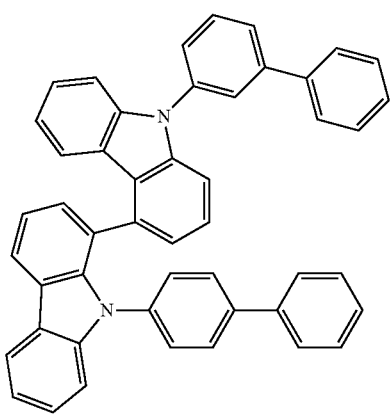
[C20]
2-37
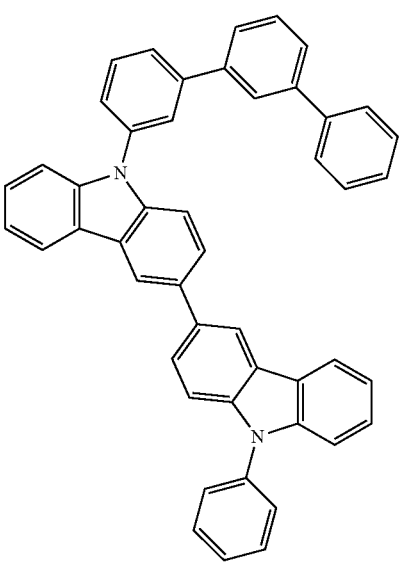
2-38
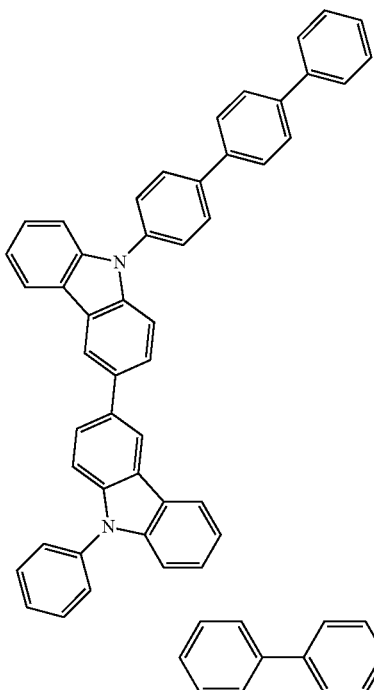
2-39
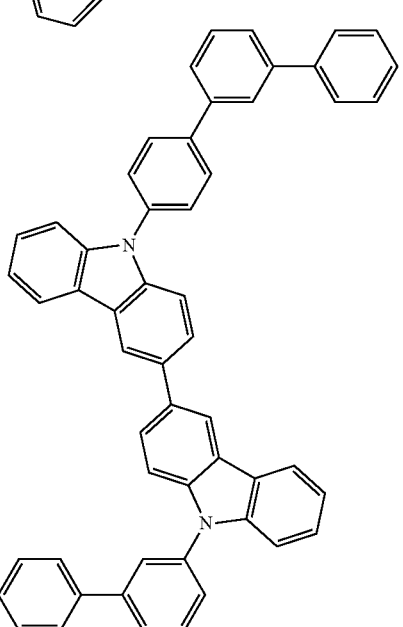
2-40
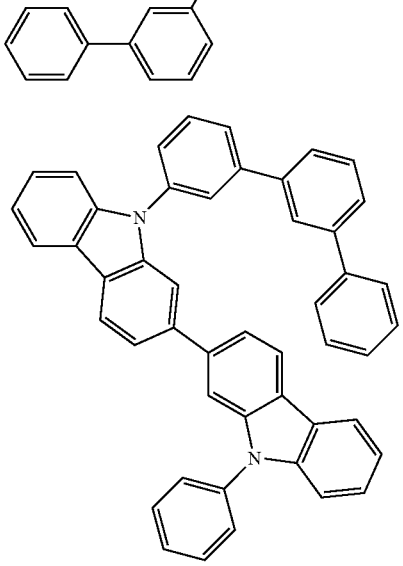

2-41 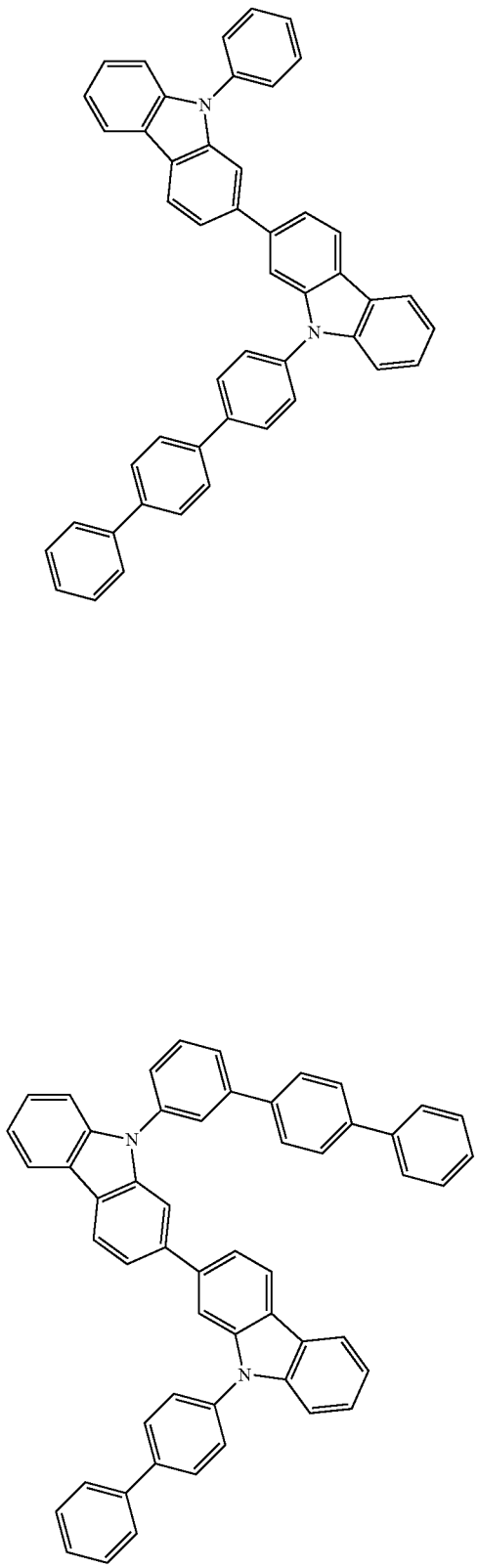

2-42

2-43 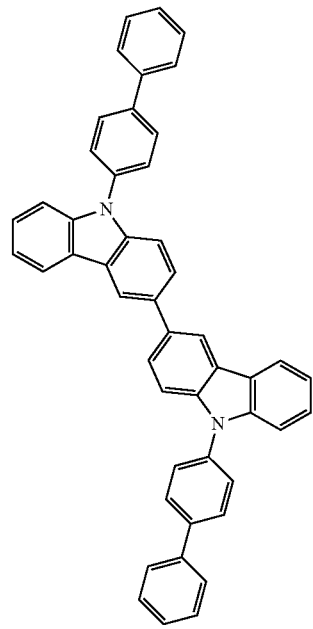

2-44 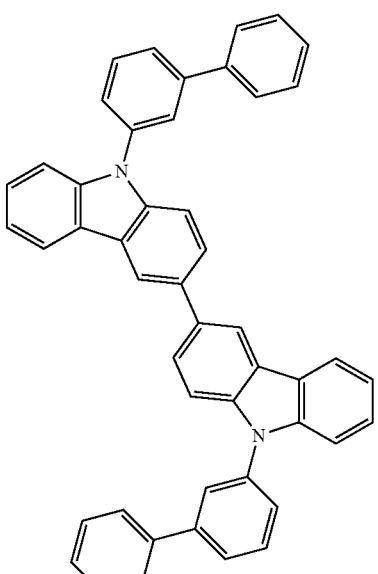

It is possible to provide an excellent organic EL element using the first host selected from among compounds represented by formula (1) and the second host selected from among compounds represented by formula (2) as host materials of a light-emitting layer.

The first host and the second host which are vapor-deposited from different vapor deposition sources can be used. However, preferably, they are mixed in advance before vapor deposition to prepare a pre-mixture, and the pre-mixture is vapor-deposited from one vapor deposition source at the same time to form a light-emitting layer. In this case, a light-emitting dopant material necessary for forming a light-emitting layer or another host used as necessary may be mixed into the pre-mixture. However, when there is a large difference in temperature at which a desired vapor pressure is obtained, vapor deposition may be performed from another vapor deposition source.

In addition, regarding the mixing ratio (weight ratio) between the first host and the second host, a proportion of the first host is 20% to 60%, preferably more than 20% and less than 55%, and more preferably 40% to 50% with respect to a total amount of the first host and the second host.

Next, the structure of the organic EL element of the present invention will be described with reference to the drawing, but the structure of the organic EL element of the present invention is not limited thereto.

FIG. 1 is a cross-sectional view showing a structure example of an organic EL element generally used for the present invention. 1 indicates a substrate, 2 indicates an anode, 3 indicates a hole injection layer, 4 indicates a hole transport layer, 5 indicates a light-emitting layer, 6 indicates an electron transport layer, and 7 indicates a cathode. The organic EL element of the present invention may have an exciton blocking layer adjacent to the light-emitting layer and may have an electron blocking layer between the light-emitting layer and the hole injection layer. The exciton blocking layer can be inserted into either on the side of the cathode or the cathode of the light-emitting layer and inserted into both sides at the same time. The organic EL element of the present invention has the anode, the light-emitting layer, and the cathode as essential layers, and may have a hole injection transport layer and an electron injection transport layer in addition to the essential layers, and may have additionally a hole blocking layer between the light-emitting layer and the electron injection transport layer. Here, the hole injection transport layer refers to either or both of the hole injection layer and the hole transport layer, and the electron injection transport layer refers to either or both of the electron injection layer and the electron transport layer.

A structure reverse to that of FIG. 1, that is, a structure in which a cathode 7, an electron transport layer 6, a light-emitting layer 5, a hole transport layer 4, and an anode 2 are laminated on a substrate 1 in this order, can be used, and in this case also, layers can be added or omitted as necessary.

—Substrate—

The organic EL element of the present invention is preferably supported on a substrate. The substrate is not particularly limited, and those used in the organic EL element in the related art may be used, and those made of, for example, glass, a transparent plastic, or quartz, can be used.

—Anode—

Regarding an anode material for an organic EL element, a material of a metal having a large work function (4 eV or more), an alloy, an electrically conductive compound or a mixture thereof is preferably used. Specific examples of such an electrode material include a metal such as Au, and a conductive transparent material such as CuI, indium tin oxide (ITO), $SnO_2$, and ZnO. In addition, an amorphous material such as IDIXO ($In_2O_3$—ZnO) which can form a transparent conductive film may be used. Regarding the anode, such an electrode material is used to form a thin film by a vapor-deposition or sputtering method, and a desired shape pattern may be formed by a photolithographic method, or if the pattern accuracy is not particularly required (about 100 μm or more), a pattern may be formed via a desired shape mask when the electrode material is vapor-deposited or sputtered. Alternatively, when a coatable substance such as the organic conductive compound is used, a wet film formation method such as a printing method and a coating method can be used. When light is emitted from the anode, it is desirable that the transmittance be larger than 10% and sheet resistance for the anode is preferably several hundreds Ω/sq or less. The film thickness depends on the material, and it is generally 10 to 1,000 nm, and preferably selected in a range of 10 to 200 nm.

—Cathode—

On the other hand, regarding a cathode material, a material of a metal having a small work function (4 eV or less) (an electron injection metal), an alloy, an electrically conductive compound, or a mixture thereof is used. Specific examples of such an electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among these, in consideration of electron injectability and durability with respect to oxidation and the like, a mixture of an electron injection metal and a second metal which is a stable metal having a larger work function value, for example, a magnesium/silver mixture, a magnesium/aluminum mixture, a magnesium/indium mixture, an aluminum/aluminum oxide mixture, a lithium/aluminum mixture, aluminum, and the like are suitable. The cathode can be produced by forming a thin film by a method such as vapor-depositing or sputtering of such a cathode material. In addition, sheet resistance for the cathode is preferably several hundreds Ω/sq or less, and the film thickness is generally 10 nm to 5 μm, and preferably selected in a range of 50 to 200 nm. Here, in order to transmit emitted light, if either the anode or the cathode of the organic EL element is transparent or translucent, light emission brightness is improved, which is advantageous.

In addition, after the metal with a film thickness of 1 to 20 nm is formed on the cathode, when a conductive transparent material exemplified in the description of the anode is formed thereon, a transparent or translucent cathode can be produced and by applying this, it is possible to produce an element in which both the anode and the cathode have transparency.

—Light-Emitting Layer—

The light-emitting layer is a layer that emits light after excitons are generated when holes and electrons injected from the anode and the cathode, respectively, are recombined. In the light-emitting layer, an organic light-emitting dopant material and a host material are included.

Regarding the host material in the light-emitting layer, the first host represented by formula (1) and the second host represented by formula (2) are used. In addition, one or more types of known host materials may be used in combination, and an amount used is 50 wt % or less, and preferably 25 wt % or less with respect to a total amount of host materials.

The first host and the second host are vapor-deposited from different vapor deposition sources. However, they are mixed in advance before vapor deposition to prepare a pre-mixture, and thus the first host and the second host can be vapor-deposited from one vapor deposition source at the same time.

When the first host and the second host are used by being mixed in advance, it is desirable that a difference in 50% weight reduction temperature ($T_{50}$) be small in order to produce an organic EL element having favorable characteristics with high reproducibility. The 50% weight reduction temperature is a temperature at which the weight is reduced by 50% when the temperature is raised to 550° C. from room temperature at a rate of 10° C./min in TG-DTA measurement under a nitrogen stream reduced pressure (50 Pa). Vaporization due to evaporation or sublimation is considered most likely to occur around this temperature.

The difference between 50% weight reduction temperatures of the first host and the second host is preferably within 20° C. and more preferably within 15° C. Regarding a premixing method, a known method such as pulverization and mixing can be used, and it is desirable to mix them as uniformly as possible.

When a phosphorescent dopant is used as the light-emitting dopant material, a phosphorescent dopant including an organic metal complex containing at least one metal selected from among ruthenium, rhodium, palladium, silver, rhenium, osmium, iridium, platinum, and gold may be used. Specifically, iridium complexes described in J. Am. Chem. Soc. 2001, 123, 4304 and Japanese Translation of PCT Application No. 2013-53051 are preferably used, but the present invention is not limited thereto.

Only one type of a phosphorescent dopant material may be contained in the light-emitting layer or two or more types thereof may be contained. A content of the phosphorescent dopant material is preferably 0.1 to 30 wt % and more preferably 1 to 20 wt % with respect to the host material.

The phosphorescent dopant material is not particularly limited, and specific examples thereof include the following.

[C21]

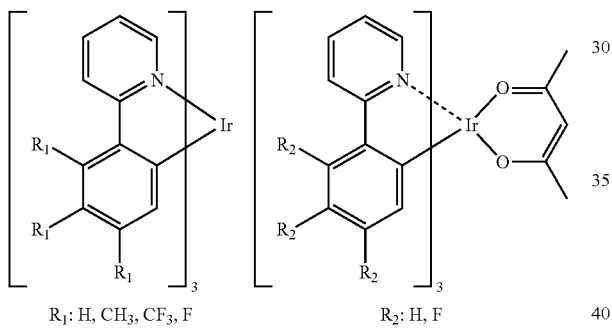

R$_1$: H, CH$_3$, CF$_3$, F    R$_2$: H, F

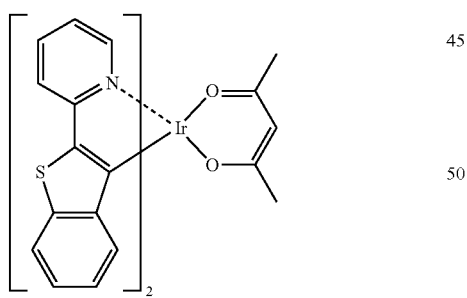

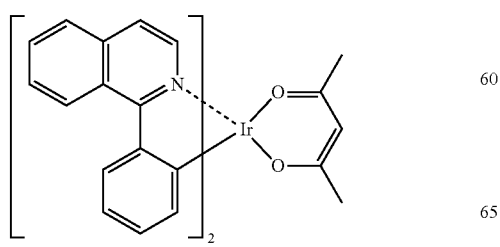

-continued

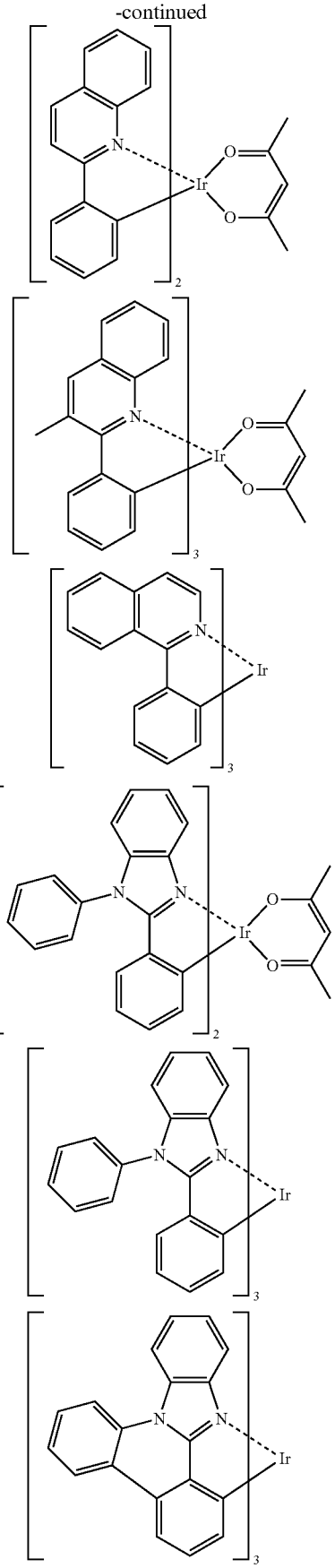

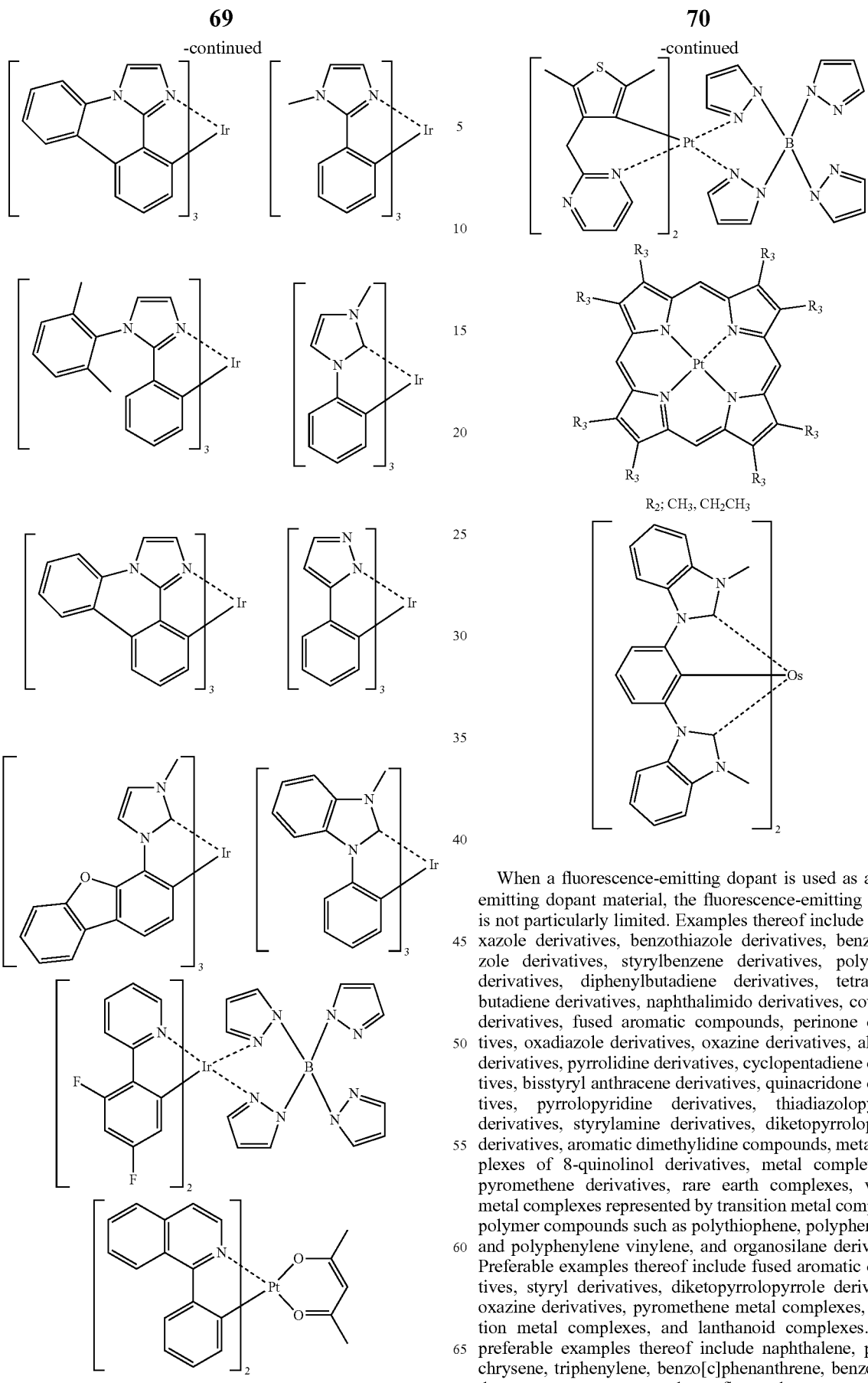

When a fluorescence-emitting dopant is used as a light-emitting dopant material, the fluorescence-emitting dopant is not particularly limited. Examples thereof include benzoxazole derivatives, benzothiazole derivatives, benzimidazole derivatives, styrylbenzene derivatives, polyphenyl derivatives, diphenylbutadiene derivatives, tetraphenyl butadiene derivatives, naphthalimido derivatives, coumarin derivatives, fused aromatic compounds, perinone derivatives, oxadiazole derivatives, oxazine derivatives, aldazine derivatives, pyrrolidine derivatives, cyclopentadiene derivatives, bisstyryl anthracene derivatives, quinacridone derivatives, pyrrolopyridine derivatives, thiadiazolopyridine derivatives, styrylamine derivatives, diketopyrrolopyrrole derivatives, aromatic dimethylidine compounds, metal complexes of 8-quinolinol derivatives, metal complexes of pyromethene derivatives, rare earth complexes, various metal complexes represented by transition metal complexes, polymer compounds such as polythiophene, polyphenylene, and polyphenylene vinylene, and organosilane derivatives. Preferable examples thereof include fused aromatic derivatives, styryl derivatives, diketopyrrolopyrrole derivatives, oxazine derivatives, pyromethene metal complexes, transition metal complexes, and lanthanoid complexes. More preferable examples thereof include naphthalene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthalene, hexacene, naphtho[2,1-f]isoquinoline, α-naphthaphenanthridine, phenanthrooxazole, quinolino[6,5-f]quinoline, and benzothiophanthrene. These may have an alkyl group, an aryl group, an aromatic heterocyclic group, or a diarylamino group as a substituent.

Only one type of a fluorescence-emitting dopant material may be contained in the light-emitting layer or two or more types thereof may be contained. A content of the fluorescence-emitting dopant material is preferably 0.1% to 20% and more preferably 1% to 10% with respect to the host material.

When a thermally activated delayed fluorescence-emitting dopant is used as a light-emitting dopant material, the thermally activated delayed fluorescence-emitting dopant is not particularly limited. Examples thereof include metal complexes such as a tin complex and a copper complex, indolocarbazole derivatives described in WO 2011/070963, cyanobenzene derivatives and carbazole derivatives described in Nature 2012, 492, 234, and phenazine derivatives, oxadiazole derivatives, triazole derivatives, sulfone derivatives, phenoxazine derivatives, and acridine derivatives described in Nature Photonics 2014, 8, 326.

The thermally activated delayed fluorescence-emitting dopant material is not particularly limited, and specific examples thereof include the following.

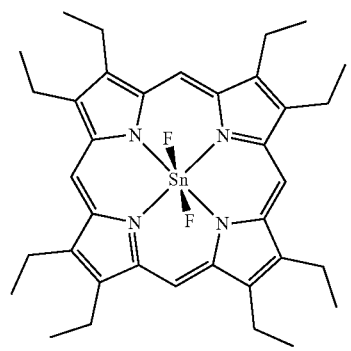

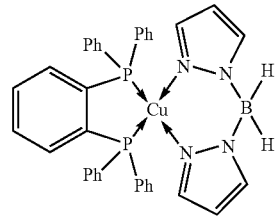

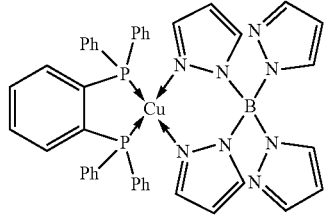

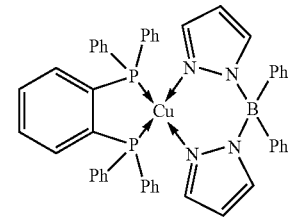

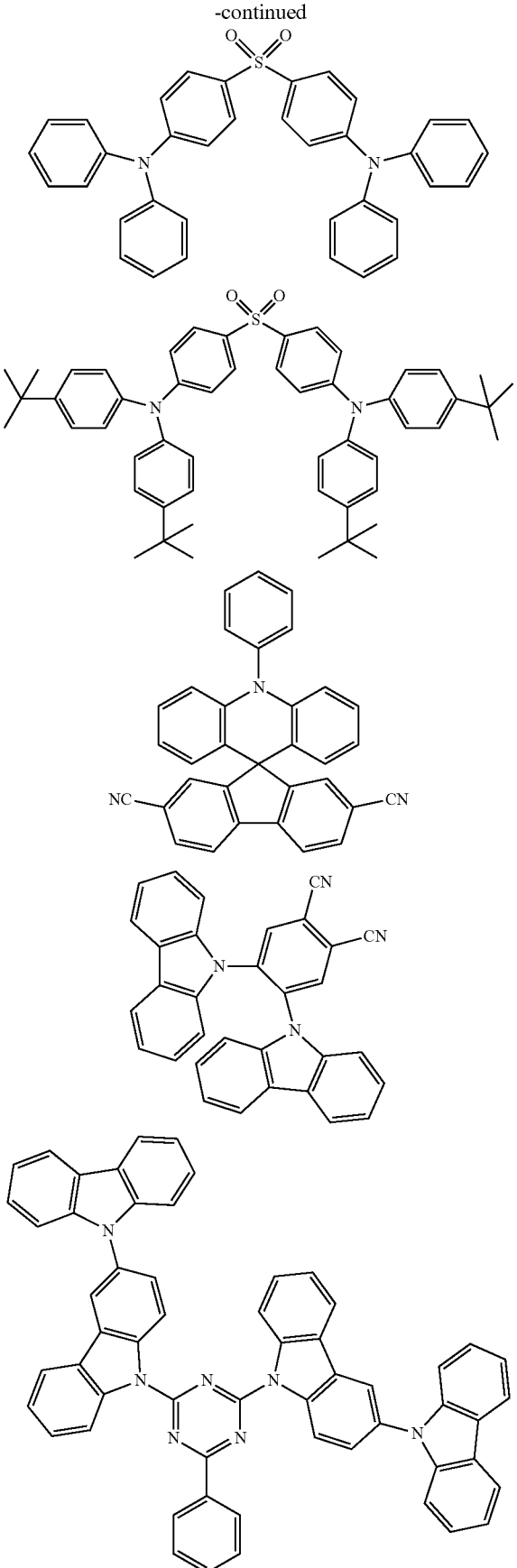

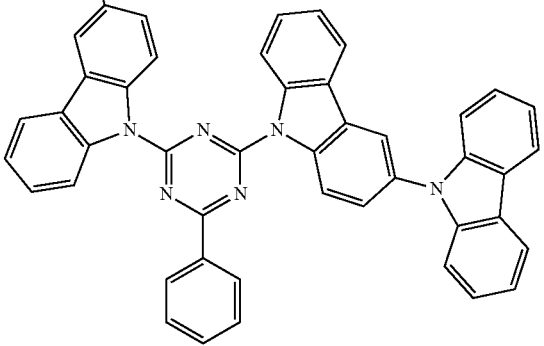

-continued

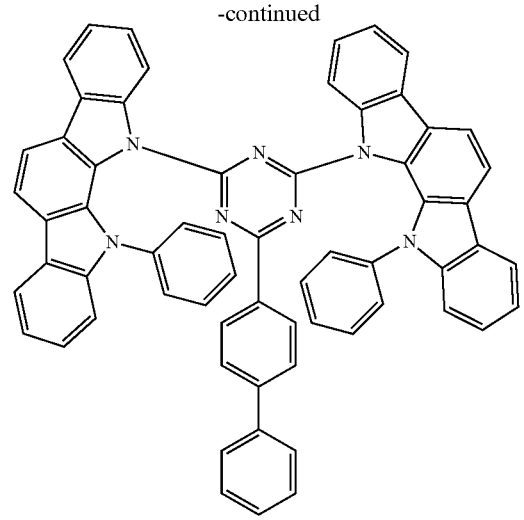

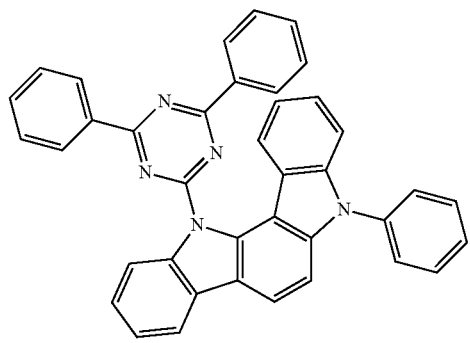

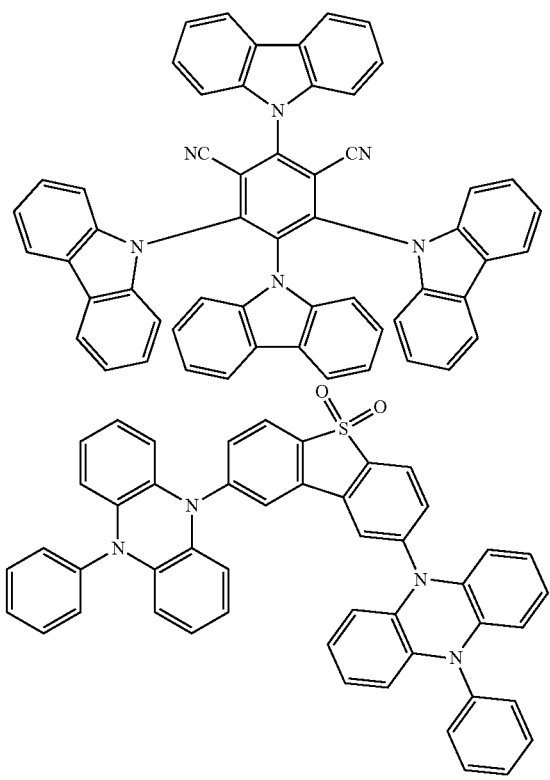

-continued

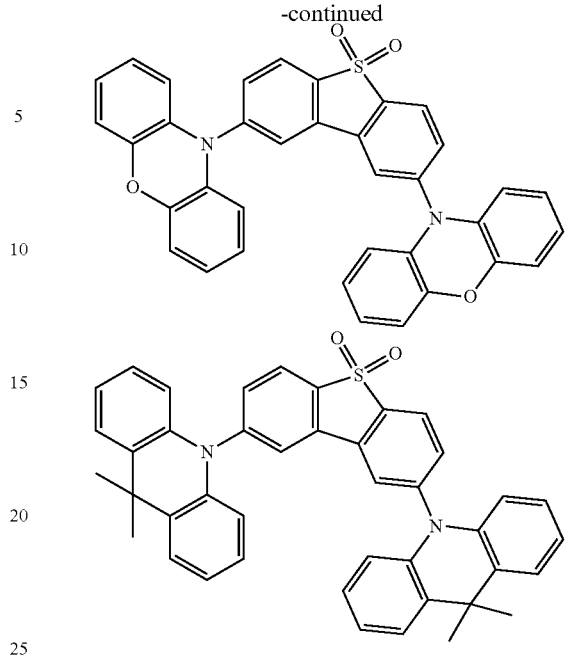

Only one type of a thermally activated delayed fluorescence-emitting dopant material may be contained in the light-emitting layer or two or more types thereof may be contained. In addition, the thermally activated delayed fluorescence-emitting dopant may be used in a combination of a phosphorescent dopant and a fluorescence-emitting dopant. A content of the thermally activated delayed fluorescence-emitting dopant material is preferably 0.1% to 50% and more preferably 1% to 30% with respect to the host material.

—Injection Layer—

The injection layer is a layer that is provided between an electrode and an organic layer in order to lower a driving voltage and improve light emission brightness, and includes a hole injection layer and an electron injection layer, and may be present between the anode and the light-emitting layer or the hole transport layer, and between the cathode and the light-emitting layer or the electron transport layer. The injection layer can be provided as necessary.

—Hole Blocking Layer—

The hole blocking layer has a function of the electron transport layer in a broad sense, and is made of a hole blocking material having a function of transporting electrons and a significantly low ability to transport holes, and can block holes while transporting electrons, and thus can improve a probability of recombining electrons and holes in the light-emitting layer.

A known hole blocking layer material can be used for the hole blocking layer, and an indolocarbazole compound is preferably contained. Any indolocarbazole compound may be used as long as it has one or more indolocarbazole rings. Here, the indolocarbazole ring is a ring in which 5 rings are fused in formula (1). A compound represented by formula (1) or a compound in which, in formula (1), $Ar^1$ represents a phenyl group, a biphenyl group or a terphenyl group, R represents an aliphatic hydrocarbon group having 1 to 10 carbon atoms, an aromatic hydrocarbon group having 6 to 10 carbon atoms, or an aromatic heterocyclic group having 3 to 12 carbon atoms, a, b, and c each independently represent an integer of 0 to 3, and m and n each independently represent an integer of 0 to 2, is preferable.

—Electron Blocking Layer—

The electron blocking layer has a function of a hole transport layer in a broad sense and blocks electrons while transporting holes, and thus can improve a probability of recombining electrons and holes in the light-emitting layer.

Regarding the material of the electron blocking layer, a known electron blocking layer material can be used and a material of the hole transport layer to be described below can be used as necessary. The film thickness of the electron blocking layer is preferably 3 to 100 nm, and more preferably 5 to 30 nm.

—Exciton Blocking Layer—

The exciton blocking layer is a layer for blocking diffusion of excitons generated when holes and electrons are recombined in the light-emitting layer in a charge transport layer, and when this layer is inserted, excitons can be efficiently confined in the light-emitting layer, and the luminous efficiency of the element can be improved. The exciton blocking layer can be inserted between two adjacent light-emitting layers in an element in which two or more light-emitting layers are adjacent to each other.

Regarding the material of the exciton blocking layer, a known exciton blocking layer material can be used. Examples thereof include 1,3-dicarbazolyl benzene (mCP) and bis(2-methyl-8-quinolinolato)-4-phenylphenolato aluminum(III) (BAlq).

—Hole Transport Layer—

The hole transport layer is made of a hole transport material having a function of transporting holes, and a single hole transport layer or a plurality of hole transport layers can be provided.

The hole transport material has either hole injection or transport properties or electron barrier properties, and may be an organic material or an inorganic material. For the hole transport layer, any one selected from among conventionally known compounds can be used. Examples of such a hole transport material include porphyrin derivatives, arylamine derivatives, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styryl anthracene derivatives, fluorenone derivatives, hydrazone derivatives, stilbene derivatives, silazane derivatives, an aniline copolymer, and a conductive polymer oligomer, and particularly a thiophene oligomer. Porphyrin derivatives, arylamine derivatives, or styrylamine derivatives are preferably used. An arylamine compound is more preferably used.

—Electron Transport Layer—

The electron transport layer is made of a material having a function of transporting electrons, and a single electron transport layer or a plurality of electron transport layers can be provided.

The electron transport material (which may also be a hole blocking material) may have a function of transferring electrons injected from the cathode to the light-emitting layer. For the electron transport layer, any one selected from among conventionally known compounds can be used, and examples thereof include polycyclic aromatic derivatives such as naphthalene, anthracene, and phenanthroline, tris(8-quinolinolato)aluminum(III) derivatives, phosphine oxide derivatives, nitro-substituted fluorene derivatives, diphenylquinone derivatives, thiopyrandioxide derivatives, carbodiimide, freorenylidene methane derivatives, anthraquinodimethane and anthrone derivatives, bipyridine derivatives, quinoline derivatives, oxadiazole derivatives, benzimidazole derivatives, benzothiazole derivatives, and indolocarbazole derivatives. In addition, a polymer material in which such a material is introduced into a polymer chain or such a material is used for a main chain of a polymer can be used.

EXAMPLES

While the present invention will be described below in more detail with reference to examples, the present invention is not limited to these examples, and can be implemented in various forms without departing from the scope and spirit thereof.

Compound 1-2 (0.20 g) and Compound 2-1 (0.80 g) were weighed out and mixed together while being ground in a mortar to prepare Pre-mixture H1.

In the same manner, Pre-mixtures H2 to H15 were prepared using first hosts and second hosts shown in Table 1.

Types and mixing ratios of first hosts and second hosts are shown in Table 1. Here, the compound numbers correspond to the numbers assigned to the exemplary compounds.

TABLE 1

| Pre-mixture | First host compound | Second host compound |
| --- | --- | --- |
| H1 | 1-2 (30%) | 2-1 (70%) |
| H2 | 1-2 (50%) | 2-1 (50%) |
| H3 | 1-5 (30%) | 2-2 (70%) |
| H4 | 1-5 (50%) | 2-2 (50%) |
| H5 | 1-7 (30%) | 2-2 (70%) |
| H6 | 1-7 (50%) | 2-2 (50%) |
| H7 | 1-7 (30%) | 2-3 (70%) |
| H8 | 1-7 (50%) | 2-3 (50%) |
| H9 | 1-10 (30%) | 2-2 (70%) |
| H10 | 1-10 (50%) | 2-2 (50%) |
| H11 | 1-15 (30%) | 2-3 (70%) |
| H12 | 1-15 (50%) | 2-3 (50%) |
| H13 | 1-109 (30%) | 2-2 (70%) |
| H14 | 1-109 (40%) | 2-2 (60%) |
| H15 | 1-109 (50%) | 2-2 (50%) |

Chemical formulae of Compounds A, B and C used as hosts or hole blocking layer compounds for comparison are shown below.

[C24]

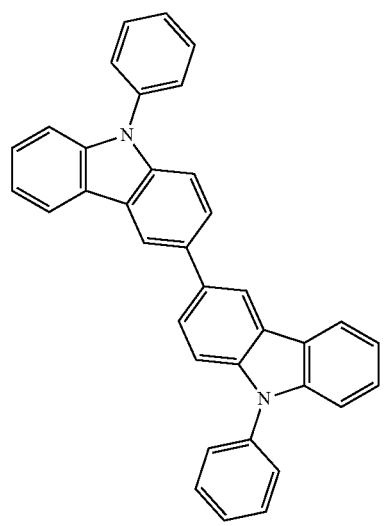

A

-continued

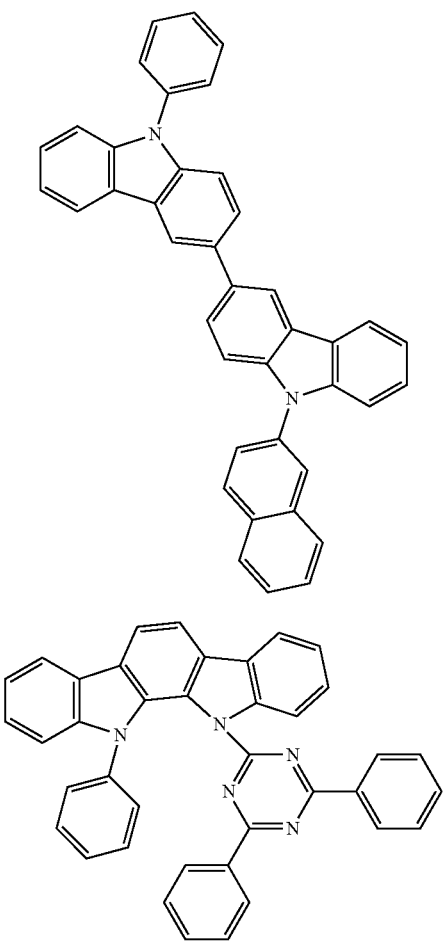

Table 2 shows the 50% weight reduction temperature ($T_{50}$) of Compounds 1-2, 1-5, 1-7, 1-10, 1-15, 1-109, 2-1, 2-2, and 2-3 and Compounds A, B, and C.

TABLE 2

| Compound | $T_{50}$ (° C.) |
|---|---|
| 1-2 | 317 |
| 1-5 | 342 |
| 1-7 | 346 |
| 1-10 | 342 |
| 1-15 | 355 |
| 1-109 | 333 |
| 2-1 | 331 |
| 2-2 | 338 |
| 2-3 | 364 |
| A | 293 |
| B | 328 |
| C | 281 |

Example 1

On a glass substrate on which an anode made of ITO with a film thickness of 110 nm was formed, respective thin films were laminated using a vacuum evaporation method at a degree of vacuum of $4.0 \times 10^{-5}$ Pa. First, HAT-CN was formed with a thickness of 25 nm as a hole injection layer on ITO, and next NPD was formed with a thickness of 30 nm as a hole transport layer. Next, HT-1 was formed with a thickness of 10 nm as an electron blocking layer. Then, Pre-mixture H1 as a host and Ir(ppy)$_3$ as a light-emitting dopant were co-vapor-deposited from different vapor deposition sources to form a light-emitting layer with a thickness of 40 nm. In this case, co-vapor-deposition was performed under vapor deposition conditions such that the concentration of Ir(ppy)$_3$ was 10 wt %. Next, ET-1 was formed with a thickness of 20 nm as an electron transport layer. In addition, lithium fluoride (LiF) was formed with a thickness of 1 nm as an electron injection layer on the electron transport layer. Finally, aluminum (Al) was formed with a thickness of 70 nm as a cathode on the electron injection layer to produce an organic EL element.

Examples 2 to 15

Organic EL elements were produced in the same manner as in Example 1 except that any of Pre-mixtures H2 to H15 was used as the host in Example 1.

Example 16

An organic EL element was produced in the same manner as in Example 1 except that, in Example 1, a light-emitting layer was formed using Pre-mixture H1 as a host and Ir(ppy)$_3$ as a light-emitting dopant, and Compound C was then formed with a thickness of 10 nm as a hole blocking layer on the light-emitting layer, and next ET-1 was formed with a thickness of 10 nm as the electron transport layer.

Examples 17 to 20

Organic EL elements were produced in the same manner as in Example 16 except that any of Pre-mixtures H3, H7, H9, and H11 was used as the host in Example 16.

The brightness, driving voltage, luminous efficiency, and lifespan characteristics of the produced organic EL elements are shown in Tables 3 to 7. In the tables, the brightness, driving voltage, and luminous efficiency were values at a drive current of 20 mA/cm$^2$ and were initial characteristics. LT70 was a time taken for the brightness to be reduced to 70% of the initial brightness when the initial brightness was 9,000 cd/m$^2$, and LT95 was a time taken for the brightness to be reduced to 95% of the initial brightness when the initial brightness was 3,700 cd/m$^2$, and both are lifespan characteristics.

TABLE 3

| Example | Pre-mixture | Hole blocking layer compound | Brightness (cd/m$^2$) | Voltage (V) | Power efficiency (lm/W) | LT70 (h) |
|---|---|---|---|---|---|---|
| 1 | H1 | | 12200 | 4.3 | 44.6 | 1030 |
| 2 | H2 | | 12900 | 3.8 | 52.7 | 890 |
| 3 | H3 | | 12400 | 4.5 | 43.3 | 1130 |
| 4 | H4 | | 13700 | 3.9 | 55.2 | 950 |
| 5 | H5 | | 12300 | 4.4 | 43.9 | 1030 |
| 6 | H6 | | 11100 | 3.7 | 47.1 | 840 |
| 7 | H7 | | 11100 | 4.3 | 40.5 | 1030 |
| 8 | H8 | | 12100 | 3.8 | 50.0 | 920 |
| 9 | H9 | | 12300 | 4.5 | 42.9 | 910 |
| 10 | H10 | | 12500 | 4.0 | 49.1 | 800 |
| 11 | H11 | | 12300 | 4.1 | 47.1 | 1000 |
| 12 | H12 | | 12900 | 3.6 | 56.3 | 880 |
| 13 | H13 | | 11471 | 4.7 | 38.7 | 4000 |
| 14 | H14 | | 12033 | 4.2 | 45.2 | 3900 |
| 15 | H15 | | 12132 | 3.8 | 50.3 | 2800 |
| 16 | H1 | C | 12200 | 4.3 | 44.5 | 1240 |

TABLE 3-continued

| Example | Pre-mixture | Hole blocking layer compound | Brightness (cd/m²) | Voltage (V) | Power efficiency (lm/W) | LT70 (h) |
|---|---|---|---|---|---|---|
| 17 | H3 | C | 12800 | 4.7 | 42.6 | 1250 |
| 18 | H7 | C | 12000 | 4.5 | 41.7 | 1130 |
| 19 | H9 | C | 12200 | 4.3 | 44.8 | 1000 |
| 20 | H11 | C | 12900 | 3.8 | 53.6 | 1100 |

Example 21

On a glass substrate on which an anode made of ITO with a film thickness of 110 nm was formed, respective thin films were laminated using a vacuum evaporation method at a degree of vacuum of 4.0×10⁻⁵ Pa. First, HAT-CN was formed with a thickness of 25 nm as a hole injection layer on ITO, and next NPD was formed with a thickness of 30 nm as a hole transport layer. Next, HT-1 was formed with a thickness of 10 nm as an electron blocking layer. Then, Compound 1-2 as a first host, Compound 2-1 as a second host, and Ir(ppy)₃ as a light-emitting dopant were co-vapor-deposited from different vapor deposition sources to form a light-emitting layer with a thickness of 40 nm. In this case, co-vapor-deposition was performed under vapor deposition conditions such that the concentration of Ir(ppy)₃ was 10 wt %, and the weight ratio between the first host and the second host was 30:70. Next, ET-1 was formed with a thickness of 20 nm as an electron transport layer. In addition, LiF was formed with a thickness of 1 nm as an electron injection layer on the electron transport layer. Finally, Al was formed with a thickness of 70 nm as a cathode on the electron injection layer to produce an organic EL element.

Examples 22 to 39

Organic EL elements were produced in the same manner as in Example 21 except that compounds shown in Table 4 were used as the first host and the second host in Example 21.

Examples 40 to 42

Organic EL elements were produced in the same manner as in Examples 21 to 23 except that a light-emitting layer was formed, Compound C was then formed with a thickness of 10 nm as a hole blocking layer, and ET-1 was formed with a thickness of 10 nm as an electron transport layer in Examples 21 to 23.

Types and proportions of first hosts and second hosts used, and evaluation results of the produced organic EL elements are shown in Table 4.

TABLE 4

| Example | First host compound | Second host compound | Brightness (cd/m²) | Voltage (V) | Power efficiency (lm/W) | LT70 (h) |
|---|---|---|---|---|---|---|
| 21 | 1-2 (30%) | 2-1 (70%) | 12200 | 4.3 | 44.6 | 1130 |
| 22 | 1-1 (30%) | 2-3 (70%) | 12100 | 4.5 | 42.2 | 1250 |
| 23 | 1-2 (30%) | 2-3 (70%) | 12200 | 4.2 | 45.6 | 1300 |
| 24 | 1-5 (30%) | 2-2 (70%) | 12200 | 4.5 | 42.6 | 1250 |
| 25 | 1-5 (30%) | 2-3 (70%) | 11900 | 4.4 | 42.4 | 1310 |
| 26 | 1-7 (30%) | 2-2 (70%) | 12100 | 4.4 | 43.1 | 1080 |
| 27 | 1-7 (30%) | 2-3 (70%) | 12300 | 4.3 | 44.7 | 1140 |
| 28 | 1-10 (30%) | 2-2 (70%) | 12000 | 4.5 | 41.9 | 950 |
| 29 | 1-10 (30%) | 2-3 (70%) | 12700 | 4.5 | 44.3 | 1000 |
| 30 | 1-26 (30%) | 2-3 (70%) | 12800 | 4.8 | 41.8 | 900 |
| 31 | 1-74 (30%) | 2-3 (70%) | 13400 | 4.4 | 47.7 | 810 |
| 32 | 1-84 (30%) | 2-3 (70%) | 12600 | 4.8 | 41.1 | 800 |
| 33 | 1-92 (30%) | 2-3 (70%) | 12000 | 4.1 | 46.5 | 900 |
| 34 | 1-94 (30%) | 2-3 (70%) | 12600 | 4.7 | 42.1 | 840 |
| 35 | 1-2 (30%) | 2-2 (70%) | 11613 | 4.4 | 41.6 | 3400 |
| 36 | 1-109 (30%) | 2-2 (70%) | 11376 | 4.2 | 42.5 | 4300 |
| 37 | 1-109 (30%) | 2-43 (70%) | 11784 | 4.1 | 44.8 | 4100 |
| 38 | 1-9 (30%) | 2-2 (70%) | 11447 | 4.6 | 57.7 | 2800 |
| 39 | 1-114 (30%) | 2-2 (70%) | 10605 | 4.6 | 53.5 | 2600 |
| 40 | 1-2 (30%) | 2-1 (70%) | 11900 | 4.4 | 42.5 | 1190 |
| 41 | 1-1 (30%) | 2-3 (70%) | 11800 | 4.4 | 42.1 | 1310 |
| 42 | 1-2 (30%) | 2-3 (70%) | 11900 | 4.4 | 42.5 | 1370 |

Example 43

On a glass substrate on which an anode made of ITO with a film thickness of 110 nm was formed, respective thin films were laminated using a vacuum evaporation method at a degree of vacuum of 4.0×10⁻⁵ Pa. First, HAT-CN was formed with a thickness of 25 nm as a hole injection layer on ITO, and next NPD was formed with a thickness of 45 nm as a hole transport layer. Next, HT-1 was formed with a thickness of 10 nm as an electron blocking layer. Then, Pre-mixture H1 as a host and Ir(piq)₂acac as a light-emitting dopant were co-vapor-deposited from different vapor deposition sources to form a light-emitting layer with a thickness of 40 nm. In this case, co-vapor-deposition was performed under vapor deposition conditions such that the concentration of Ir(piq)₂acac was 6.0 wt %. Next, ET-1 was formed with a thickness of 37.5 nm as an electron transport layer. Then, LiF was formed with a thickness of 1 nm as an electron injection layer on the electron transport layer. Finally, Al was formed with a thickness of 70 nm as a cathode on the electron injection layer to produce an organic EL element.

Examples 44 to 47

Organic EL elements were produced in the same manner as in Example 43 except that any of Pre-mixtures H3, H7, H9, and H11 was used as the host in Example 43.

Examples 48 to 52

Organic EL elements were produced in the same manner as in Examples 43 to 47 except that a light-emitting layer was formed, Compound C was then formed with a thickness of 10 nm as a hole blocking layer, and ET-1 was formed with a thickness of 10 nm as an electron transport layer in Examples 43 to 47.

Types of pre-mixtures used and evaluation results of the produced organic EL elements are shown in Table 5.

TABLE 5

| Example | Pre-mixture | Hole blocking layer compound | Brightness (cd/m²) | Voltage (V) | Power efficiency (lm/W) | LT95 (h) |
|---|---|---|---|---|---|---|
| 43 | H1 | | 4600 | 4.3 | 16.8 | 400 |
| 44 | H3 | | 4300 | 4.5 | 15.0 | 400 |

TABLE 5-continued

| Example | Pre-mixture | Hole blocking layer compound | Brightness (cd/m$^2$) | Voltage (V) | Power efficiency (lm/W) | LT95 (h) |
|---|---|---|---|---|---|---|
| 45 | H7 |   | 4100 | 4.4 | 14.6 | 380 |
| 46 | H9 |   | 4300 | 4.4 | 15.4 | 340 |
| 47 | H11 |   | 4300 | 4.2 | 16.1 | 320 |
| 48 | H1 | C | 5300 | 4.4 | 18.9 | 440 |
| 49 | H3 | C | 5000 | 4.5 | 17.5 | 420 |
| 50 | H7 | C | 4800 | 4.5 | 16.8 | 400 |
| 51 | H9 | C | 5000 | 4.5 | 17.5 | 360 |
| 52 | H11 | C | 4900 | 4.3 | 17.9 | 340 |

Example 53

On a glass substrate on which an anode made of ITO with a film thickness of 110 nm was formed, respective thin films were laminated using a vacuum evaporation method at a degree of vacuum of 4.0×10$^{-5}$ Pa. First, HAT-CN was formed with a thickness of 25 nm as a hole injection layer on ITO, and next NPD was formed with a thickness of 45 nm as a hole transport layer. Next, HT-1 was formed with a thickness of 10 nm as an electron blocking layer. Then, Compound 1-2 as a first host, Compound 2-1 as a second host, and Ir(piq)$_2$acac as a light-emitting dopant were co-vapor-deposited from different vapor deposition sources to form a light-emitting layer with a thickness of 40 nm. In this case, co-vapor-deposition was performed under vapor deposition conditions such that the concentration of Ir(piq)$_2$acac was 6.0 wt %, and the weight ratio between the first host and the second host was 50:50. Next, ET-1 was formed with a thickness of 37.5 nm as an electron transport layer. Then, LiF was formed with a thickness of 1 nm as an electron injection layer on the electron transport layer. Finally, Al was formed with a thickness of 70 nm as a cathode on the electron injection layer to produce an organic EL element.

Examples 54 to 66

Organic EL elements were produced in the same manner as in Example 53 except that compounds shown in Table 6 were used as first hosts and second hosts in Example 53.

Examples 67 to 69

Organic EL elements were produced in the same manner as in Examples 53 to 55 except that a light-emitting layer was formed, Compound C was then formed with a thickness of 10 nm as a hole blocking layer, and ET-1 was formed with a thickness of 10 nm as an electron transport layer in Examples 53 to 55.

Types and proportions of first hosts and second hosts used, and evaluation results of the produced organic EL elements are shown in Table 6.

TABLE 6

| Example | First host compound | Second host compound | Brightness (cd/m$^2$) | Voltage (V) | Power efficiency (lm/W) | LT95 (h) |
|---|---|---|---|---|---|---|
| 53 | 1-2 (50%) | 2-1 (50%) | 4500 | 4.3 | 16.4 | 420 |
| 54 | 1-1 (50%) | 2-3 (50%) | 4900 | 4.6 | 16.7 | 440 |
| 55 | 1-2 (50%) | 2-3 (50%) | 4700 | 4.3 | 17.2 | 460 |
| 56 | 1-5 (50%) | 2-2 (50%) | 4900 | 4.6 | 16.7 | 420 |
| 57 | 1-5 (50%) | 2-3 (50%) | 5200 | 4.4 | 18.6 | 440 |
| 58 | 1-7 (50%) | 2-2 (50%) | 4500 | 4.3 | 16.4 | 410 |
| 59 | 1-7 (50%) | 2-3 (50%) | 4600 | 4.3 | 16.8 | 420 |
| 60 | 1-10 (50%) | 2-2 (50%) | 4700 | 4.4 | 16.8 | 370 |
| 61 | 1-10 (50%) | 2-3 (50%) | 4700 | 4.3 | 17.2 | 380 |
| 62 | 1-26 (50%) | 2-3 (50%) | 4700 | 4.5 | 16.4 | 390 |
| 63 | 1-74 (50%) | 2-3 (50%) | 4200 | 4.3 | 15.3 | 410 |
| 64 | 1-84 (50%) | 2-3 (50%) | 4600 | 4.3 | 16.8 | 410 |
| 65 | 1-92 (50%) | 2-3 (50%) | 4500 | 4.2 | 16.8 | 440 |
| 66 | 1-94 (50%) | 2-3 (50%) | 4200 | 4.2 | 15.7 | 440 |
| 67 | 1-2 (50%) | 2-1 (50%) | 5200 | 4.4 | 18.6 | 440 |
| 68 | 1-1 (50%) | 2-3 (50%) | 5700 | 4.6 | 19.5 | 460 |
| 69 | 1-2 (50%) | 2-3 (50%) | 5400 | 4.4 | 19.3 | 480 |

Comparative Example 1

An organic EL element was produced in the same manner as in Example 1 except that Compound 1-2 alone was used as the host in Example 1. The thickness of the light-emitting layer and the light-emitting dopant concentration were the same as those in Example 1.

Comparative Examples 2 to 9

Organic EL elements were produced in the same manner as in Comparative Example 1 except that compounds alone shown in Table 7 were used as the host.

Comparative Examples 10 and 11

Organic EL elements were produced in the same manner as in Example 21 except that Compound 1-2 was used as a first host and Compound A or Compound B was used as a second host in Example 21.

Comparative Examples 12 to 15

Organic EL elements were produced in the same manner as in Example 21 except that Compound C was used as a first host and Compound A, 2-1, 2-2, or 2-3 was used as a second host in Example 21.

Comparative Examples 16 and 17

Organic EL elements were produced in the same manner as in Example 53 except that Compound 1-2 was used as a first host and Compound A or Compound B was used as a second host in Example 53.

Evaluation results of the produced organic EL elements are shown in Table 7. Here, regarding lifespan characteristics, LT95 was used for Comparative Examples 16 and 17 and is marked with *.

TABLE 7

| Comparative Example | First host compound | Second host compound | Brightness (cd/m²) | Voltage (V) | Power efficiency (lm/W) | LT70 (h) |
|---|---|---|---|---|---|---|
| 1 | 1-2 | — | 7100 | 3.0 | 37.2 | 560 |
| 2 | 1-5 | — | 7000 | 3.3 | 33.3 | 580 |
| 3 | 1-7 | — | 4200 | 3.1 | 21.3 | 570 |
| 4 | 1-10 | — | 4600 | 3.2 | 22.6 | 600 |
| 5 | 1-15 | — | 7034 | 3.9 | 28.4 | 149 |
| 6 | 1-109 | — | 10658 | 3.2 | 53.3 | 490 |
| 7 | — | 2-1 | 4590 | 5.1 | 14.1 | 320 |
| 8 | — | 2-2 | 4900 | 4.8 | 16.0 | 410 |
| 9 | — | 2-3 | 5100 | 4.7 | 17.0 | 410 |
| 10 | 1-2 (30%) | A (70%) | 13400 | 4.7 | 44.8 | 620 |
| 11 | 1-2 (30%) | B (70%) | 9800 | 4.1 | 37.5 | 680 |
| 12 | C (30%) | A (70%) | 9245 | 4.3 | 24.3 | 600 |
| 13 | C (30%) | 2-1 (70%) | 11683 | 3.6 | 51.6 | 240 |
| 14 | C (30%) | 2-2 (70%) | 11486 | 4.1 | 43.6 | 720 |
| 15 | C (30%) | 2-3 (70%) | 10954 | 3.5 | 49.7 | 570 |
| 16 | 1-2 (50%) | A (50%) | 3300 | 4.4 | 11.8 | 230* |
| 17 | 1-2 (30%) | B (70%) | 2400 | 4.1 | 9.2 | 270* |

It was found that, when the organic EL elements produced in Examples 1 to 42 and Comparative Examples 1 to 15 were connected to an external power supply and supplied with a DC voltage, an emission spectrum with a maximal wavelength of 530 nm was observed in all of the elements, and light emission from Ir(ppy)₃ was obtained.

In addition, it was found that, when organic EL elements produced in Examples 43 to 69 and Comparative Examples 16 and 17 were connected to an external power supply and supplied with a DC voltage, an emission spectrum with a maximal wavelength of 620 nm was observed in all of the elements, and light emission from Ir(pic)₂acac was obtained.

Based on Tables 3 to 7, it was found that, when the first host represented by formula (1) and the second host represented by formula (2) were mixed and used, lifespan characteristics were significantly prolonged.

In addition, it was found that, when an indolocarbazole compound was used as a hole blocking material as in Examples 16 to 20, Examples 40 to 42, Examples 48 to 52, and Examples 67 to 69, lifespan characteristics were prolonged.

Compounds used in examples are shown below.

[C25]

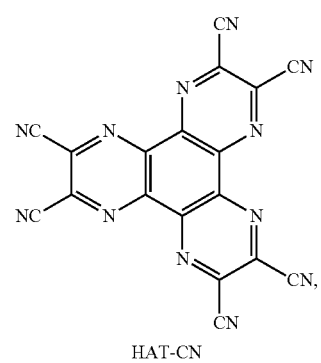

HAT-CN

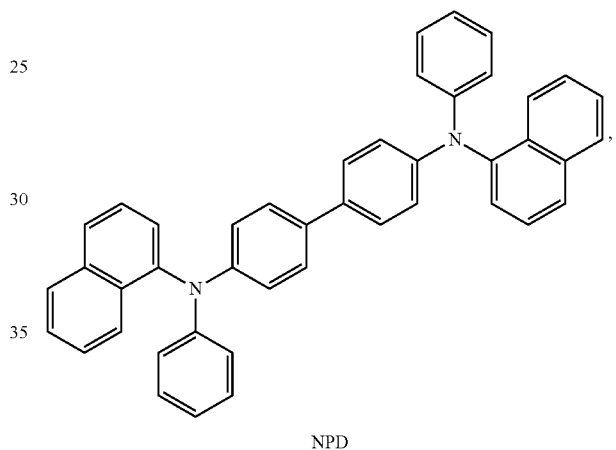

NPD

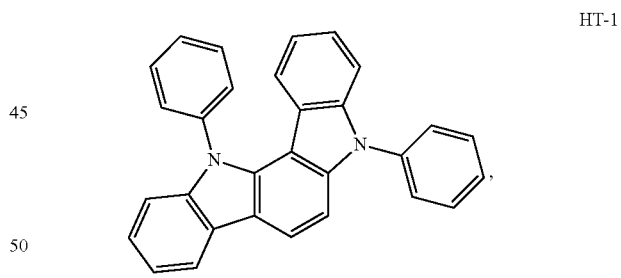

HT-1

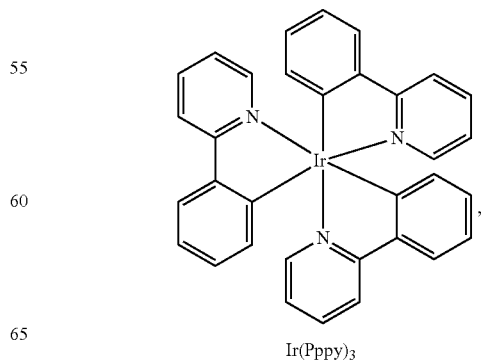

Ir(Pppy)₃

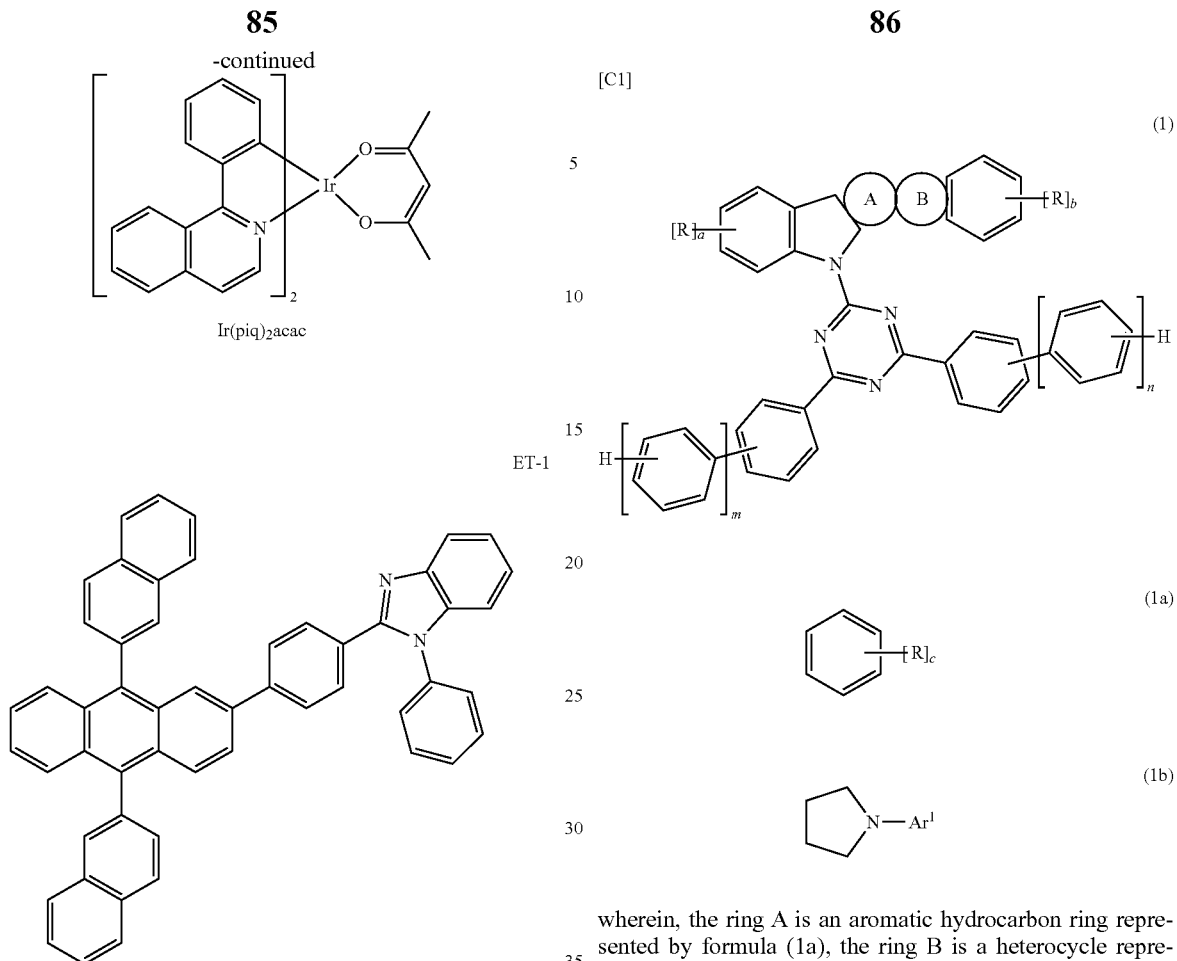

Ir(piq)₂acac

ET-1

INDUSTRIAL APPLICABILITY

The organic EL element of the present invention has a low driving voltage, high efficiency, and high driving stability.

REFERENCE SIGNS LIST

1 Substrate
2 Anode
3 Hole injection layer
4 Hole transport layer
5 Light-emitting layer
6 Electron transport layer
7 Cathode

The invention claimed is:

1. An organic electroluminescent element comprising one or more light-emitting layers between an anode and a cathode which face each other, wherein at least one light-emitting layer contains a first host selected from among compounds represented by the following formula (1), a second host selected from among compounds represented by the following formula (2), and a light-emitting dopant material,

[C1]

wherein, the ring A is an aromatic hydrocarbon ring represented by formula (1a), the ring B is a heterocycle represented by formula (1b), and the ring A and the ring B are each fused to an adjacent ring at any position, $Ar^1$ represents a phenyl group, a biphenyl group or a terphenyl group, R each independently represents an aliphatic hydrocarbon group having 1 to 10 carbon atoms, an aromatic hydrocarbon group having 6 to 10 carbon atoms, or an aromatic heterocyclic group having 3 to 12 carbon atoms, a, b, and c each independently represent an integer of 0 to 3, and m and n each independently represent an integer of 0 to 2, wherein when AO is a phenyl group, m+n is an integer of 1 to 4;

[C2]

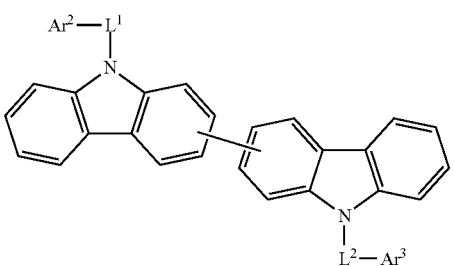

wherein, Ar² and Ar³ represent a hydrogen atom, an aromatic hydrocarbon group having 6 to 14 carbon atoms, or a group in which two of the aromatic hydrocarbon groups are linked to each other, and the aromatic hydrocarbon groups to be linked to each other may be the same as or different from each other, with the proviso that Ar² and Ar³ are not both a hydrogen atom, and L¹ and L² represent an m-phenylene group or a p-phenylene group.

2. The organic electroluminescent element according to claim 1,
wherein, in formula (2), Ar² represents a hydrogen atom or a phenyl group, and AO represents a phenyl group.

3. The organic electroluminescent element according to claim 1,
wherein the compound represented by formula (2) is a compound represented by any of the following formulae (3) to (5):

[C3]

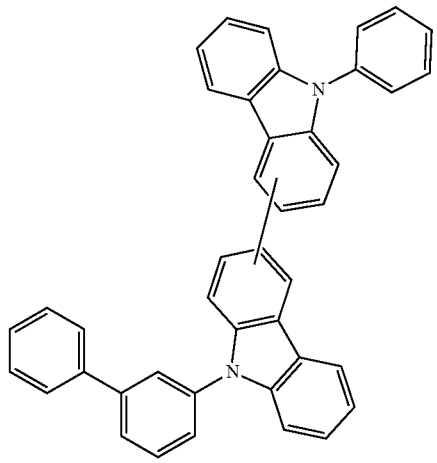

(3)

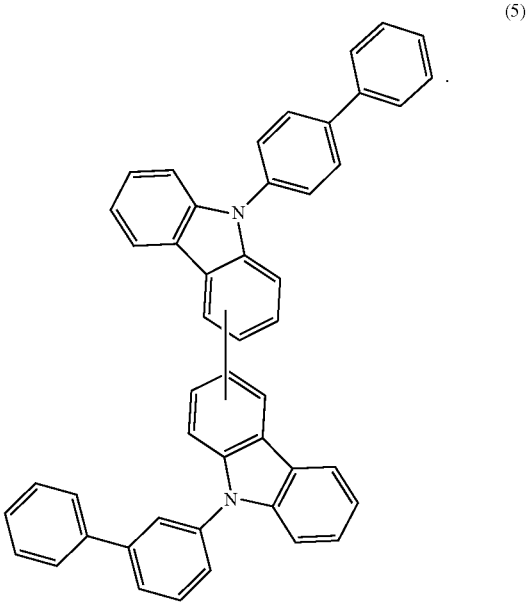

(5)

4. The organic electroluminescent element according to claim 3,
wherein the compound represented by formula (2) is a compound represented by formula (4).

5. The organic electroluminescent element according to claim 3,
wherein the compound represented by formula (2) is a compound represented by formula (5).

6. The organic electroluminescent element according to claim 1,
wherein the compound represented by formula (1) is a compound represented by any of formulae (6) to (11):

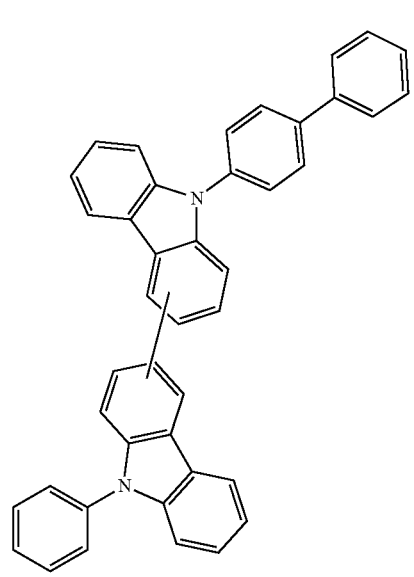

(4)

[C4]

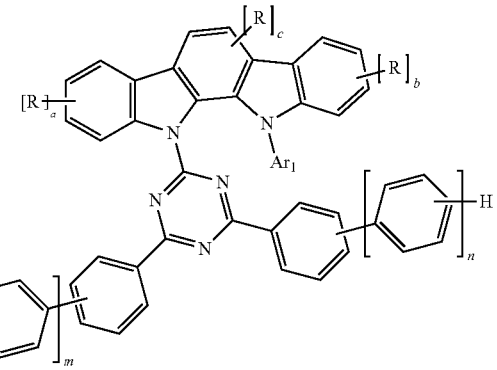

(6)

(7)
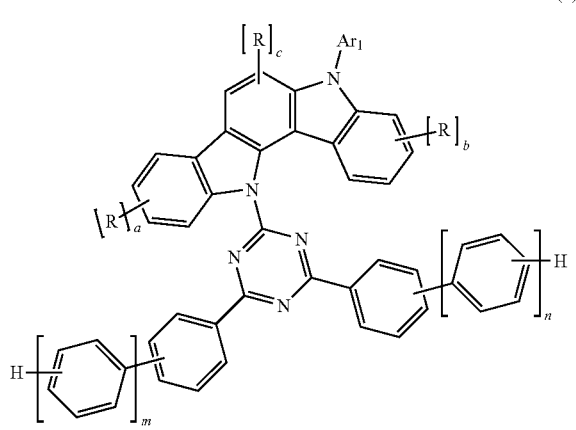

(8)
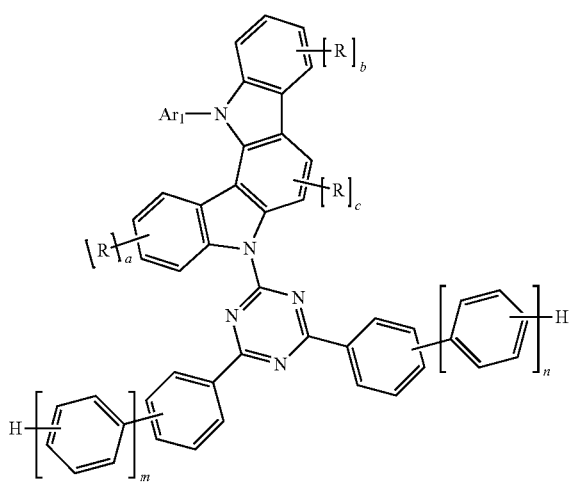

(9)
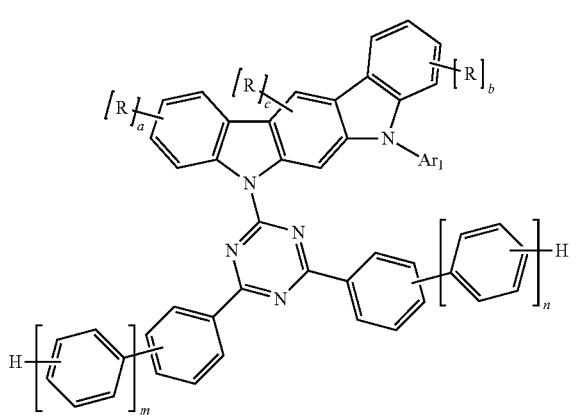

(10)
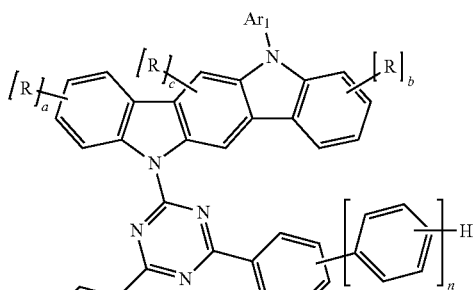

(11)
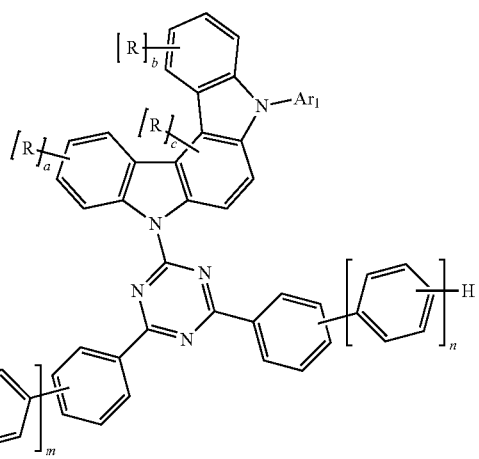

wherein, $Ar^1$, R, a to c, m, and n have the same meaning as in formula (1).

7. The organic electroluminescent element according to claim 1,
wherein a proportion of the first host is larger than 20 wt % and less than 55 wt % with respect to a total amount of the first host and the second host.

8. The organic electroluminescent element according to claim 1,
wherein the light-emitting dopant material is an organic metal complex containing at least one metal selected from the group consisting of ruthenium, rhodium, palladium, silver, rhenium, osmium, iridium, platinum and gold.

9. The organic electroluminescent element according to claim 1,
wherein the light-emitting dopant material is a thermally activated delayed fluorescence-emitting dopant material.

10. The organic electroluminescent element according to claim 1,
wherein a hole blocking layer is provided adjacent to the light-emitting layer, and the hole blocking layer contains an indolocarbazole compound.

11. A method of producing an organic electroluminescent element, comprising:
a step of, when the organic electroluminescent element according to claim 1 is produced, mixing a first host and a second host to prepare a pre-mixture, and then vapor-depositing a host material containing the premixture to form a light-emitting layer.

12. The method of producing an organic electroluminescent element according to claim 11,
wherein a difference between 50% weight reduction temperatures of the first host and the second host is within 20° C.

* * * * *